US008648907B2

(12) United States Patent
Kanamori

(10) Patent No.: US 8,648,907 B2
(45) Date of Patent: Feb. 11, 2014

(54) IMAGE PROCESSING APPARATUS

(75) Inventor: Katsuhiro Kanamori, Nara (JP)

(73) Assignee: Panasonic Corporation, Osaka (JP)

(*) Notice: Subject to any disclaimer, the term of this patent is extended or adjusted under 35 U.S.C. 154(b) by 0 days.

(21) Appl. No.: 13/571,686

(22) Filed: Aug. 10, 2012

(65) Prior Publication Data
US 2012/0307028 A1 Dec. 6, 2012

Related U.S. Application Data

(63) Continuation of application No. PCT/JP2011/005293, filed on Sep. 20, 2011.

(30) Foreign Application Priority Data

Nov. 30, 2010 (JP) .................................. 2010-267436

(51) Int. Cl.
*H04N 13/00* (2006.01)
(52) U.S. Cl.
USPC ......................................................... 348/135
(58) Field of Classification Search
None
See application file for complete search history.

(56) References Cited

U.S. PATENT DOCUMENTS

| | | | | |
|---|---|---|---|---|
| 5,914,782 | A * | 6/1999 | Sugiyama | ..................... 356/491 |
| 2003/0076412 | A1 | 4/2003 | Ozawa | |
| 2009/0079982 | A1 | 3/2009 | Lefaudeux | |
| 2009/0290039 | A1 | 11/2009 | Kanamori et al. | |
| 2010/0079757 | A1 | 4/2010 | Murooka et al. | |
| 2011/0267483 | A1 | 11/2011 | Kanamori | |

FOREIGN PATENT DOCUMENTS

| | | |
|---|---|---|
| JP | 10-104524 A | 4/1998 |
| JP | 10-122829 A | 5/1998 |
| JP | 11-313242 A | 11/1999 |
| JP | 3869698 B | 10/2006 |
| JP | 4235252 B | 12/2008 |
| JP | 2009-246770 A | 11/2009 |
| JP | 2010-082271 A | 4/2010 |
| JP | 2010-104424 A | 5/2010 |
| JP | 4762369 B | 6/2011 |

OTHER PUBLICATIONS

International Search Report for corresponding International Application No. PCT/JP2011/005293 mailed Dec. 20, 2011.

(Continued)

*Primary Examiner* — Dave Czekaj
*Assistant Examiner* — M D Haque
(74) *Attorney, Agent, or Firm* — Renner, Otto, Boisselle & Sklar, LLP

(57) ABSTRACT

An exemplary image processing apparatus comprises: a polarized light source section; an image capturing section which sequentially captures an image of the object that is being illuminated with each of three or more plane polarized light rays; and an image processing section. The image processing section includes: a varying intensity processing section which calculates a state of polarized light reflected from the object's surface; a reflection decision section which distinguishes a multi-reflection region in which incoming light is reflected twice from a recessed region from a once-reflected region in which the incoming light is reflected only once from the object's surface; and a mirror image search section which locates a pair of multi-reflection regions. Based on the pair of multi-reflection regions, the image processing section generates an image representing the recessed region on the object's surface.

24 Claims, 42 Drawing Sheets

(56) References Cited

OTHER PUBLICATIONS

Lefaudeux et al., "Compact and robust linear Stokes polarization camera", Proc. SPIE, vol. 6972, 69720B, Polarization: Measurement, Analysis, and Remote Sensing VIII (2008) (cited in [0086] of the specification).

Katsushi Ikeuchi; "Determining 3D Shape from 2D Shading Information Based on the Reflectance Map Technique", Institute of Electronics and Communication Engineers of Japan, Trans. D, Jul. 1982, vol. J65-D, No. 7, pp. 842-849 (cited in [0185] of the specification).

* cited by examiner

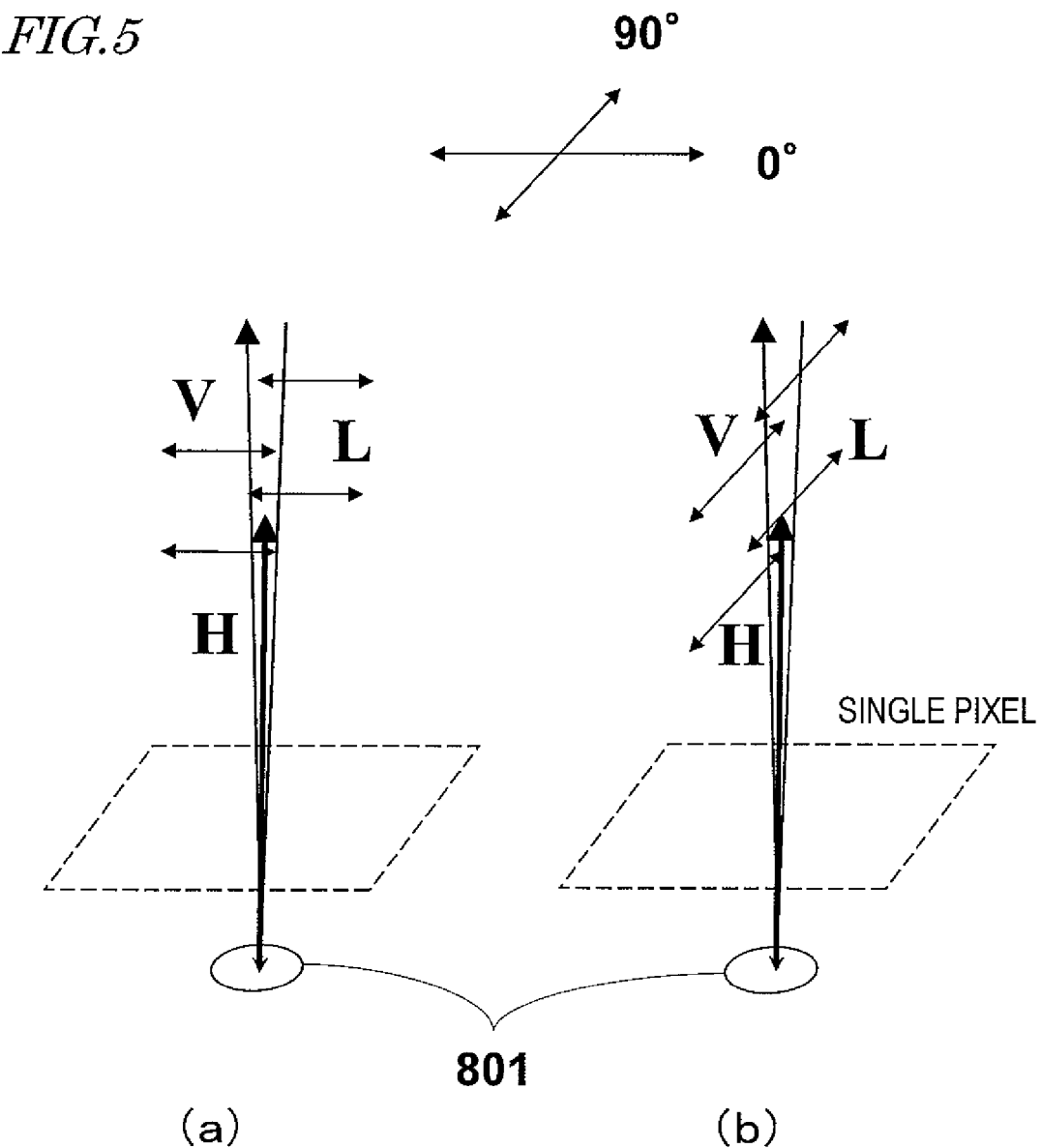

*FIG.9A* *FIG.9B*
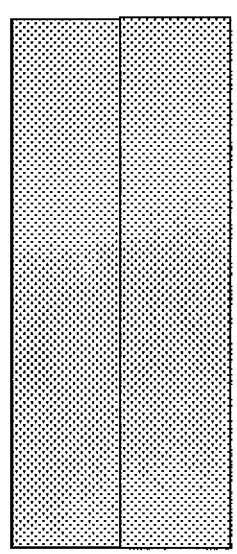
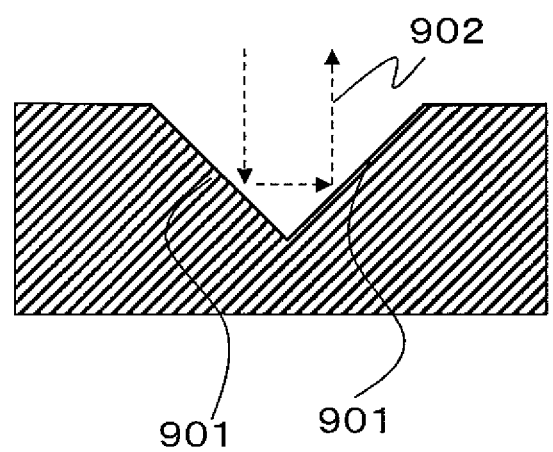

FIG.17B
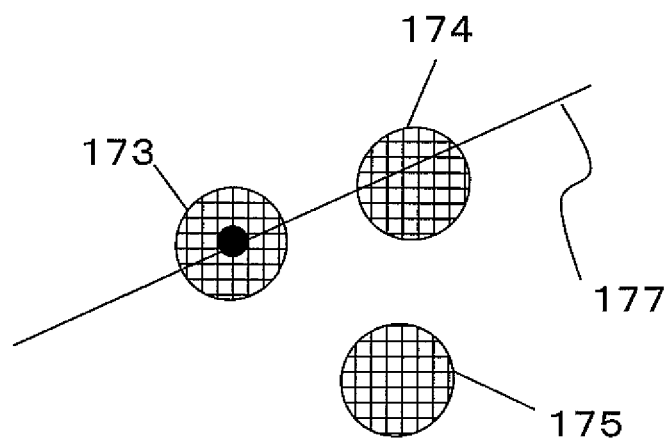
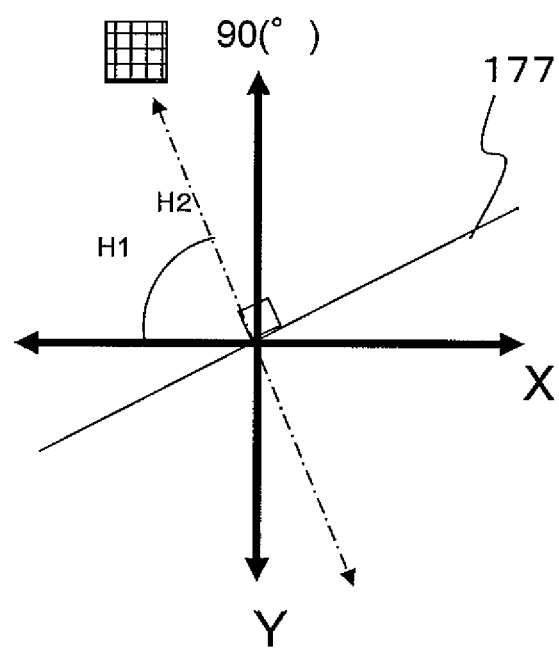

2001

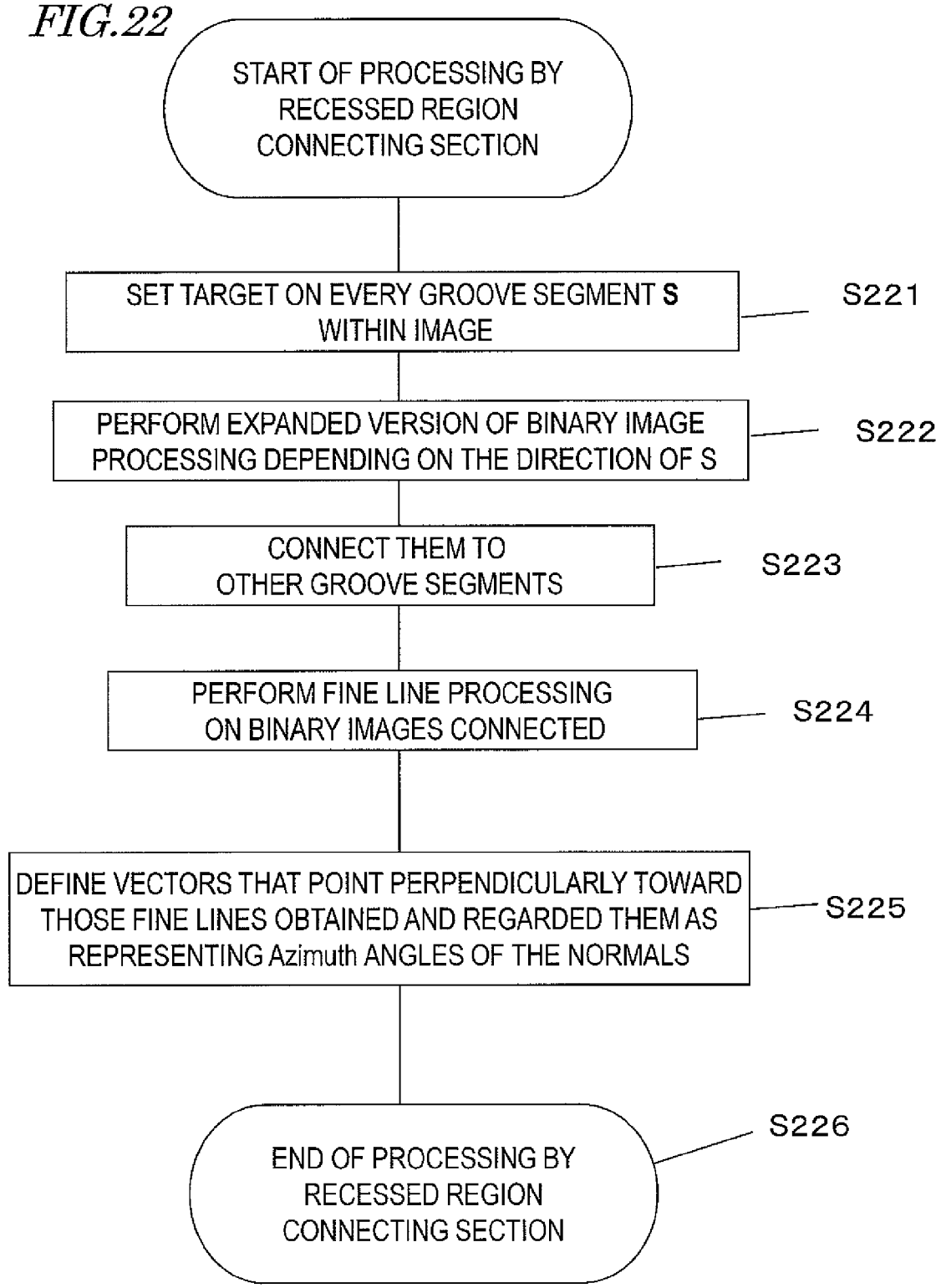

IMAGE PROCESSING APPARATUS

This is a continuation of International Application No. PCT/JP2011/005293, with an international filing date of Sep. 20, 2011, which claims priority of Japanese Patent Application No. 2010-267436, filed on Nov. 30, 2010, the contents of which are hereby incorporated by reference.

BACKGROUND

1. Technical Field

The present disclosure relates to an image processing apparatus that can obtain surface unevenness information or surface topography images.

2. Description of the Related Art

An endoscope captures an image of an organism's organ by irradiating the wall surface of the organ, which is covered with a mucosa, with illuminating light. In the field of such endoscopes, not only changing colors of the surface but also the texture of minute unevenness on the surface need to be observed and confirmed. However, in order to avoid casting shadows on the object, an endoscope usually sets the angle formed between the optical axis of the illuminating light and that of image capturing light to be approximately zero degrees, and therefore, it is difficult for the endoscope to capture such a surface unevenness structure (micro-geometry or surface topography) with shadows. To overcome such a problem, someone has proposed a technique for recognizing the surface unevenness by reference to information about the color shade of the given image by slightly modifying the image processing process for an existent color luminance based endoscope image capturing system. Meanwhile, a polarization endoscope that uses a polarized light source and polarization image capturing in combination has also been proposed.

The former technique is disclosed in Japanese Patent Publication No. 3869698, for example.

Meanwhile, the latter technique is disclosed in Japanese Laid-Open Patent Publication No. 2009-246770 and Japanese Laid-Open Patent Publication No. 2010-104424, for example.

SUMMARY

The prior art technique needs further improvement in view of the quality of surface topography images. One non-limiting, and exemplary embodiment improves the quality of surface topography images.

In one general aspect, an image processing apparatus includes: a polarized light source section which sequentially illuminates an object with three or more kinds of plane polarized light rays, of which the planes of polarization define mutually different angles; an image capturing section which sequentially captures an image of the object that is being illuminated with each of the three or more kinds of plane polarized light rays; and an image processing section. The image processing section includes: a varying intensity processing section which calculates a state of polarized light being reflected from the object's surface by processing the intensity of the image that has been shot by the image capturing section; a reflection decision section which distinguishes, based on the output of the varying intensity processing section, the multi-reflection region in which incoming light is reflected twice from the recessed region before returning from a once-reflected region in which the incoming light is reflected only once from the object's surface before returning; and a mirror image search section which locates a pair of multi-reflection regions in which the incoming light is reflected twice from the recessed region on the object's surface before returning. Based on the pair of multi-reflection regions, the image processing section generates an image representing the recessed region on the object's surface.

In one general aspect, an image processing method includes: a polarized light illuminating step for sequentially illuminating an object with three or more kinds of plane polarized light rays, of which the planes of polarization define mutually different angles; an image capturing step for sequentially capturing an image of the object that is being illuminated with each of the three or more kinds of plane polarized light rays; and an image processing step. The image processing step includes: a varying intensity processing step for calculating a state of polarized light being reflected from the object's surface by processing the intensity of the image that has been shot in the image capturing step; a reflection decision step for distinguishing, based on a result of the varying intensity processing step, a multi-reflection region in which incoming light is reflected twice from a recessed region before returning from a once-reflected region in which the incoming light is reflected only once from the object's surface before returning; a mirror image searching step for locating a pair of multi-reflection regions in which the incoming light is reflected twice from the recessed region on the object's surface before returning; and the step of generating an image representing the recessed region on the object's surface based on the pair of multi-reflection regions.

In one general aspect, an endoscope device includes: a polarized light source section which sequentially illuminates an object with three or more kinds of plane polarized light rays, of which the planes of polarization define mutually different angles; an image capturing section which sequentially captures an image of the object that is being illuminated with each of the three or more kinds of plane polarized light rays; an image processing section; and a display section which displays an image based on the output of the image processing section. The image processing section includes: a varying intensity processing section which calculates a state of polarized light being reflected from the object's surface by processing the intensity of the image that has been shot by the image capturing section; and a pseudo-color image transforming section which generates a pseudo-color image based on the output of the varying intensity processing section. The varying intensity processing section obtains a relation between the angle of the plane of polarization and the intensity value of each pixel based on a pixel signal supplied from the image capturing section, thereby generating not only an intensity maximizing angle image that is defined by the angle of the plane of polarization that maximizes the intensity value with respect to each said pixel but also a degree of intensity modulation image that is defined by the ratio of the amplitude of variation in the intensity value caused by the change of the plane of polarization to an average intensity value with respect to each said pixel. Based on the intensity maximizing angle image and the degree of intensity modulation image, the pseudo-color image transforming section generates a pseudo-color image that uses the intensity maximizing angle and the degree of intensity modulation as a hue angle and as a saturation, respectively, synthesizes the pseudo-color image and the light intensity image together, and gets their synthetic image displayed on the display section.

According to the above aspect, it is possible to improve the quality of the captured surface topography images. These general and specific aspects may be implemented using a system, a method, and a computer program, and any combination of systems, methods, and computer programs.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

BRIEF DESCRIPTION OF THE DRAWINGS

FIG. 5 illustrates how incoming light that has come from over an object is incident on the object's surface and reflected once.

FIG. 9A illustrates the shape of a simplest groove and FIG. 9B illustrates how incoming light is reflected from it.

FIG. 17B illustrates how the mirror image search section performs its processing.

FIG. 22 is a flowchart showing the procedure of processing to be performed by a recessed region connecting section.

DETAILED DESCRIPTION

Figure 1A:
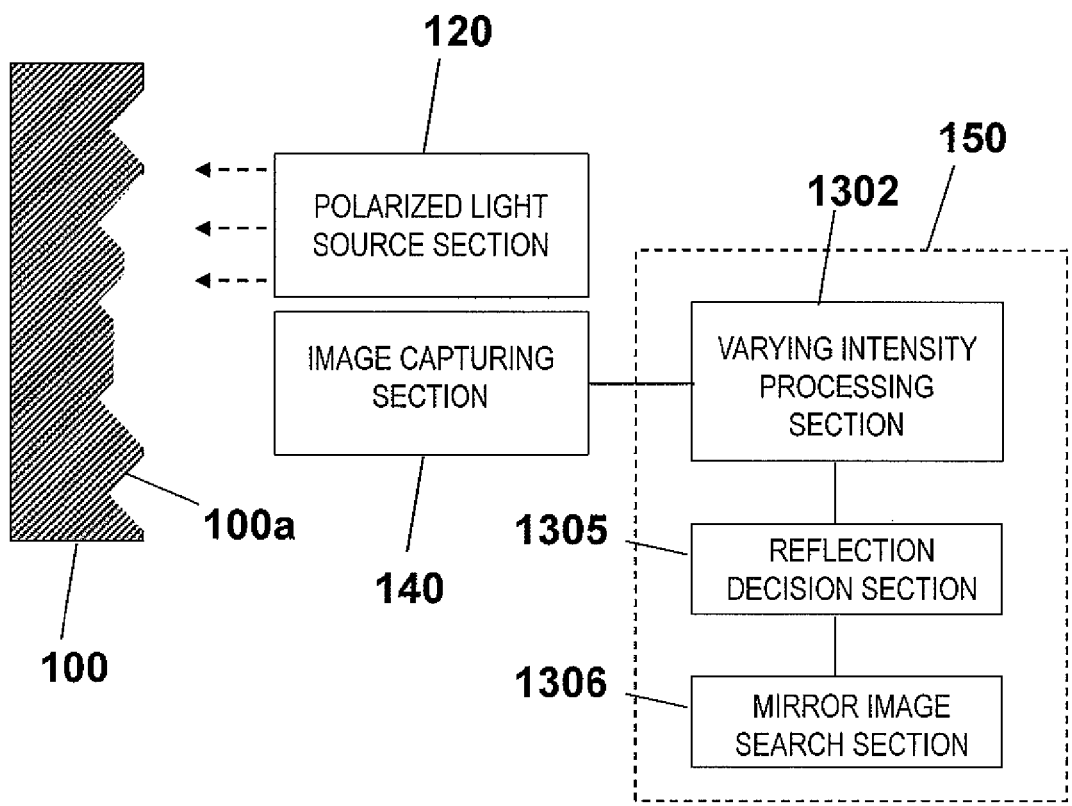
FIG. 1A is a diagram illustrating a basic configuration for an image processing apparatus according to the present disclosure.

As shown in FIG. 1A, an embodiment of an image processing apparatus according to the present disclosure comprises a polarized light source section 120, an image capturing section 140, a varying intensity processing section 1302, a reflection decision section 1305, and a mirror image search section 1306. The latter three sections 1302, 1305 and 1306 are included in an image processing section 150.

The polarized light source section 120 sequentially illuminates an object 100 with three or more kinds of plane polarized light rays, of which the planes of polarization have mutually different angles. On the surface of the object 100 of shooting according to the present disclosure, there are multiple recessed regions 100a. If the object 100 is the surface of an organism's organ, for example, multiple recessed regions are observed. A plane polarized light ray is reflected by the recessed regions 100a and the other regions on the surface of the object 100 and then incident on the image capturing section 140. When the object 100 is being illuminated with each of the three or more kinds of plane polarized light rays, the image capturing section 140 shoots the object 100 sequentially.

Figure 1B:
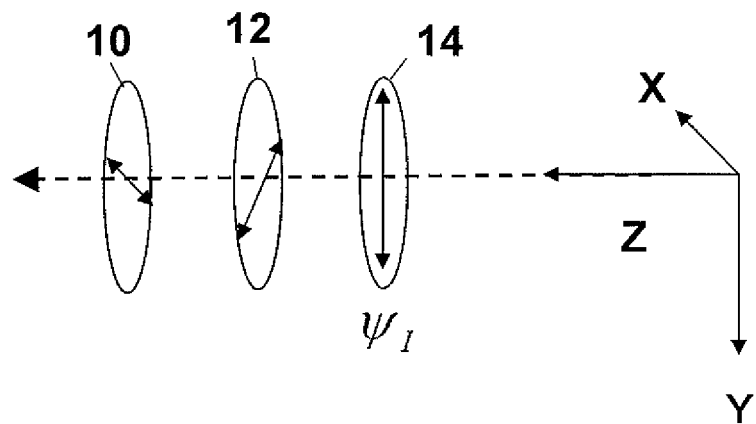
FIG. 1B is a perspective view schematically illustrating the polarization directions of three plane polarized light rays, of which the planes of polarization define mutually different angles.

FIG. 1B is a perspective view schematically showing the polarization directions of three kinds of plane polarized light rays, of which the planes of polarization have mutually different angles. The three polarization states 10, 12 and 14 illustrated in FIG. 1B have planes of polarization that have mutually different angles. Inside each of these circles schematically illustrating the respective polarization states 10, 12 and 14 in FIG. 1B, shown is a double-headed arrow, which indicates the vibration direction of the electric vector that defines the plane of polarization of a plane polarized light ray.

The XYZ coordinates shown in FIG. 1B are of the right-handed system. In this description, the X- and Y-axes are defined in the plane of the image captured by the image capturing section 140, and the negative direction of the Z-axis is defined to be the viewing direction (i.e., the optical axis direction). The plane of polarization of a plane polarized light ray is a plane that is parallel to the vibrating electric vector and that includes the optical axis. If this coordinate system is adopted, the electric vector vibration direction of the plane polarized light ray is parallel to the XY plane. That is why the angle (ψI) of the plane of polarization is defined to be the angle formed by the polarization direction (i.e., the electric vector vibration direction) with respect to the positive X-axis direction. This angle ψI will be described in detail later with reference to FIG. 3.

According to the present disclosure, the polarized light source section 120 sequentially illuminates the object 100 with three or more kinds of plane polarized light rays, of which the planes of polarization have mutually different angles. And while the object 100 is being illuminated with each of the three or more kinds of plane polarized light rays, the image capturing section 140 shoots the object 100 sequentially.

Now let's go back to FIG. 1A. The varying intensity processing section 1302 obtains a relation between the angle of the plane of polarization and the intensity value of each pixel based on a pixel signal supplied from the image capturing section 140, thereby generating an "intensity maximizing angle image" and a "degree of intensity modulation image". In this description, the "intensity maximizing angle image" is an image that is defined by the angle of the plane of polarization that maximizes the intensity value with respect to each of the pixels that form the image captured. For example, if the intensity value of a pixel P (x, y) that is defined by a set of coordinates (x, y) becomes maximum when the object 100 is illuminated with a plane polarized light ray, of which the plane of polarization has an angle of 45 degrees, then an intensity maximizing angle of 45 degrees is set with respect to that pixel P (x, y). A single "intensity maximizing angle image" is formed by setting such an intensity maximizing angle value for each of multiple pixels. On the other hand, the "degree of intensity modulation image" is an image that is defined by the ratio of the amplitude of variation in the intensity value caused by the change of the plane of polarization to an average intensity value with respect to each of multiple pixels. Specifically, if the degree of intensity modulation with respect to a certain pixel P (x, y) is 0.3, then the value of 0.3 is set for that pixel P (x, y). A single "degree of intensity modulation image" is formed by setting such a degree of intensity modulation value for each of multiple pixels.

As can be seen, in this description, an "image" refers herein to not only a light intensity image to be directly sensible to human eyes but also any arrangement of numerical values that are allocated to respective pixels. For example, if a single "intensity maximizing angle image" is displayed, the image can be displayed with lightness defined by the intensity maximizing angle value that has been set for each pixel of that intensity maximizing angle image. The intensity maximizing angle image represented in this manner does include a bright and dark pattern that is sensible to human eyes but that is different from an ordinary light intensity image representing the object's intensity. It should be noted that the data itself that represents any of various kinds of "images" will also be sometimes referred to herein as an "image" for the sake of simplicity.

Based on the output of the varying intensity processing section 1302, the reflection decision section 1305 shown in FIG. 1A distinguishes a multi-reflection region in which incoming light is reflected twice from a recessed region before returning from a once-reflected region in which the incoming light is reflected only once from the object's surface before returning. As will be described later, polarized light is reflected differently from a recessed region on an object's surface and from the other regions, and therefore, these regions can be distinguished from each other. Specifically, as a recessed region produces multiple reflection (typically, reflection in two steps), such a multi-reflection region makes a pair that exhibits similar polarized light reflection states. A typical example of such a multi-reflection region may be a groove with a V-cross section. As will be described later with reference to FIGS. 9A and 9B, a groove with the simplest structure is a groove that runs straight in one direction. The recessed region with a multi-reflection region just needs to have such surfaces that define a roughly V- or U-shaped sloped or curved cross section, and may have any other form. Even in the embodiment shown in FIGS. 10 to 12, its cross section may include roughly V- or U-sloped or curves faces as will be described later. Consequently, multiple reflection is produced on such faces and pairs of regions that exhibit similar polarized light reflection states can be observed.

Such pairs of multi-reflection regions that exhibit similar polarized light reflection states connect together on the object's surface, thus forming a broader recessed region. As a typical example of such a recessed region is a groove, a recessed region with pairs of multi-reflection regions will be sometimes referred to herein as a "groove". Nevertheless, in this description, the "groove" is not necessarily such a recessed groove that is extended in one direction on an object's surface. Rather, in this description, a "groove" may also be a recessed region with a non-groove shape, strictly speaking (e.g., the shapes shown in FIGS. 11A to 12B).

The mirror image search section 1306 determines in what pair of multi-reflection regions the incoming light is reflected twice from a recessed region on the object's surface to be returning light. It will be described in detail later how to determine such a pair. And the image generating section 150 generates an image representing a recessed region on the object's surface with respect to that multi-reflection region.

Figure 1C:
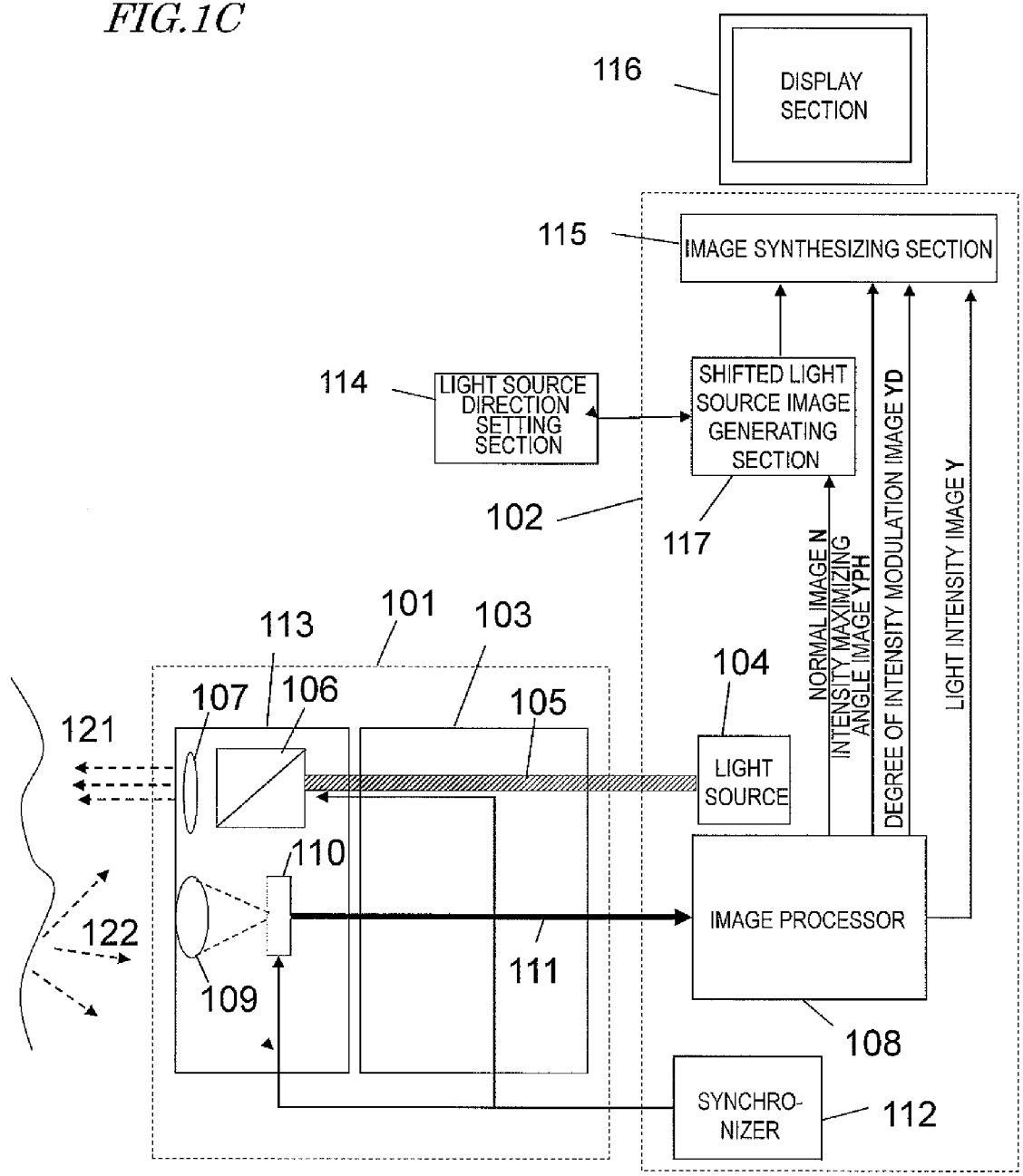
FIG. 1C is a diagram illustrating a configuration for an image processing apparatus as a first embodiment of the present disclosure.

FIG. 1C schematically illustrates an overall configuration for an image processing apparatus as a first embodiment of the present disclosure.

This image processing apparatus includes an endoscope 101 and a controller 102. The endoscope 101 includes a tip portion 113 with an image sensor 110 and an inserting portion 103 with a light guide 105 and a video signal line 111. The inserting portion 103 of the endoscope 101 has a structure that is elongated horizontally as shown in FIG. 1C and that can be bent flexibly. Even when bent, the light guide 105 can also propagate light.

The controller 102 includes a light source 104 and an image processor 108. The white non-polarized light that has been emitted from the light source 104 is guided through the light guide 105 to a plane of polarization control element 106 of the tip portion 113 to be plane polarized light rays 121 that irradiate the object with. The plane of polarization control element 106 may be made up of a polarizer and a liquid crystal element and can transform the non-polarized light into plane polarized light with an arbitrary plane of polarization using a voltage.

The plane of polarization control element 106 is a device that can rotate the plane of polarization using a liquid crystal material. Its exemplary configurations are already disclosed in Japanese Laid-Open Patent Publication No. 11-313242 and US 2009/0079982 A1, Nicolas Lefaudeux et al.: "Compact and Robust Linear Stokes Polarization Camera", Proc. SPIE, Vol. 6972, 69720B, Polarization: Measurement, Analysis, and Remote Sensing VIII (2008) and so on. The plane of polarization control element 106 may be implemented as a voltage application type liquid crystal device that includes a ferroelectric liquid crystal material, a polarization film and a quarter-wave plate in combination. And that polarized illumination is cast toward the object through an illuminating lens 107.

The synchronizer 112 gives the plane of polarization control element 106 an instruction to rotate the plane of polarization, thereby getting the plane of polarization of the illumination rotated. At the same time, the synchronizer 112 sends a shooting start signal to an image sensor 110, thereby getting video. The synchronizer 112 performs this series of processing steps a number of times.

The light 122 returning from the object is transmitted through a shooting lens 109 and then produces an image on the image sensor 110. This image sensor 110 may be either a monochrome image sensor or a single-panel color image sensor with a color mosaic. The video signal of the captured image is transmitted through the video signal line 111 to reach the image processor 108.

In this embodiment, the polarized light source section 120 shown in FIG. 1A is realized by the light source 104, the light guide 105, the plane of polarization control element 106 and the illuminating lens 107. Meanwhile, the image capturing section 140 shown in FIG. 1A is realized by the shooting lens 109 and the image sensor 110. And the varying intensity processing section 1302, the reflection decision section 1305 and the mirror image search section 1306 shown in FIG. 1A are realized by the image processor 108.

Figure 2:
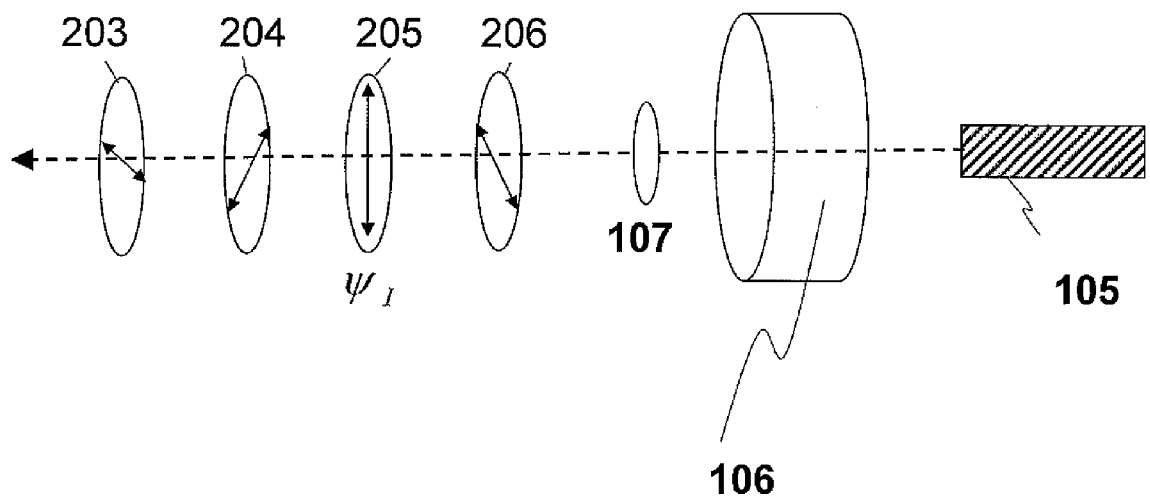
FIG. 2 shows how a plane of polarization control element operates.

Next, it will be described with reference to FIG. 2 how the plane of polarization control element 106 operates.

First, second, third and fourth images are captured in respective states 203, 204, 205 and 206 in which the plane of polarization has an angle of 0, 45, 90 and 135 degrees, respectively. These angles do not always have to be increased on a 45 degree basis. But the angle of increment may also be any other value obtained by dividing 180 degrees by an integer of three or more. If the image sensor has high sensitivity or if the illumination has high illuminance, then the exposure process time can be shortened. As a result, the angle of rotation can be set more finely.

According to the documents described above, the time it takes to rotate the plane of polarization may be as long as approximately 20 ms when the operating speed is low but may also be as short as 40 to 100 μsec when the operating speed is high. If a high-response-speed liquid crystal material is used and if the sensitivity of the image sensor is increased to a level that is high enough to get an image captured in such a short time, performance that is high enough to shoot a moving picture can be maintained even when the plane of polarization is rotated to those four directions one after another during shooting. Also, although the image processing is carried out on the basis of an image capturing unit of at least four frames, the processing can get done within one frame period by adopting pipeline processing.

As can be seen easily from FIG. 1C, the optical axis of the illuminating lens 107 is substantially aligned with that of the shooting lens 109. This arrangement is adopted in order to avoid casting shadows on the object as perfectly as possible when the object is monitored with an endoscope.

It should be noted that when an endoscope is used normally, the object is irradiated with non-polarized light in many cases. According to the present disclosure, by adding together mutually different polarization images as the first through fourth images, for example, a non-polarized average light intensity image can be generated. The present inventors discovered via experiments that when the images represented by multiple polarized light rays, of which the planes of polarization were defined by angles ψI at regular intervals and which had been radiated toward, and had returned from, the object, were added together, the effect of polarization was canceled and the effect eventually achieved was the same as the one achieved by using a non-polarized light source.

Figure 3:
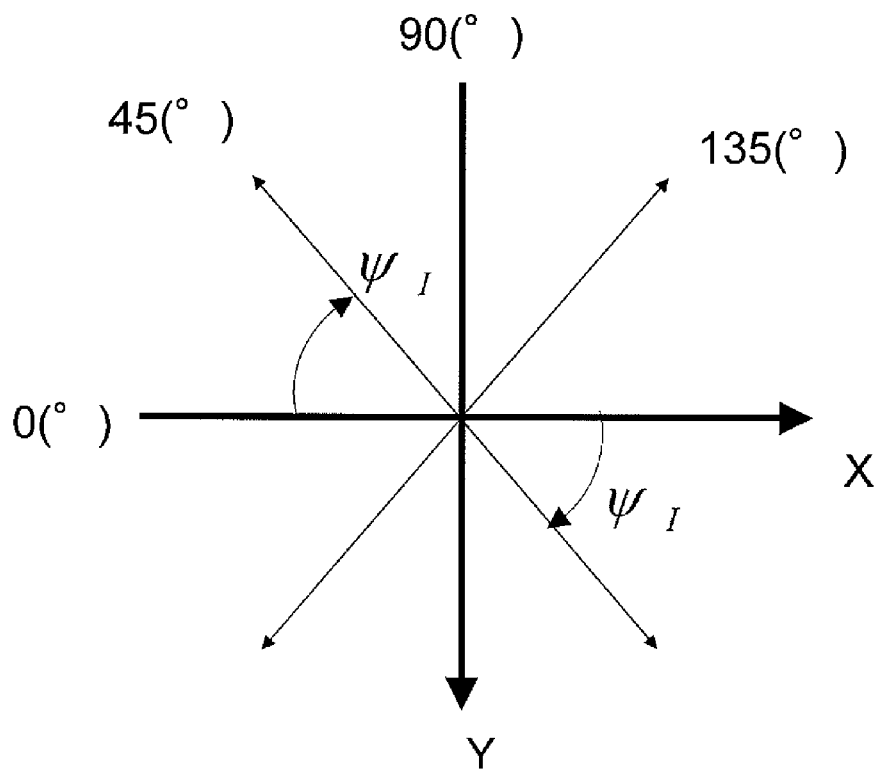
FIG. 3 shows how to define the angle of a plane of polarization.

FIG. 3 shows how the plane of polarization of polarized light source has its angle ψI defined. As described above, an X-Y coordinate system is defined with respect to the object.

In this case, the angle ψI of the plane of polarization is defined as shown in FIG. 3 with the X-axis direction set to be 0 degrees. If the angle ψI is saved for reflected light, then the respective planes of polarization of the reflected light and the incident light will have the same angle. And if the angle ψI of the plane of polarization is going to be increased or decreased, the same polarization state will recur over and over again in a period of 180 degrees. That is to say, a function that uses the angle ψI of the plane of polarization as a variable is a periodic function that has a period of 180 degrees. In this description, the angle ψI of the plane of polarization of polarized light source will be sometimes referred to herein as an "incident plane of polarization angle".

Figure 4A:
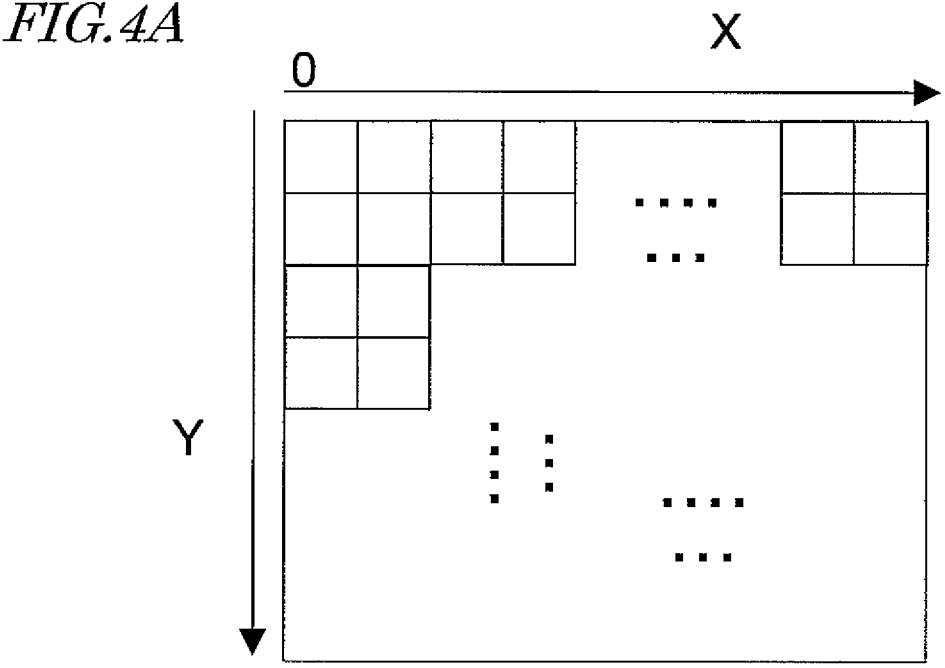
FIGS. 4A and 4B illustrate an exemplary arrangement of photosensitive cells in an image sensor for use in the first embodiment of the present disclosure.
Figure 4B:
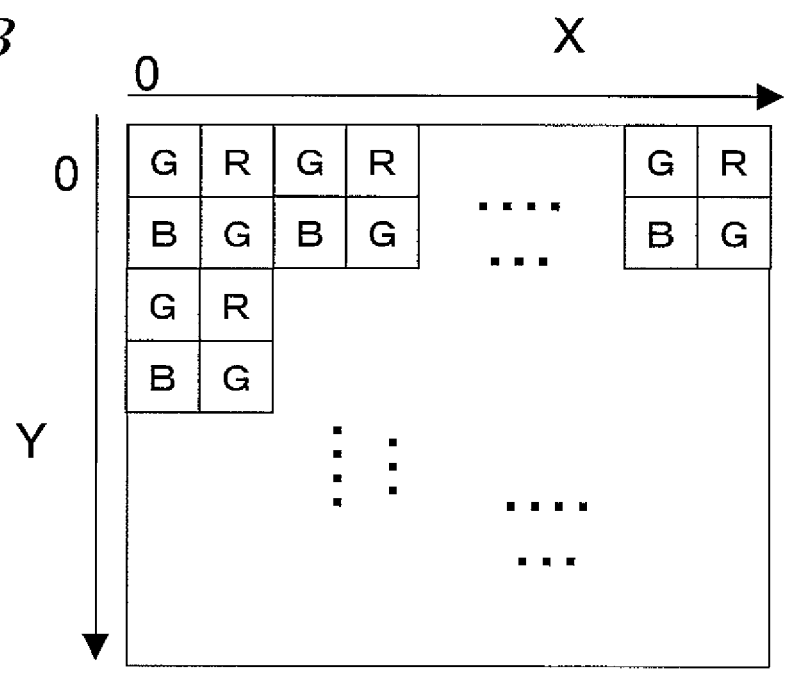

FIGS. 4A and 4B illustrate an exemplary arrangement for the image capturing plane of the image sensor 110. As shown in FIG. 4A, a number of photosensitive cells (i.e., photodiodes) are arranged regularly in columns and rows (i.e., in X-Y directions) on the image capturing plane. When a color image is going to be captured, color mosaic filters, which transmit light rays with three different wavelengths associated with RGB, are arranged as shown in FIG. 4B. Each of these photosensitive cells generates, by photoelectric conversion, an electrical signal representing the quantity of the light received. For this part, an ordinary single-panel color image sensor may be used. In this manner, a known image sensor to capture a light intensity image may be used as the image sensor 110. In this embodiment, if the illumination is plane polarized light, an image is captured with its plane of polarization rotated, thereby obtaining information about the object's surface. If a polarization mosaic photodiode is used to capture a polarization image as disclosed in Japanese Laid-Open Patent Publication No. 2009-246770 and Japanese Laid-Open Patent Publication No. 2010-104424, some artifact such as a moiré pattern is often produced on the polarization image. According to this embodiment, however, such a factor in debased image quality can be eliminated, which is beneficial.

Next, it will be described what kind of light intensity variation will be produced when the plane of polarization of the polarized light source is rotated.

Figure 6:
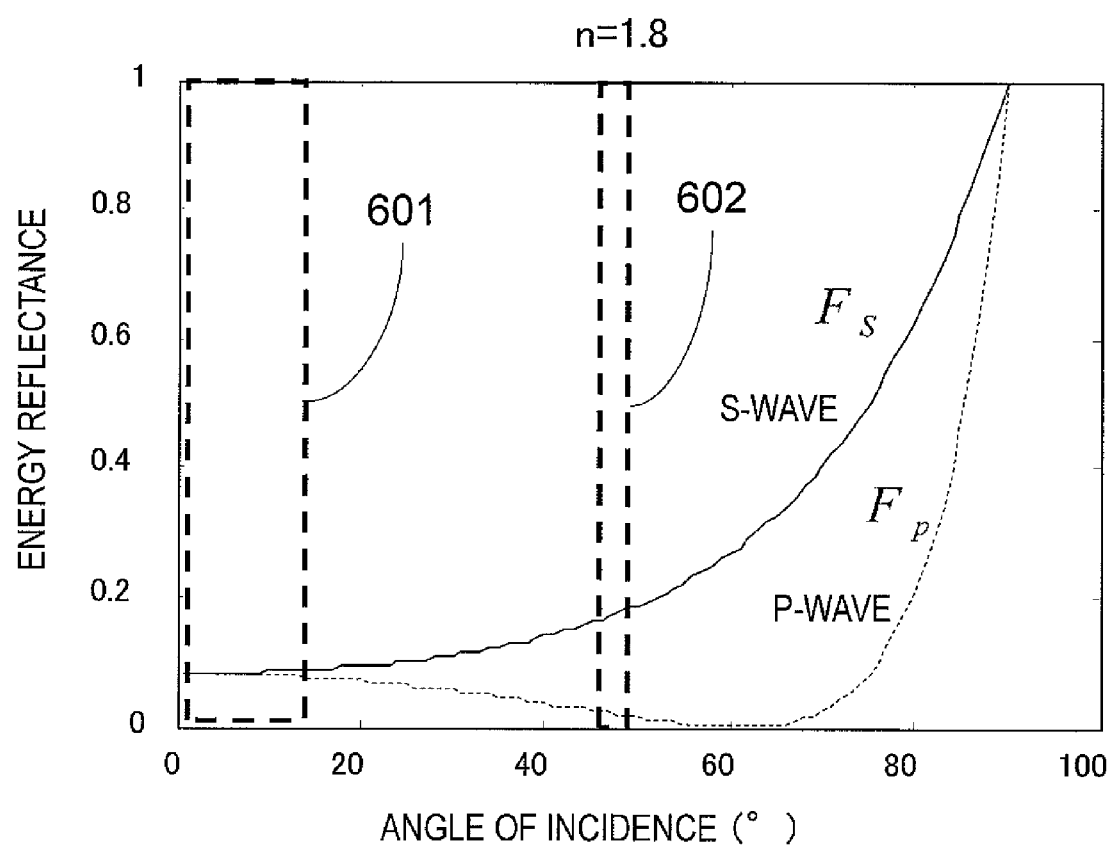
FIG. 6 is a graph showing how the Fresnel reflectances of P- and S-wave energies change with the angle of incidence (that is represented as the abscissa).

FIG. 5 illustrates how polarized light is incident on the surface 801 at an angle of incidence that is close to zero degrees and how the specular reflected light is observed with a camera. The respective angles defined by the polarization planes of the incident polarized light are different from each other by 90 degrees between portions (a) and (b) of FIG. 5. However, even though the reflected plane polarized light travels in a different direction from the incident light, the intensity (i.e., the energy) of the reflected light is almost the same as that of the incident light for the following reasons:

FIG. 6 is a graph showing the dependence of the specular reflectance according to the Fresnel theory on the angle of incidence. In FIG. 6, the abscissa represents the angle of incidence and the ordinate represents the Fresnel reflectance. These dependence curves are drawn on the supposition that the refractive index n is 1.8. The angles of incidence of around 0 through around 15 degrees, which can be regarded as representing substantially perpendicular incidence, fall within the range 601. As can be seen from this graph, both P and S waves have substantially the same reflectance in this range 601. Therefore, if the polarized light is incident substantially perpendicularly onto the surface, then it makes almost no difference for the surface and the light is reflected in the same behavior, no matter whether the polarized light is actually a P-wave or an S-wave. That is to say, the polarization state of the returning light becomes the same as that of the incident light. Consequently, the intensity of the returning light does not vary with a change of the plane of polarization. This fact is satisfied extensively by any natural object with a refractive index n of 1.4 to 2.0.

As described above, if polarized light is incident on a smooth surface at an angle of incidence of almost zero degrees, reflected once and then observed, the energy of the reflected light does not change, and the intensity Y observed does not change, either, even when the plane of polarization of the polarized light is rotated by ψI degrees.

Figure 7:
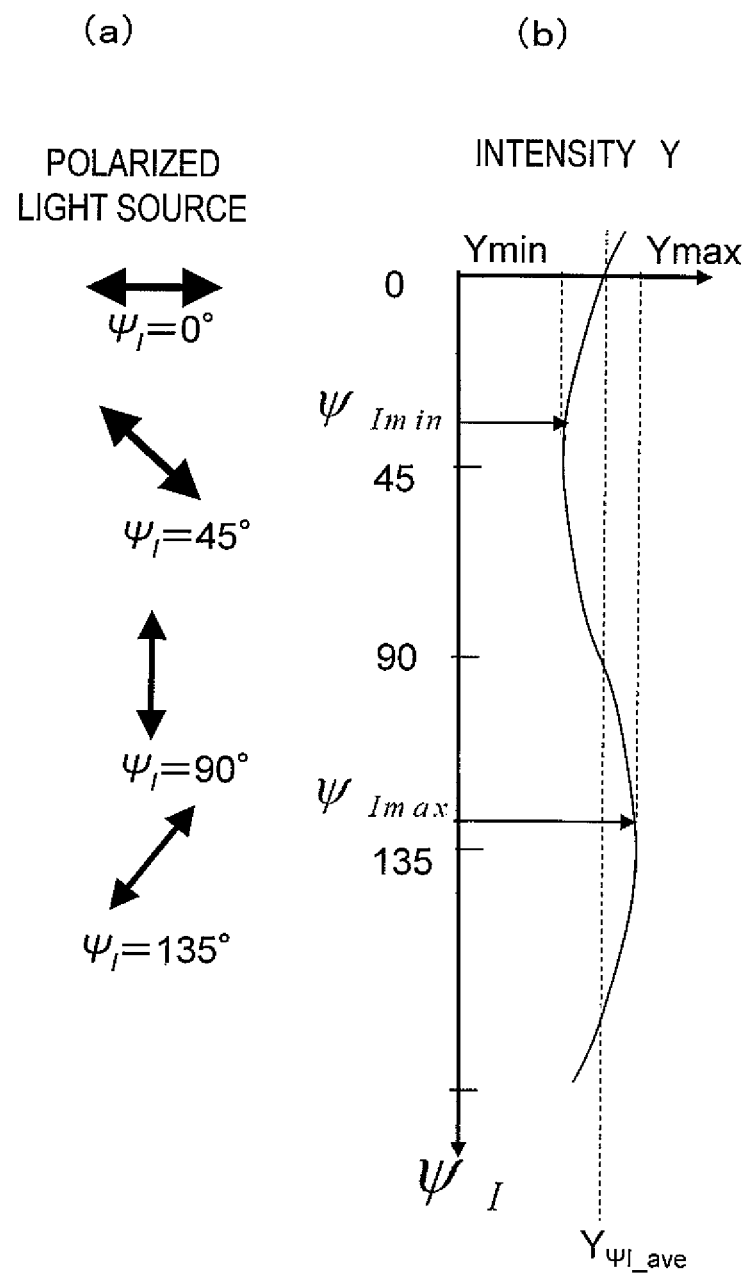
FIG. 7 shows how the intensity value of a pixel varies as the plane of polarization of polarized light is rotated.

FIG. 7 shows the behavior of the intensities Y of a particular pixel of a light intensity image that were obtained when the plane of polarization of the polarized light defined angles ψI of 0, 45, 90 and 135 degrees, respectively, with respect to a surface with unevenness. As can be seen from this graph, on such an uneven surface, the intensity Y varied periodically according to the angle ψI of the plane of polarization of each polarized light. The reason will be described in detail below.

Figure 8A:
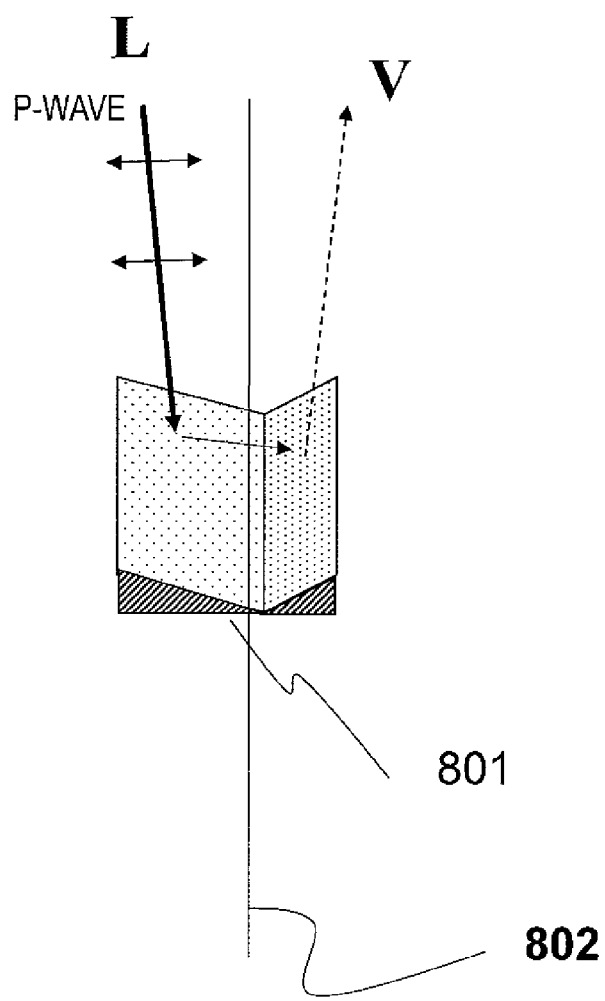
FIGS. 8A and 8B illustrate how the intensity of a polarized reflected light ray varies when the light ray is reflected twice.
Figure 8B:
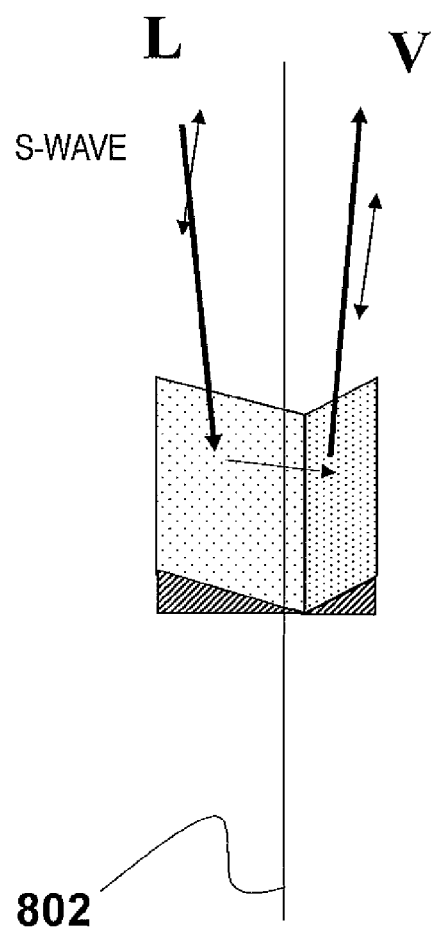

FIGS. 8A and 8B illustrate how a groove 801 that has been formed on a surface with unevenness produces reflection twice on its slopes. That kind of multiple reflection would be always produced on an uneven surface of various objects. In this case, the properties of reflections are important the first and second times around. Depending on the geometric arrangement, it is not impossible that multiple reflection is produced for the third time at the same position as the second time around. However, as this is a very rare case scenario, only a situation where the multiple reflection occurs twice will be considered in the following description.

Generally speaking, if the properties of reflection are roughly classified into specular reflection and diffuse reflection, there should arise one of the following four situations:

1) diffuse reflection the $1^{st}$ time around and specular reflection the $2^{nd}$ time around;
2) diffuse reflection both of the $1^{st}$ and $2^{nd}$ times around;
3) specular reflection the $1^{st}$ time around and diffuse reflection the $2^{nd}$ time around; and
4) specular reflection both of the $1^{st}$ and $2^{nd}$ times around.

However, the present inventors confirmed via experiments that if the object has a smooth surface, then situation 4) in which light is specular reflected for both of the $1^{st}$ and $2^{nd}$ times around may be regarded as a common phenomenon.

As shown in FIG. 8A, polarized light incident perpendicularly to the main axis direction 802 of the groove is a P-wave. Look at FIG. 6 again, and it can be seen that if the object's groove has a tilt angle of approximately 45 degrees and if light is incident from right over the groove, the reflectance of a P-wave becomes much lower than that of an S-wave in the range 602 of that angle of incidence as can be seen from the graph showing the Fresnel reflectance. The reflectance of the P-wave further decreases as the P-wave goes through reflection first and second times around. On the other hand, the S-polarized light shown in FIG. 8B does not have its reflectance decreased so much even after having gone through the reflections first and second times around. As a result, on the plane of polarization of the P-wave that has been incident on the groove, the reflected light comes to have very low energy and decreased intensity. On the other hand, on the incident plane of polarization of the S-wave, the reflected light has not had its energy attenuated so much and still maintains high intensity.

If the surface groove is supposed to be as such, the variation in the intensity of the reflected light that was caused by rotating the plane of polarization of the incident light in an experiment can be accounted for.

The reflections from the groove first and second times around can be detected as a polarization phenomenon and can be observed as a light intensity variation using a rotating polarized light source. However, the groove model described above is a somewhat artificial groove. The unevenness on the surface or an organism's organ or mucosa actually has various shapes. Models of such actual grooves are illustrated in FIGS. 9 through 12.

FIGS. 9A and 9B illustrate a groove in the simplest shape. Such a groove consists of only two slopes 901 and light that has been incident there from substantially right over such a groove is reflected twice from those slopes (as indicated by the arrow 902) to be returning light. In this model, only the two-step reflection phenomenon occurs in the groove. That is why in a situation where the resolution is low to a certain degree, the middle of the groove often becomes darker than anywhere else, and therefore, the unevenness can be detected even by known intensity-based image processing.

In any of the following shapes, however, incoming light is reflected only once somewhere but is reflected twice elsewhere, thus making it difficult to sense the unevenness on a light intensity basis.

Figure 10A:
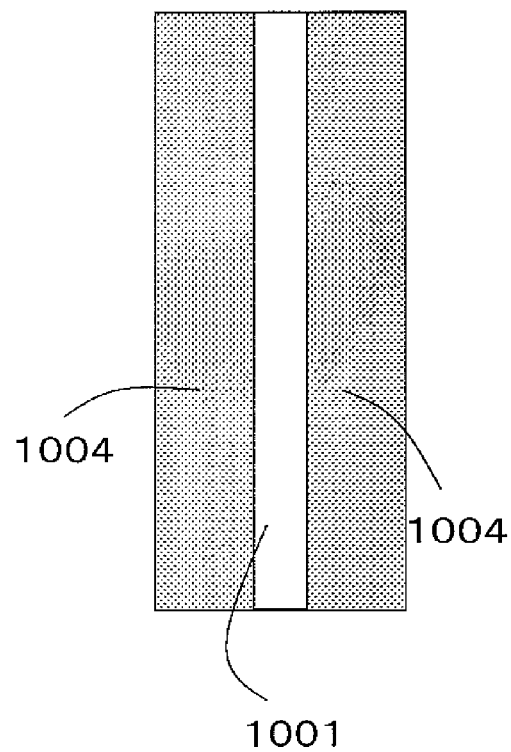
FIG. 10A illustrates the shape of a groove with a bottom and slopes and FIG. 10B illustrates how incoming light is reflected from it.
Figure 10B:
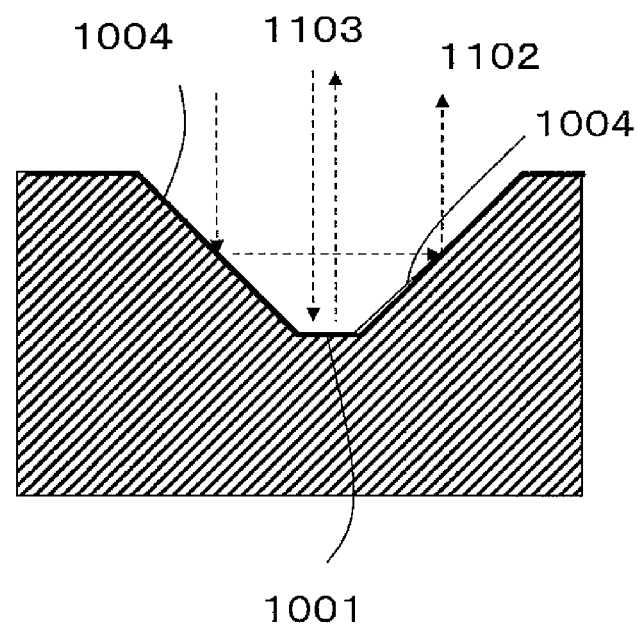

FIGS. 10A and 10B illustrate a situation where the groove has a bottom 1001 and has a shape to be often observed in a shallow and broad recessed portion. In that case, the light that has been incident from right over the groove is not only reflected twice from the slope 1004 to be returning light (as indicated by the arrow 1002) but also reflected once from the bottom (as indicated by the arrow 1103). That is why if such a groove is observed on a light intensity basis, the middle of the groove will look brightest and the recessed portion will look darker than its surrounding regions contrary to the common conception. Consequently, it is difficult to sense the unevenness through the intensity-based image processing.

Figure 11A:
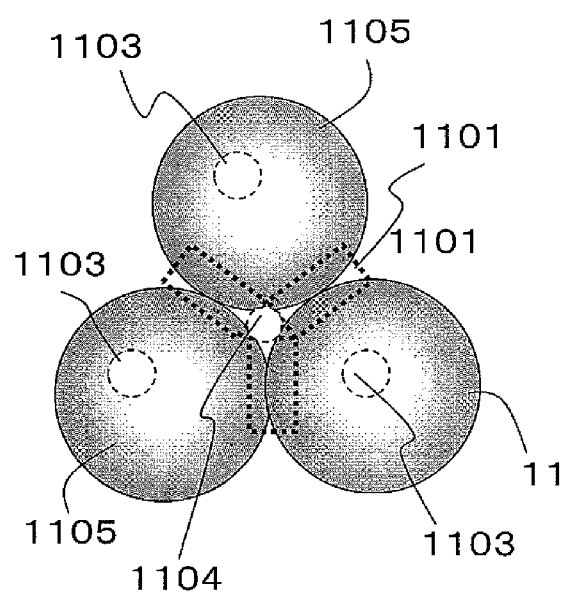
FIG. 11A illustrates a shape in which raised portions (elevated portions) are arranged densely and FIG. 11B illustrates how incoming light is reflected from it.
Figure 11B:
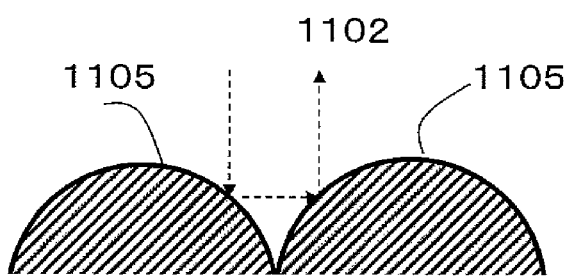

FIGS. 11A and 11B illustrates the shape of a region in which raised portions 1105 are arranged densely on a flat portion. This is a shape in a situation where raised tumors have been produced. In FIGS. 11A and 11B, those raised portions are illustrated as a hemispherical model for the sake of simplicity. The gap 1101 between the raised portions 1105 can be regarded as a recessed portion. As shown in FIG. 11B, the light that has been incident there from substantially right over this region is reflected twice from two adjacent surfaces to be returning light (as indicated by the arrow 1102).

Although the incoming light is reflected once from each of those raised portions to make the intensity very high, the recessed portion located in their gap also has a region 1104, from which the light is reflected only once, at the bottom. And that region 1104 often has a very high intensity. That is why if the observation is made on a light intensity basis, the recessed portion will look brighter than its surrounding portions. As a result, it is difficult to detect the recessed portion such as the one shown in FIGS. 11A and 11B accurately by sensing the unevenness on a light intensity basis.

Figure 12A:
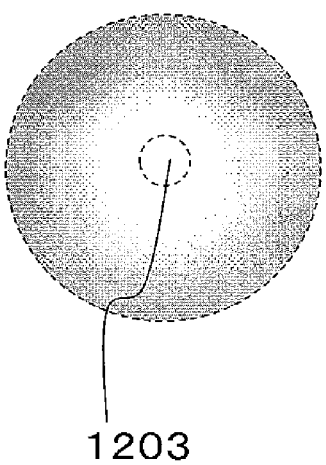
FIG. 12A illustrates the shape of a hole (recessed portion) and FIG. 12B illustrates how incoming light is reflected from it.
Figure 12B:
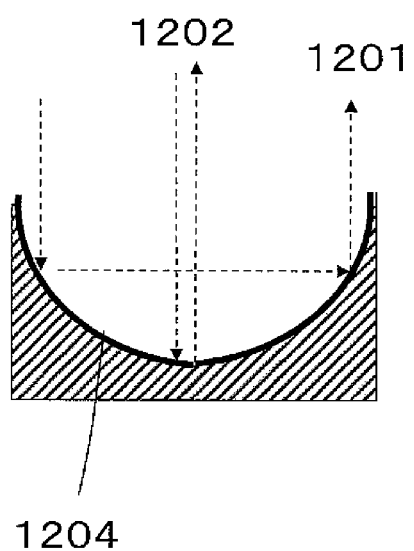

FIGS. 12A and 12B illustrate the shape of a region in which there is a single hole recessed portion 1204 by itself on a flat portion. The recessed portion 1204 is illustrated as a hemispherical model. In this case, as there are also a pair of slopes that face each other, the light that has been incident there from substantially right over this region is also reflected twice to be returning light (as indicated by the arrow 1201). Meanwhile, the incoming light is reflected once from the bottom as indicated by the arrow 1202. That is why if observation is made on a light intensity basis, then the center 1203 of the recessed portion 1204 will look brightest. As a result, the recessed portion 1204 looks brighter than its surrounding portions contrary to the common conception, and therefore, it is difficult to accurately detect the recessed region such as the one shown in FIGS. 12A and 12B by sensing the unevenness on a light intensity basis.

According to this embodiment, even when the given object has any of various shapes that make it difficult to obtain unevenness information by the intensity-based image processing, surface unevenness information can be detected accurately by distinguishing the once-reflected phenomenon from the twice-reflected phenomenon by reference to the information that has been collected with a rotating polarized light source.

Figure 13:
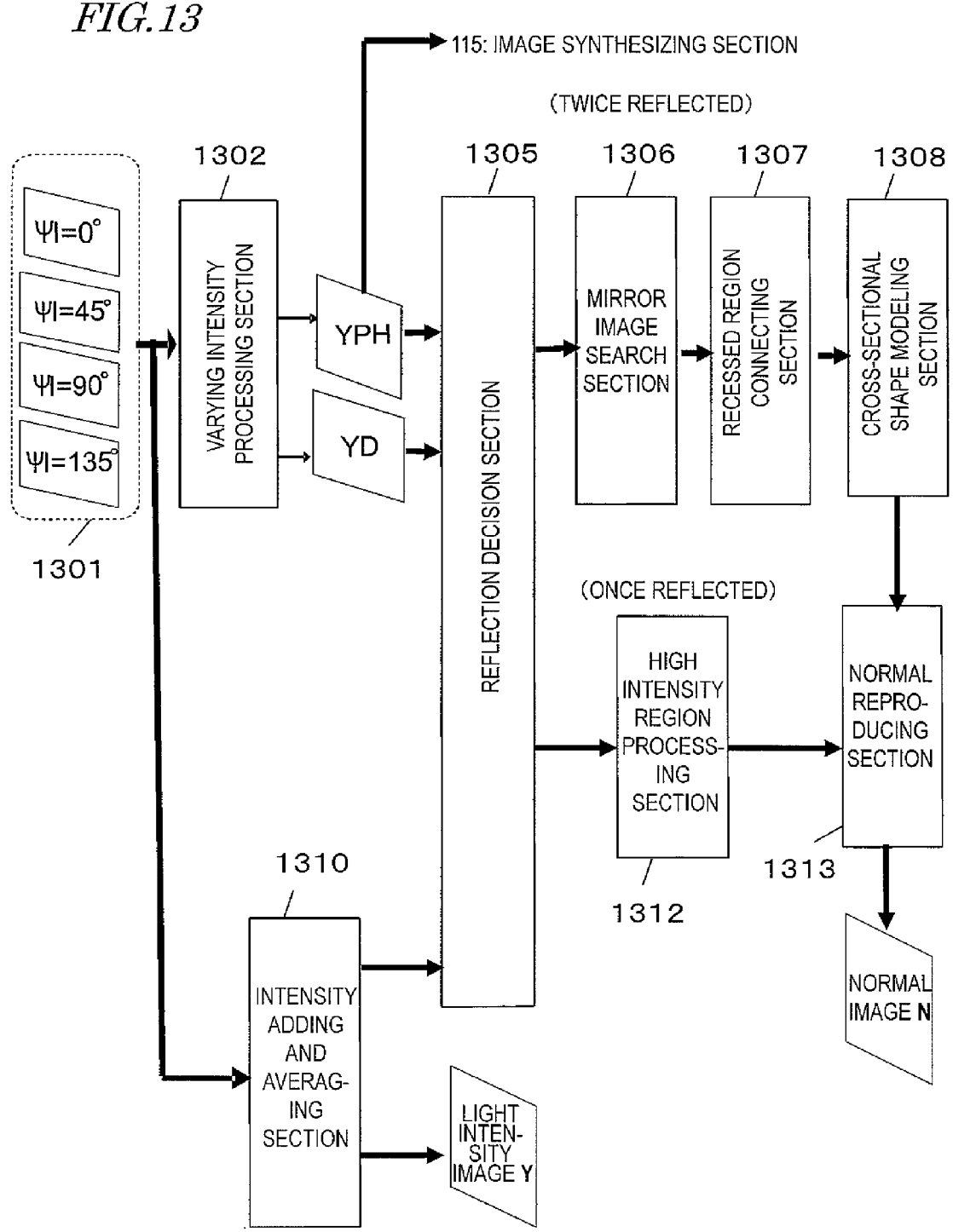
FIG. 13 is a block diagram illustrating configuration for an image processing processor according to the first embodiment of the present disclosure.

FIG. 13 is a block diagram illustrating a configuration for the image processing processor 108. In this embodiment, the image processing is carried out based on the principle of sensing the unevenness by reference to the information that has been obtained by monitoring an intensity variation with the object irradiated with a polarized light source with a rotating plane of polarization. A group 1301 of four light intensity images that have been captured with the plane of polarization angles $\psi I$ of the light changed from 0 degrees into 45, 90 and 135 degrees is input to this image processing processor 108.

The intensity variation in a situation where the plane of polarization of polarized light is rotated becomes a cosine function with a period of 180 degrees. Thus, the varying intensity processing section 1302 optimum-fits the intensity variation to the cosine function. The intensity variation can be given by the following Equation (7) where $\psi I$ denotes the angle of the plane of polarization of the light:

$$Y(\psi_I) = Y_{\psi I\_ave} + A_I \cos(2(\psi_I - \psi_0)) \tag{1}$$

Figure 14:
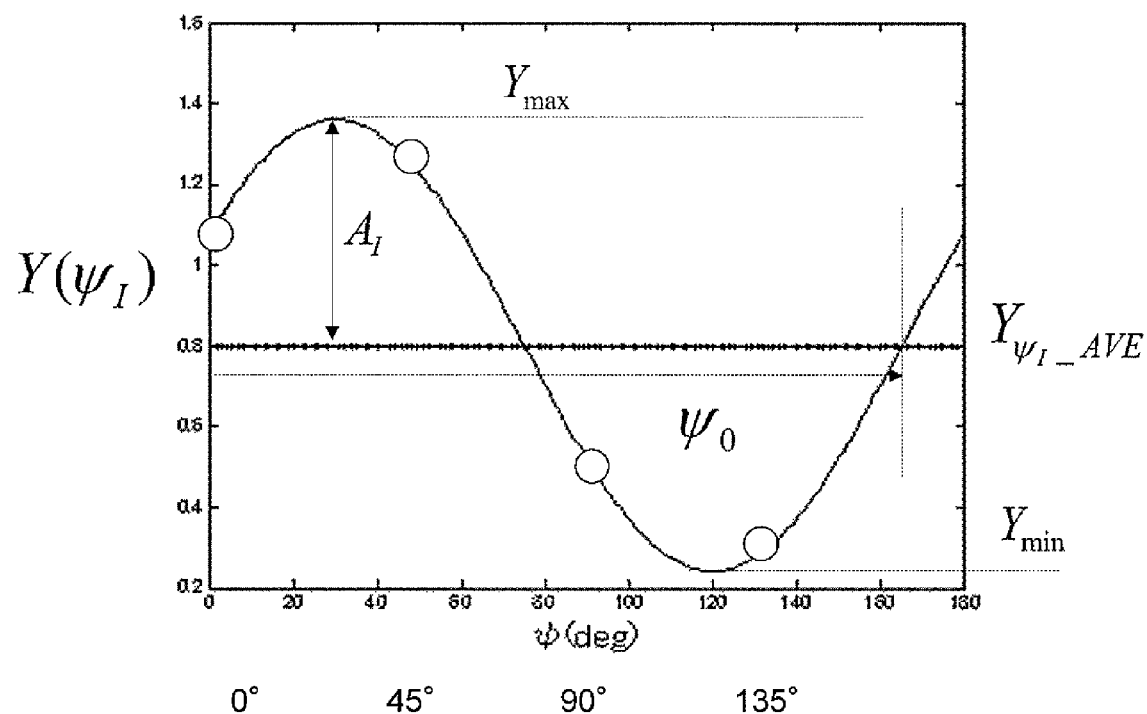
FIG. 14 shows how to fit a cosine function based on samples of the polarized light intensities of four different kinds of polarized light sources.

FIG. 14 shows the cosine function of this intensity variation and indicates the meanings of the amplitude $A_I$, the phase $\psi_0$ and the average $Y\psi_{I\_ave}$ described above. The four sample points are plotted right on that cosine function for the sake of simplicity. These values can be estimated by fitting the cosine function based on the four angular samples that have been obtained at regular intervals in the following manner. First of all, the intensity $Y\psi_{I\_ave}$ of the original image under non-polarized light is calculated by the following Equation (8). This approximately reproduces the light intensity image under the non-polarized light and can usually be used as an image normally observed with an endoscope:

$$Y_{\psi I\_AVE} = \tag{2}$$
$$\frac{1}{4}(Y(\psi_I = 0°) + Y(\psi_I = 45°) + Y(\psi_I = 90°) + Y(\psi_I = 135°)) \approx$$
$$\frac{1}{2}(Y_{max} + Y_{min})$$

The varying intensity processing section 1302 carries out optimum fitting from the sampled intensities to the cosine function using a minimum mean square error. In this case, the optimum fitting process is begun by carrying out sampling in the four directions that are defined by 0, 45, 90 and 135 degrees, respectively. Since the cosine function is determined by the three kinds of information that are amplitude, phase and average, the number of samples for use to determine the cosine function does not have to be four but may actually be any other number as long as the number is at least three. Nevertheless, if samples are taken at a regular interval of 45 degrees in this manner, the optimum fitting can be simplified.

First of all, the square error E of the intensities $I_0$, $I_1$, $I_2$ and $I_3$ at the polarization angles of 0, 45 ($=\pi/4$), 90 ($=\pi/2$) and 135 ($=3\pi/4$) degrees is defined by the following Equation (3):

$$E = (Y(\psi_I = 0) - I_0)^2 + \left(Y\left(\psi_I = \frac{\pi}{4}\right) - I_1\right)^2 + \qquad (3)$$

$$\left(Y\left(\psi_I = \frac{\pi}{2}\right) - I_2\right)^2 + \left(Y\left(\psi_I = \frac{3\pi}{4}\right) - I_3\right)^2 =$$

$$(Y_{\psi I\_AVE} + A_I \cos(2\psi_O) - I_0)^2 + (Y_{\psi I\_AVE} + A_I \sin(2\psi_O) - I_1)^2 +$$

$$(Y_{\psi I\_AVE} - A_I \cos(2\psi_O) - I_2)^2 + (Y_{\psi I\_AVE} - A_I \sin(2\psi_O) - I_3)^2$$

The phase $\psi_O$ of the cosine function that minimizes this square error can be calculated by the following Equation (4):

$$\frac{\partial E}{\partial \psi_O} = 4A_I[(I_3 - I_1)\cos(2\psi_O) + (I_0 - I_2)\sin(2\psi_O)] = 0 \qquad (4)$$

Based on this equation, the solutions can be given by the following Equations (5) and (6):

$$\begin{cases} \psi_O^{(+)} = \frac{1}{2}\cos^{-1}\left(\sqrt{\frac{c^2}{a^2 + c^2}}\right) \\ \psi_O^{(-)} = \frac{1}{2}\cos^{-1}\left(-\sqrt{\frac{c^2}{a^2 + c^2}}\right) \end{cases} \qquad (5)$$

$$\begin{cases} a \equiv (I_3 - I_1) \\ c \equiv (I_0 - I_2) \end{cases} \qquad (6)$$

A mathematical function such as an inverse trigonometric function generally imposes the following constraint:

$$0 \geq a \cos(x) \leq \pi \qquad (7)$$

Considering this angular range, by making classification based on the magnitudes of a and c, the respective angles at which the maximum and minimum values are obtained can be calculated by the following Equations (8):

$$\begin{cases} \text{if } a < 0 \text{ and } c > 0, \psi_{Omin} = \frac{\pi}{2} + \psi_O^{(+)} \ \psi_{Omax} = \psi_O^{(+)} \\ \text{if } a < 0 \text{ and } c < 0, \psi_{Omin} = \frac{\pi}{2} + \psi_O^{(-)} \ \psi_{Omax} = \psi_O^{(-)} \\ \text{if } a > 0 \text{ and } c < 0, \psi_{Omin} = \psi_O^{(+)} \ \psi_{Omax} = \frac{\pi}{2} + \psi_O^{(+)} \\ \text{if } a > 0 \text{ and } c > 0, \psi_{Omin} = \psi_O^{(-)} \ \psi_{Omax} = \frac{\pi}{2} + \psi_O^{(-)} \end{cases} \qquad (8)$$

The $\psi_{Omax}$ value at which the maximum value is obtained can be used as it is as the intensity maximizing angle image YPH:

$$YPH = \psi_{Omax} \qquad (9)$$

Next, the maximum and minimum values of the amplitude are obtained. First of all, to obtain the amplitude $A_I$, the square error is minimized by the following Equation (10):

$$\frac{\partial E}{\partial A_I} = 0 \qquad (10)$$

Using the amplitude $A_I$, the maximum and minimum values of the amplitude are calculated by the following Equations (11):

$$Y_{max} = Y_{\psi I\_AVE} + A_I \qquad (11)$$

$$Y_{min} = Y_{\psi I\_AVE} - A_I$$

$$A_I = \frac{1}{2}[(I_0 - I_2)\cos(2\psi_O) - (I_3 - I_1)\sin(2\psi_O)]$$

Thus, if the maximum and minimum values Ymax and Ymin of the amplitude given by these Equations (11) are used, the degree of intensity modulation image YD can be given by the following Equation (12):

$$YD = \frac{Y_{max} - Y_{min}}{Y_{max} + Y_{min}} \qquad (12)$$

Normal optimum fitting to a cosine function can be carried out on three or more samples and its method is disclosed in Japanese Patent No. 4235252, for example.

By performing these processing steps, the intensity maximizing angle image YPH and the degree of intensity modulation image YD can be obtained. These pieces of information are then provided for a reflection decision section 1305 as shown in FIG. 13. These two kinds of images, namely, the intensity maximizing angle image YPH and the degree of intensity modulation image YD, are often collectively called "pseudo-color images". In that case, it is the intensity maximizing angle image YPH that represents the hue angle of the color and it is the degree of intensity modulation image YD that represents the saturation of the color.

As also shown in FIG. 13, the group 1301 of images that have been shot under different polarized light sources are added together, and their average is calculated, by an intensity adding and averaging section 1310 and become equivalent to an image that has been shot under a non-polarized light source. And this becomes a light intensity image Y that functions as a normal color image.

Using the intensity maximizing angle image YPH, the degree of intensity modulation image YD, and the light intensity image Y, the reflection decision section 1305 decides whether the light has been reflected from the object's surface only once or twice.

Figure 15:
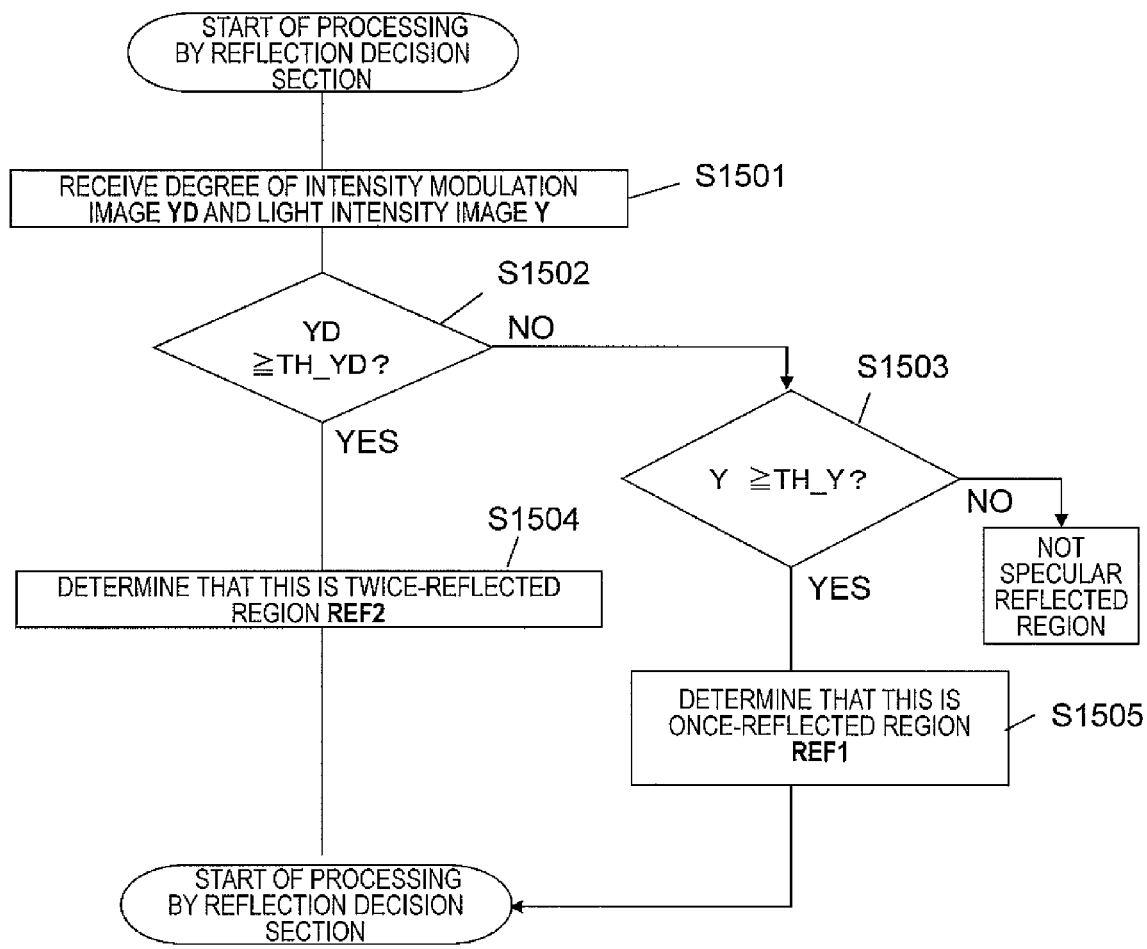
FIG. 15 is a flowchart showing the procedure of processing to be performed by a reflection decision section to decide whether the incoming light has been reflected once or twice.

FIG. 15 is a flowchart showing the procedure of the processing carried out by the reflection decision section 1305.

First, in Step S1501, the reflection decision section 1305 receives the degree of intensity modulation image YD and the light intensity image Y. Next, in Step S1502, the reflection decision section 1305 decides whether or not the value (i.e., the degree of modulation) of each pixel of the degree of intensity modulation image YD is equal to or greater than a predetermined threshold level TH_YD. Then, in Step S1504, the reflection decision section 1305 determines that (i) an image area (REF2=YES) consisting of pixels, of which the degrees of modulation are equal to or greater than the predetermined threshold level TH_YD, represents a twice-reflected region. On the other hand, the reflection decision section 1305 determines that (ii) an image area (REF2=No) consisting of pixels, of which the degrees of modulation are less than the predetermined threshold level TH_YD, represents a non-twice-reflected region. In this manner, only a reflected region, of which the degrees of intensity modulation are equal to or greater than the predetermined threshold level TH_YD, can be separated as a pixel region representing the twice-reflected region REF2.

$$REF2 = \begin{cases} \text{YES} & (YD \geq TH\_YD) \\ \text{NO} & (YD < TH\_YD) \end{cases} \quad (13)$$

In Step S1503, the reflection decision section 1305 decides whether the light intensity value Y of the area that has been determined to be REF2=No (i.e., non-twice-reflected region) in Step S1502 is greater than the predetermined threshold value TH_Y. If the light intensity value Y of the pixels is equal to or greater than the predetermined threshold value TH_Y (i.e., if REF1=YES in Equation (14)), then the reflection decision section 1305 determines that an area consisting of such pixels represents a once-reflected region REF1. The once-reflected region REF1 and the twice-reflected region REF2 form a "specular reflection region". The twice-reflected region REF2 could include a region from which light is reflected more than twice, and therefore, may be called a "multi-reflection region". On the other hand, if the light intensity value Y of the pixels is smaller than the predetermined threshold value TH_Y (i.e., if REF1=No in Equation (14)), then the reflection decision section 1305 determines that an area consisting of such pixels does not represent a specular reflection region.

$$REF1 = \begin{cases} \text{YES} & (Y \geq TH\_Y) \\ \text{NO} & (Y < TH\_Y) \end{cases} \quad (14)$$

By performing these processing steps, the once-reflected region REF1 and the twice-reflected region REF2 can be separated from each other on the image. Also, a region that is neither the once-reflected region REF1 nor the twice-reflected region REF2 is distinguished from the "specular reflection region".

Figure 16A:
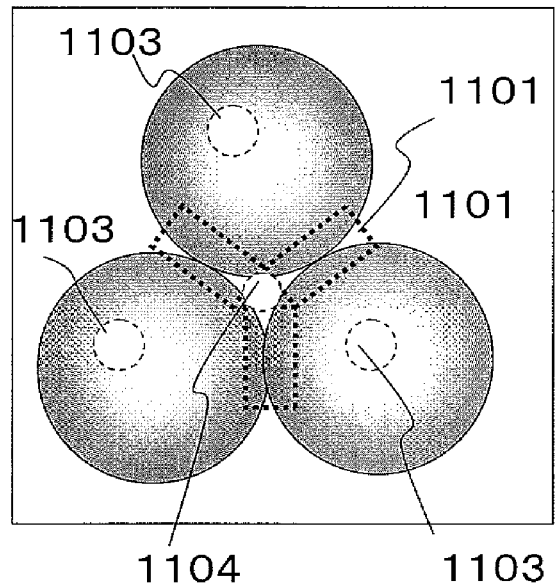
FIG. 16A illustrates the shape shown in FIG. 11 as a scene that has been shot.
Figure 16B:
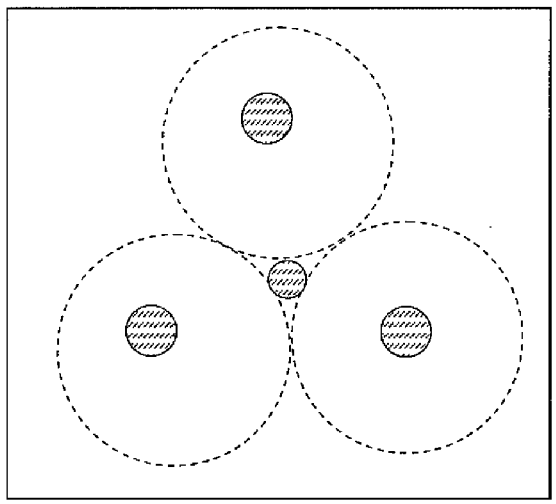
FIG. 16B schematically illustrates once-reflected regions REF1 separated.
Figure 16C:
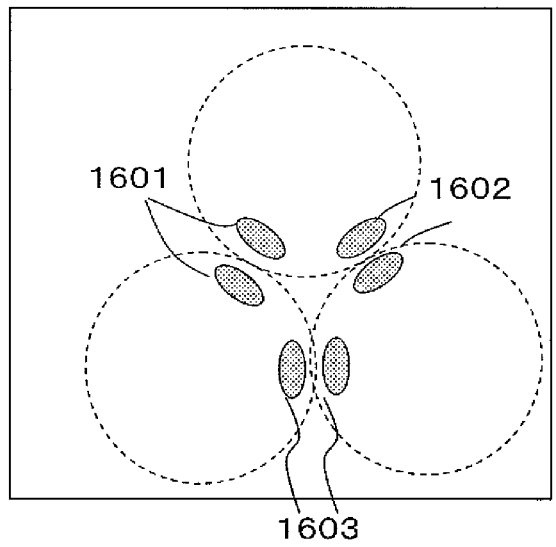
FIG. 16C schematically illustrates twice-reflected regions REF2 separated.

FIG. 16A schematically illustrates a result of the processing that has been performed by the reflection decision section 1305 on a scene in which raised portions such as tumors have been produced on a flat portion (see FIGS. 11A and 11B). In FIG. 16B, the once-reflected regions are illustrated as hatched circular areas. Each of those once-reflected regions is a high intensity region that is located around the top of the raised portion and at the bottom of the recessed portion. As shown in FIG. 16C, each pair of twice-reflected regions 1601, 1602 and 1603 is located on the slopes of the recessed portion in which the raised portions contact with each other.

Figure 17A:
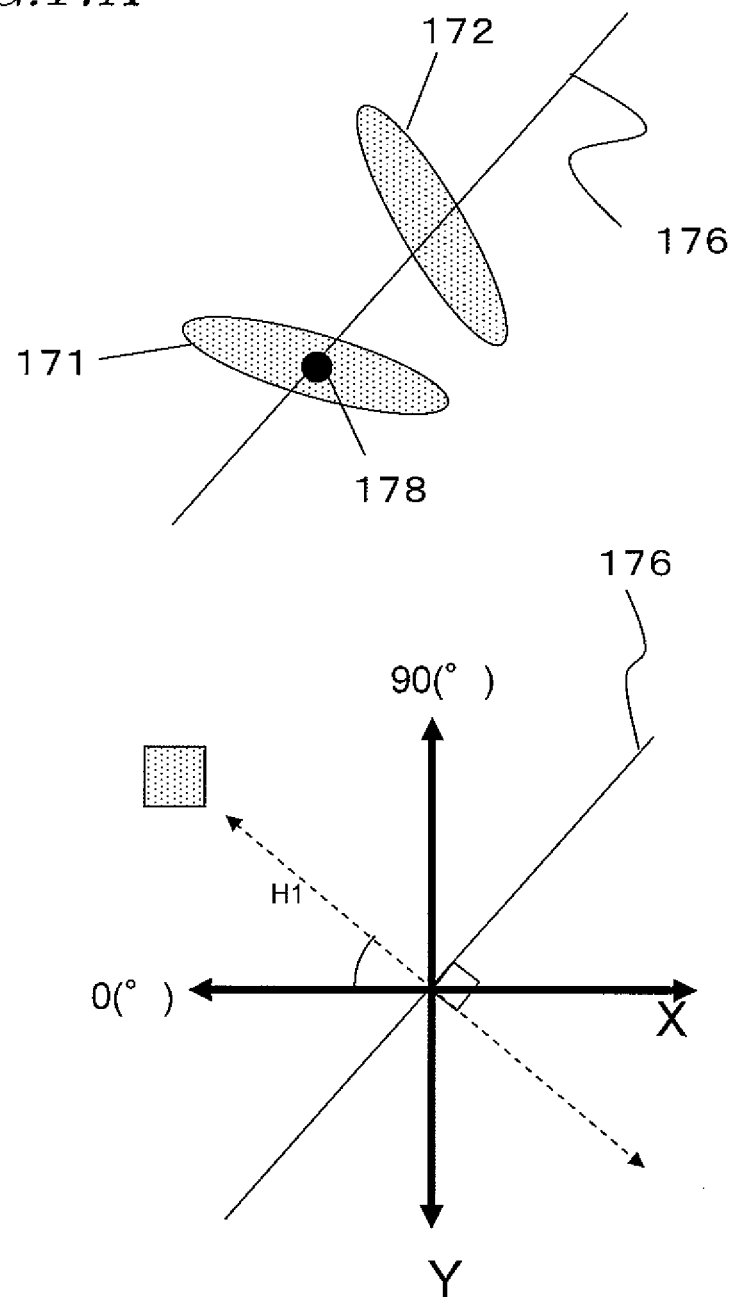
FIG. 17A illustrates how a mirror image search section performs its processing.

FIGS. 17A and 17B further represent this result of processing schematically. As shown in FIGS. 17A and 17B, micro-reflected regions 171, 172, 173, 174 and 175 of various shapes that have been separated and extracted each have the intensity maximizing angle H as their attribute.

The intensity maximizing angle H has a period of 180 degrees. In FIGS. 17A and 17B, regions with the same intensity maximizing angle H are represented with a pattern texture. Specifically, the regions 171 and 172 shown in FIG. 17A are supposed to have an attribute corresponding to an angle H1, while the regions 173, 174 and 175 shown in FIG. 17B are supposed to have an attribute corresponding to an angle H2. In other words, the intensity maximizing angle H of the regions 171 and 172 is supposed to be H1 and that of the regions 173, 174 and 175 is supposed to be H2.

In performing the mirror image search to be described below, first of all, a recessed portion is located by finding the twice-reflected regions 1601, 1602 or the region 1603 with a pair of mirror images as shown in FIG. 16C. When the pair of regions 171 and 172 shown in FIG. 17A is going to be found, their shapes as binary images have too low a degree of reliability to be very much useful. However, the angle H1 that these twice-reflected regions have becomes an important clue. The reason is that as the angle H1 represents the groove principal axis angle, those regions that form a pair should be present in the direction that intersects with the groove principal axis at right angles. The search may be carried out only on a line that crosses that groove principal axis at right angles. Such a line will be referred to herein as a "search line 176". For example, the search line 176 drawn with respect to the region 171 shown in FIG. 17A is a line that passes through the barycenter 178 of the region 171 and that crosses the line defining the angle H1 at right angles. In the example illustrated in FIG. 17B, a mirror image corresponding to the region 173 is present on the line that passes through the barycenter of the region 173 and that crosses the line defining the angle H2 at right angles (i.e., located on the search line 177). That is why the mirror image corresponding to the region 173 may be found just by making a search on the search line 177. In the example illustrated in FIG. 17B, a region 175, of which the angle is equal to the angle value H2, is located in the vicinity of the region 173 but is not present on the search line 177. That is to say, these regions 173 and 175 do not form a pair of twice-reflected regions. According to such a method in which a search is made on a search line, the region 175 is not taken for a region that forms a pair with the region 173.

Figure 18A:
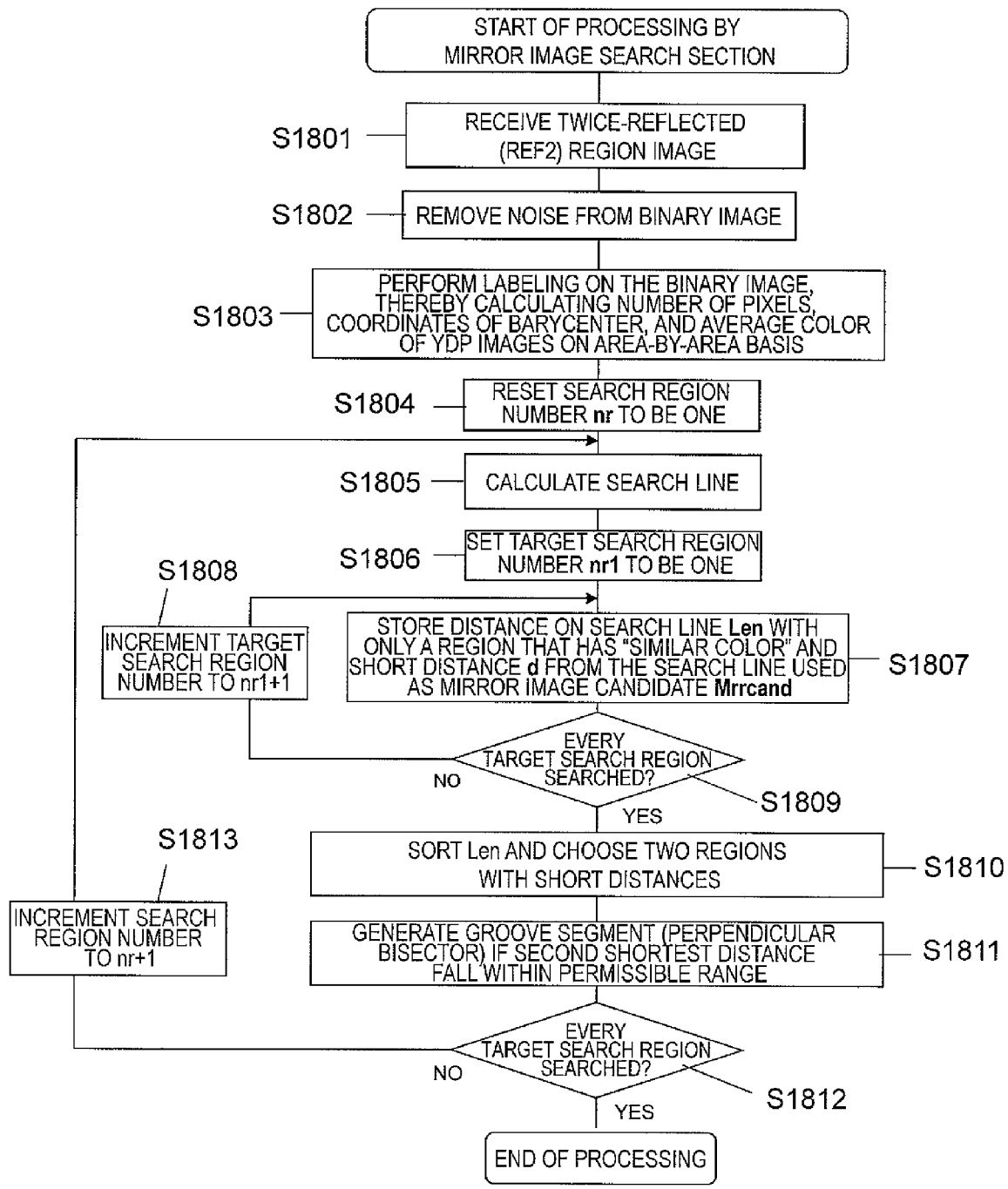
FIG. 18A is a flowchart showing the procedure of processing to be performed by the mirror image search section.

Hereinafter, it will be described with reference to FIG. 18A what processing is carried out by the mirror image search section 1306. FIG. 18A is a flowchart showing an exemplary procedure of the processing to get done by the mirror image search section 1306.

First of all, in Step S1801, the mirror image search section 1306 receives a twice-reflected region image, which is data including a binary image representing a pair of twice-reflected regions such as the one shown in FIG. 16C, the intensity maximizing angle image YPH and the degree of intensity modulation image YD. Specific examples of such data will be described later with reference to FIG. 18B. In the following description, the intensity maximizing angle value of each of the pixels that form the intensity maximizing angle image YPH will be referred to herein as a "YPH value" and the degree of modulation of each of the pixels that form the degree of intensity modulation image YD will be referred to herein as a "YD value".

Next, in Step S1802, the mirror image search section 1306 removes, as noise, finely scattered very small regions that have been generated on the image as a result of the binarization processing done by the reflection decision section 1305 (which has already been described with respect to Equation (13)). To do that, ordinary binary image zoom in and zoom out processing just needs to be carried out.

Subsequently, in Step S1803, the mirror image search section 1306 performs labeling on the binary image, thereby calculating the number of pixels, the coordinates of the barycenter, and the averages of the YD and YPH values on an area-by-area basis. In this processing step, to calculate the averages of the YD and YPH values, pseudo color values (R, G, B), which are represented by using the YD value as a color saturation and the YPH value as a color hue, are used.

Figure 18B:
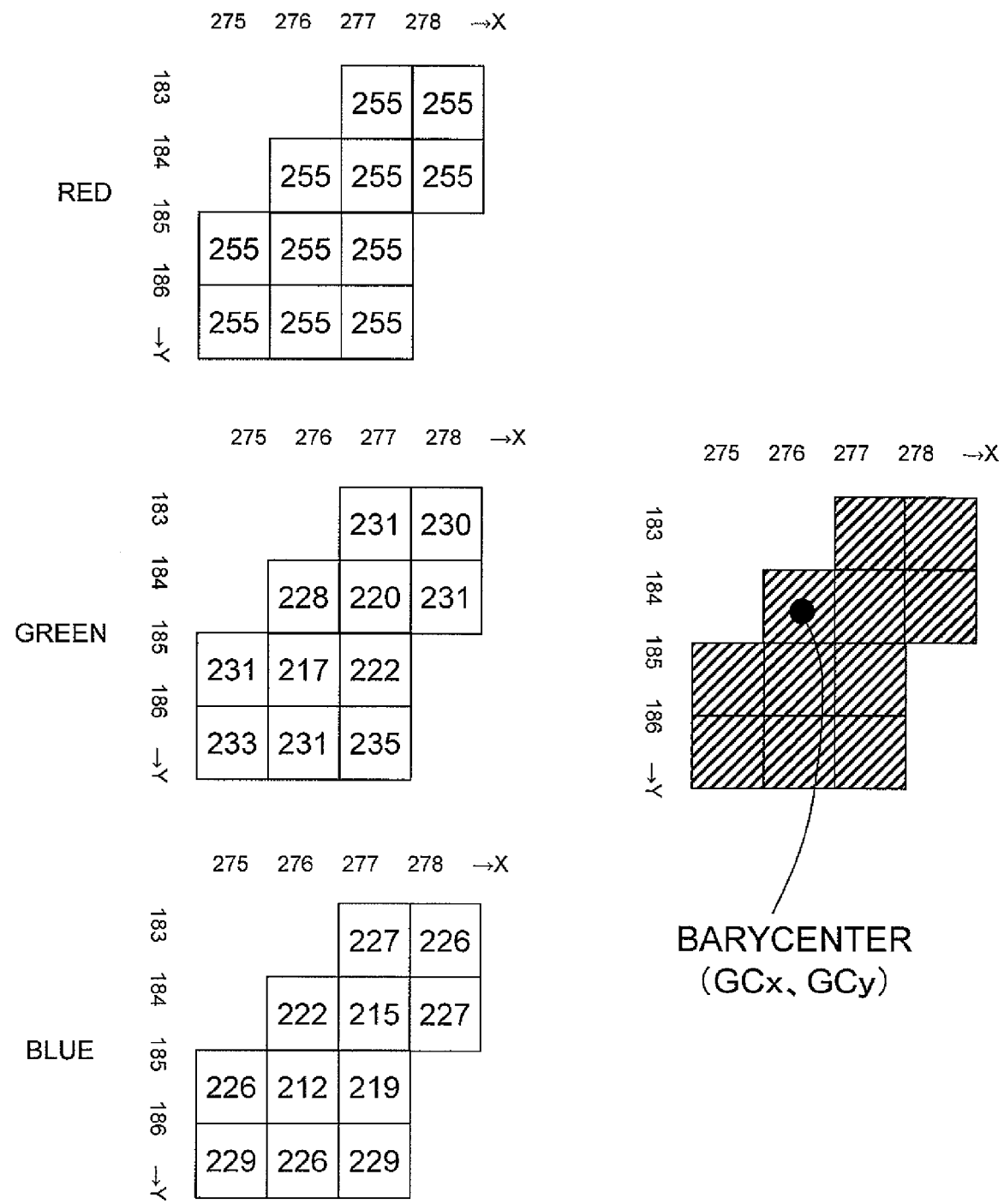
FIG. 18B shows data about a single reflection region.

FIG. 18B shows exemplary pseudo-color values (R, G, B) in one reflection area. This is an area consisting of eleven pixels that cover a range on the image with X-axis coordinates of 275 through 278 and with Y-axis coordinates of 183 through 186. Each of those pixels stores the YD and YPH values as pseudo-color values, which can get done by storing eight-bit values at respective pixel locations with the same set of coordinates on the RED, GREEN and BLUE planes. For example, at a pixel (X, Y)=(278, 184), which is one of the constituent pixels of this area, stored is (RED, GREEN, BLUE)=(255, 231, 227). If the barycenter position and the average of the pseudo-color values are calculated in the processing step 1803 described above, the coordinates of the barycenter of this area will be (GCX, GCY)=(276.5, 184.6) and the average color will be (RED_AVE, GREEN_AVE, BLUE_AVE)=(255, 228.09, 223.45). By subjecting these values to a well-known RGB_HSV conversion, for example, the groove principal axis angle H becomes H=0.0245 (i.e., approximately 8.82 degrees). Although this angle has a period of 360 degrees, the groove principal axis angle Ø has a period of 180 degrees. That is why the groove principal axis angle Ø may be set to be a half as large as H. Thus, in the example illustrated in FIG. 18B, the groove principal axis angle Ø becomes approximately 4.41 degrees. In such a state, a binary image, to which an area has been labeled as area #nr, has been obtained and the attribute and statistical quantity of each area can be fixed.

Hereinafter, the actual search process will be described.

Specifically, in Step S1804 shown in FIG. 18A, a search region number nr is reset to be one as initial setting. Next, in Step S1805, a search line is calculated with respect to the search region. As described above, the "search line" is used to define a search region in which a mirror image is searched for. Thereafter, a target search region number nr1 is set to be one in Step S1806 and then that region is actually searched in Step S1807.

In this case, a distance on the search line Len is stored with only a region that has a "similar color" in the sense of the pseudo-color value and that has short distance D from the search line used as a mirror image candidate Mrrcand.

Figure 19:
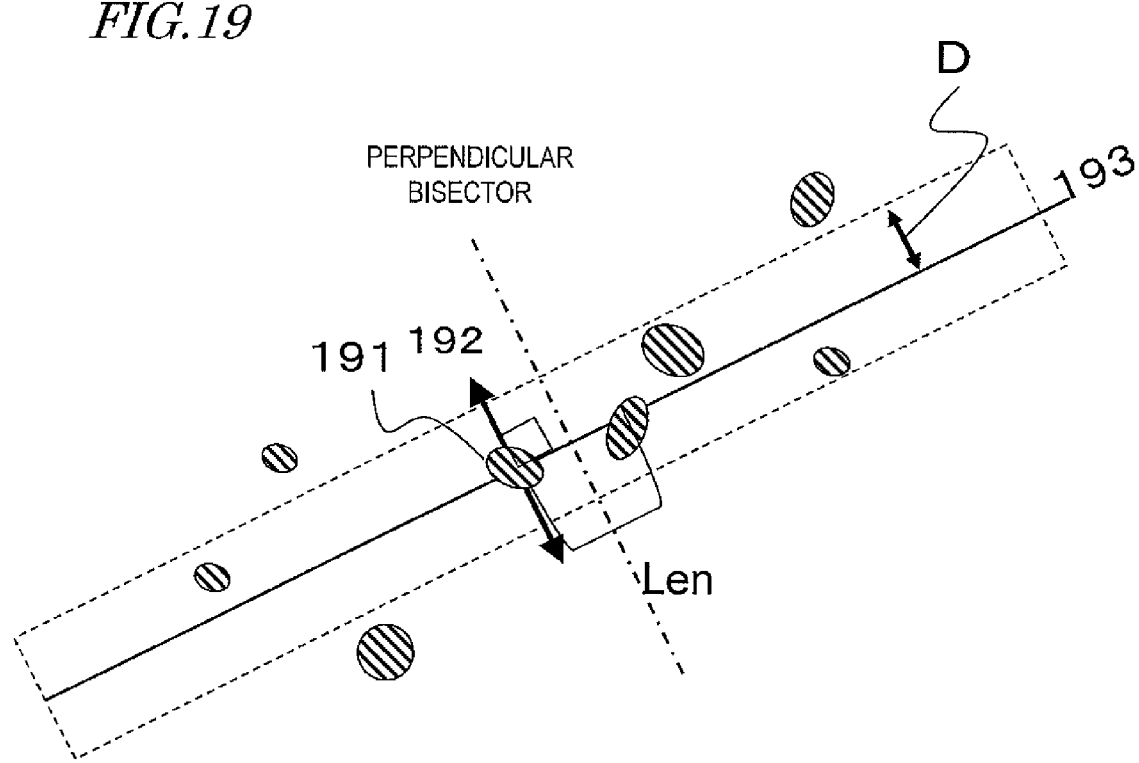
FIG. 19 illustrates exactly how to search a target search region.

FIG. 19 illustrates exactly how to search that target search region.

In this case, a region to be a reference for searching for the other region of a pair of twice-reflected regions is defined to be a search region 191 and the groove principal axis direction is supposed to be indicated by the arrow 192. First of all, by using Equations (15) for deciding whether or not the search region 191 and the target search region have close principal axis angles, a region that has a similar color to the search region 191 is located, and at the same time, the search line 193 is fixed.

$$\Delta H = \min(360 - |H(nr) - H(nr1)|, |H(nr) - H(nr1)|) \qquad (15)$$

$$SEARCH\_REGION = \begin{cases} YES & (\Delta H < TH\_H) \\ NO & (\Delta H < TH\_H) \end{cases}$$

Using the coordinates of the barycenter of the current search region and the principal axis angle θ of the twice reflecting groove, the search line equation can be represented as follows:

$$\begin{cases} x\cos\varphi + y\sin\varphi - GCx\cdot\cos\varphi - GCy\cdot\sin\varphi = 0 \\ (GCx, GCy)\cdots \text{ coordinates of search region's barycenter} \\ \varphi\cdots \text{ principal axis angle of search region} \end{cases} \qquad (16)$$

Therefore, the perpendicular distance D between the target search region (with the number nr1) and the search line needs to satisfy the following condition with respect to the search line of the search region (with the number nr):

$$SEARCH\_REGION = \begin{cases} YES & (D < D\_TH) \\ NO & (D < D\_TH) \end{cases} \qquad (17)$$

$$D = |(GCx(nr1) - GCx(nr))\cos\varphi + (GCy(nr1) - GCy(nr))\sin\varphi|$$

If the conditions defined by Equations (15) and (17) are both satisfied, the distance on the search line Len is calculated by the following Equations (18):

$$Len = \sqrt{P^tP} \qquad (18)$$

$$P = \begin{bmatrix} \sin^2\varphi & -\sin\varphi\cos\varphi \\ -\sin\varphi\cos\varphi & \cos^2\varphi \end{bmatrix} \begin{bmatrix} GCx(nr1) - GCx(nr) \\ GCy(nr1) - GCy(nr) \end{bmatrix}$$

In Step S1809, the mirror image search section decides whether or not every target search region has been searched with respect to the search region nr. If the answer is NO, then the next target search region nr1 is set in Step S1808.

In Step S1810, the distance on the search line Len is sorted and two regions with short distances are chosen from multiple regions sorted. These two regions will be used as a pair of mirror images, which cannot have too long a distance between them. Thus, in Step S1811, if the shortest and second shortest distances are shorter than the longest distance LEN_TH, then the two regions are approved as a pair of mirror images.

$$MIRROR\_IMAGE\_REGION = \begin{cases} YES & (LenSort(2) < LEN\_TH) \\ NO & (LenSort(2) < LEN\_TH) \end{cases} \qquad (19)$$

Based on the pair of mirror image regions thus obtained, a perpendicular bisector corresponding to the groove is generated. If this line segment is called a "groove segment" and if its length is GRVLEN, the following Equation (20) is satisfied:

$$\begin{cases} \begin{bmatrix} x \\ y \end{bmatrix} = \begin{bmatrix} (GCx(nr) + GCx(mirror))/2 \\ (GCy(nr) + GCy(mirror))/2 \end{bmatrix} + t\begin{bmatrix} \cos\varphi \\ \sin\varphi \end{bmatrix} \\ -GRVLEN \leq t \leq GRVLEN \end{cases} \qquad (20)$$

If the mirror image search section confirms in Step S1812 that every region nr has been searched successfully, the process ends. On the other hand, if it turns out that not every region nr has been searched yet, then the process advances to the processing step of searching the next region (in Step S1813).

When these series of processing steps are over, the pair of mirror images can be connected to the group of reflected regions and a groove segment, which is expected to be present at their intermediate position as a locally subdivided candidate of the groove, can be set.

FIGS. 20A through 20D show experimental images that were shot by extracting groove segments from actual objects.

Figure 20A:
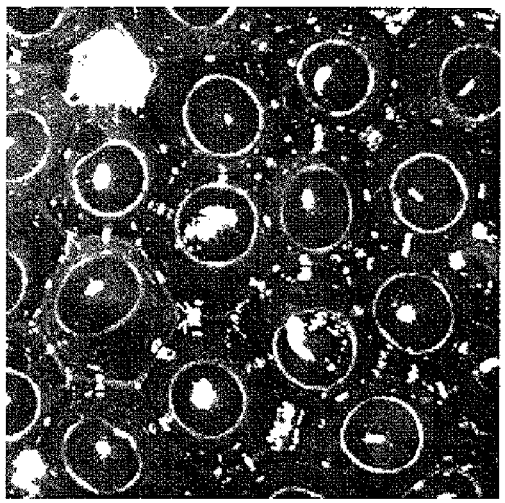
FIG. 20A is a photograph showing a light intensity image of an actual object.

FIG. 20A is a light intensity image that was generated based on four images of an object that had been shot with a rotating polarized light source. In this example, the object was a set of salmon spawn, of which the shape and reflection property would be similar to those of the unevenness on the surface of an organ. On the surface, a lot of once-reflected images of a ring light source and ring-like images produced due to its semi-transparency were observed, which would generate serious noise in light intensity image processing. According to the polarized light processing of the present disclosure, however, such an image can also be processed normally almost without causing a problem as can be seen from the processing results shown in FIGS. 20B through 20D.

Figure 20B:
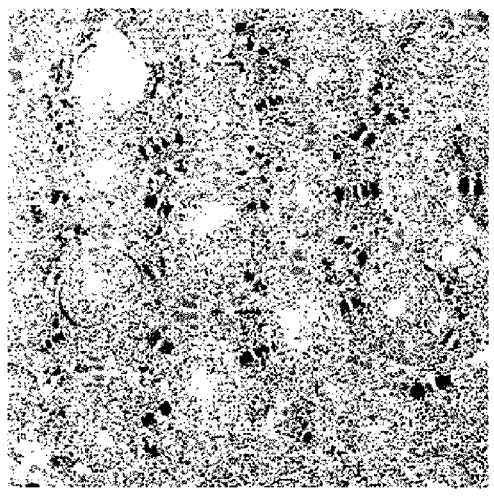
FIG. 20B is a photograph showing a pseudo-color image in which an intensity maximizing angle image YPH and a degree of intensity modulation image YD are combined together.

FIG. 20B shows the result of the processing that was carried out by the varying intensity processing section 1302. In FIG. 20B, the intensity maximizing angle image YPH and the degree of intensity modulation image YD are combined and shown as a single pseudo-color image.

Figure 20C:
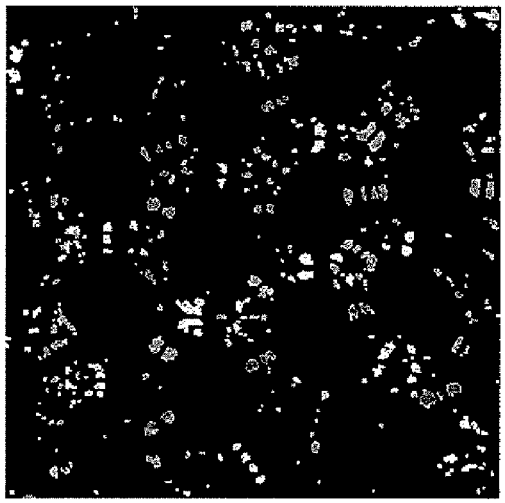
FIG. 20C is a photograph showing micro-reflection regions that have turned out to be twice-reflected regions as a result of quantization processing.

FIG. 20C shows the result of the processing that was carried out by the reflection decision section. Specifically, micro-reflection regions, which were determined to be twice-reflected regions as a result of quantization processing, had been separated and extracted. Those micro-reflection regions correspond to the respective regions shown in FIGS. 16C, 17A and 17B.

Figure 20D:
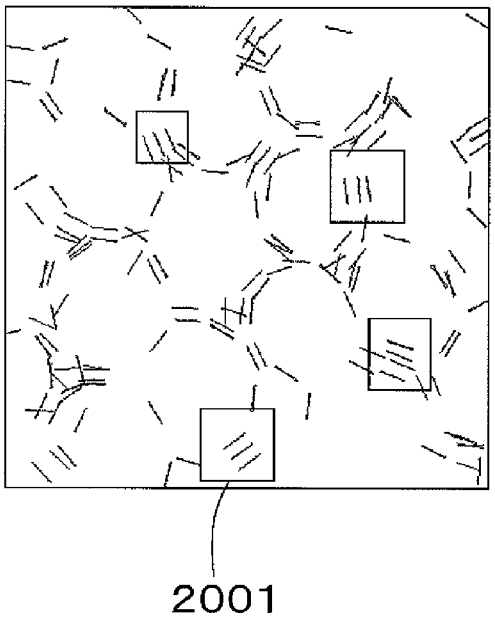
FIG. 20D is a diagram showing group segments that have been extracted as a result of the processing that has been performed by the mirror image search section.

FIG. 20D shows the result of the processing that was carried out by the mirror image search section 1306. Groove segments were extracted from the vicinity of the profile of each single piece of spawn. And a portion in which multiple parallel lines 2001 were extracted corresponds to a portion where multiple pairs of mirror image regions were detected.

Figure 21A:
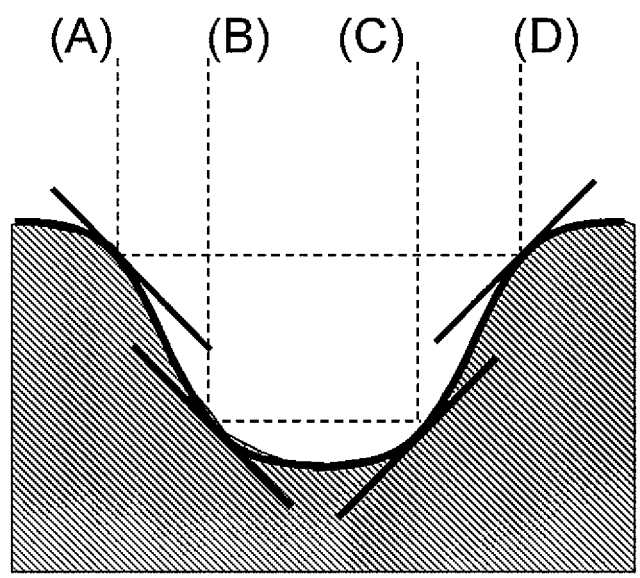
FIG. 21A illustrates why multiple pairs of mirror images are produced (cross-sectional view).
Figure 21B:
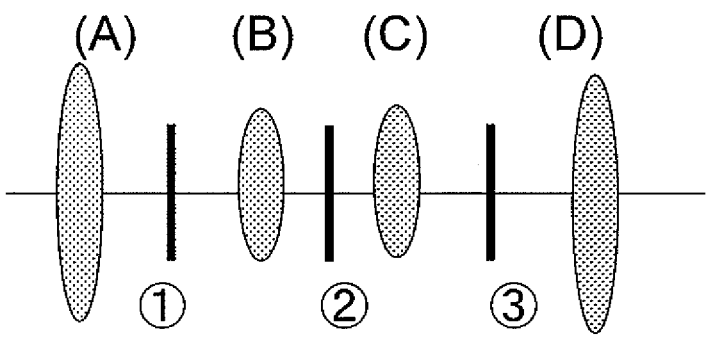
FIG. 21B illustrates why multiple pairs of mirror images are produced (showing reflection regions).

FIGS. 21A and 21B illustrate why such pairs of mirror images were generated. Specifically, FIG. 21A is a cross-sectional view illustrating the unevenness on the object's surface. In this case, since the slopes draw a curve with inflection points, it can be seen that the incoming light was reflected twice not only from points (A) and (D) but also from points (B) and (C) again as well. As a result, the four twice-reflected regions were observed on the same search line, and eventually, three groove segments were extracted as shown in FIG. 21B. Optionally, in that case, it may be determined by a different algorithm that the middle of the groove originally be the midpoint between (B) and (C).

The recessed region connecting section 1307 connects together groove segments that have been estimated, thereby generating a single set of recessed region and fixing the azimuth angle of the normal.

Hereinafter, the processing to be carried out by the recessed region connecting section 1307 will be described with reference to FIG. 22, which is a flowchart showing the procedure of the processing to get done by the recessed region connecting section 1307.

First, in Step S221 shown in FIG. 22, the recessed region connecting section 1307 sets target on every groove segment S that has been generated by the mirror image search section 1306. Next, in Step S222, the recessed region connecting section 1307 carries out an expanded version of the binary image processing depending on the direction of each of those groove segments S. The direction of this expanded processing is determined depending on the direction of each groove segment. Specifically, in this processing, each groove segment is expanded almost evenly both along its principal axis and perpendicularly to the principal axis and the groove segments are regarded as defining the bottom of the groove, thereby reproducing the groove's slope region.

Next, in Step S223, close ones of those expanded regions are connected together through image processing, thereby turning those groove segments, which have been distributed discretely depending on the distribution of the micro-reflection regions, into a single continuous connected groove region. Thereafter, in Step S224, the connected groove region is turned into fine lines through binary image processing, thereby determining fine lines corresponding to the bottom of the continuous connected groove region. Subsequently, in Step S225, vectors that point perpendicularly toward those fine lines are defined and regarded as representing estimated azimuth angles of the groove's normal vectors.

Then, in Step S226, a cross-sectional shape in the connected groove region is fitted to an existent function form such as a quadratic function, thereby estimating the zenith angle at the groove. In this case, the reflected light intensity of the micro-reflection regions is imposed as a constraint. As can be seen from FIGS. 10A to 12B, this angle is estimated by taking advantage of the fact that a slope angle at which the light incident on each cross section is reflected twice strongly is approximately 45 degrees with respect to the normal. By performing these processing steps, the connected groove region is estimated and the surface normal vectors at that location (i.e., the azimuth angle and the zenith angle) are estimated. Hereinafter, this processing will be described by way of an actual example.

Figure 23A:
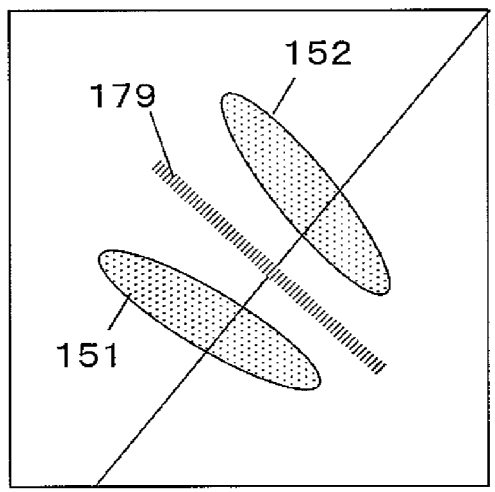
FIG. 23A shows a result of groove segment setting processing performed by the recessed region connecting section.
Figure 23B:
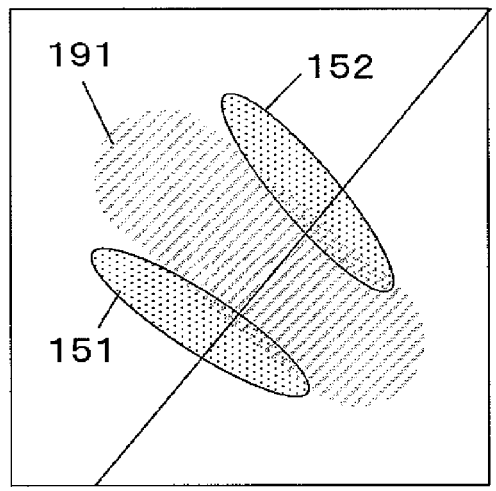
FIG. 23B shows a result of groove segment expansion processing performed by the recessed region connecting section.
Figure 23C:
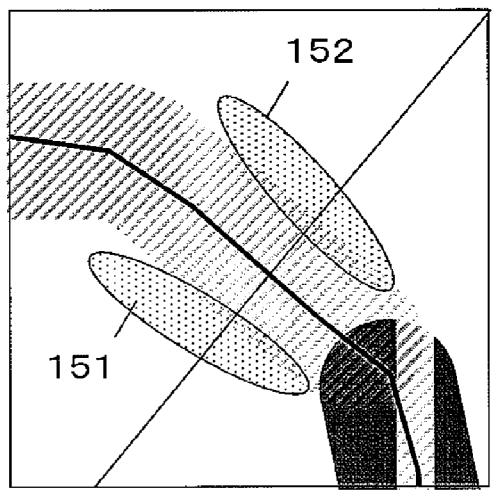
FIG. 23C shows a result of fine line drawing processing performed by a recessed region expanding section.
Figure 23D:
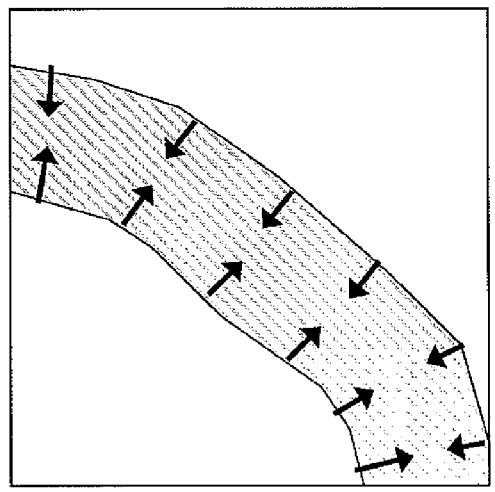
FIG. 23D shows a result of normal determining processing performed by the recessed region expanding section.

FIGS. 23A through 23D illustrate an example of a curved groove. This groove may be regarded as a groove that surrounds a raised convex region. Specifically, FIG. 23A illustrates micro-reflection regions 151 and 152 and a groove segment 179 that has been set. FIG. 23B illustrates a result of expansion processing that has been carried out on the groove segment 179. FIG. 23C illustrates how the groove segment looks after having been connected to another groove segment and subjected to fine line processing. At this stage, the connected groove region is curved around the lower left portion of the image and its bottom or valley position is indicated by fine lines. And FIG. 23D shows the azimuth angles of normals that have been estimated with respect to the groove thus obtained.

Figure 24A:
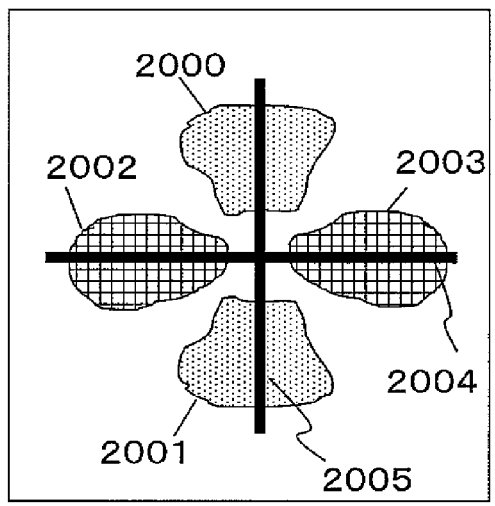
FIG. 24A shows a result of recessed region connection processing (of setting groove segments) in the case of holes.
Figure 24B:
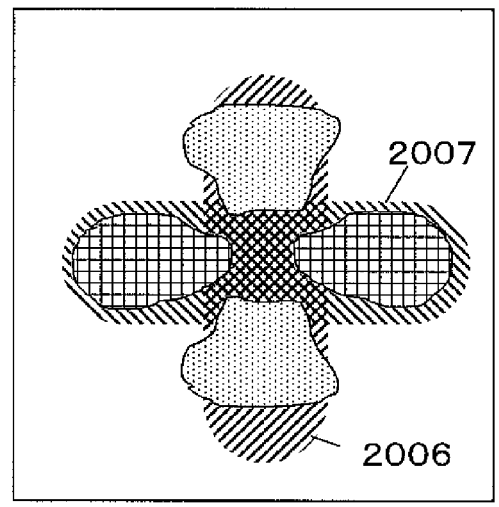
FIG. 24B shows a result of recessed region connection processing (of expanding groove segments) in the case of holes.
Figure 24C:
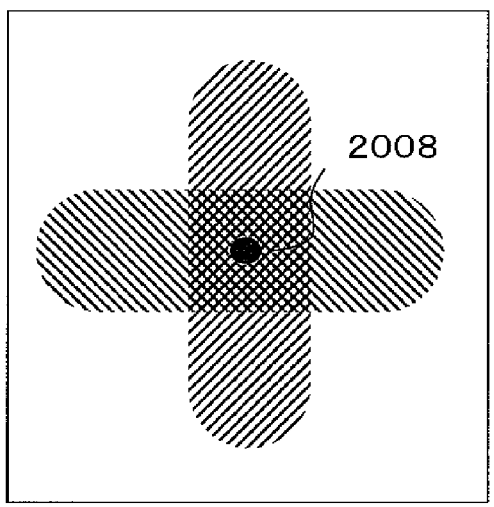
FIG. 24C shows a result of recessed region connection processing (of drawing fine lines) in the case of holes.
Figure 24D:
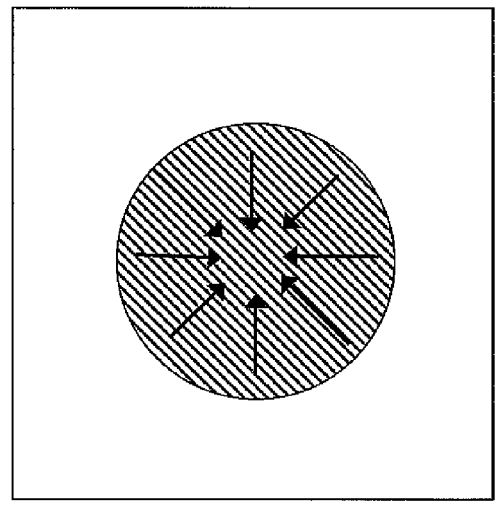
FIG. 24D shows a result of recessed region connection processing (of estimating normals) in the case of holes.

FIGS. 24A through 24D illustrate, as another example, a situation where there are a few recesses (or holes) on a flat surface. Since such a hole can be regarded as consisting of a lot of grooves that are distributed symmetrically to each other with respect to a point, there are an infinite number of pairs of twice reflected mirror images, theoretically speaking. Specifically, in FIG. 24A, micro-reflection regions 2000 and 2001 form a pair of mirror images, thus estimating a groove segment 2004. In addition, micro-reflection regions 2002 and 2003 form another pair of mirror images, thus estimating another groove segment 2005. FIG. 24B shows a result of the expansion processing that has been carried out on the groove segments. It can be seen that the expanded region defines a single closed cross region. If such a region is turned into fine lines, a point at the bottom can be estimated. FIG. 24C illustrates a hole as a recessed region that has been obtained based on the groove segments and a single point at the bottom of the hole. And FIG. 24D shows the azimuth angles of the normals that have been estimated with respect to the region of that hole.

Based on the azimuth angle that has been estimated by performing this series of processing steps, a cross-sectional shape modeling section 1308 estimates the zenith angle of the recessed region and determines the two angles that represent a normal. When the azimuth angle and zenith angle of the recessed region are determined in this manner, a normal image of the recessed region is generated.

Figure 25:
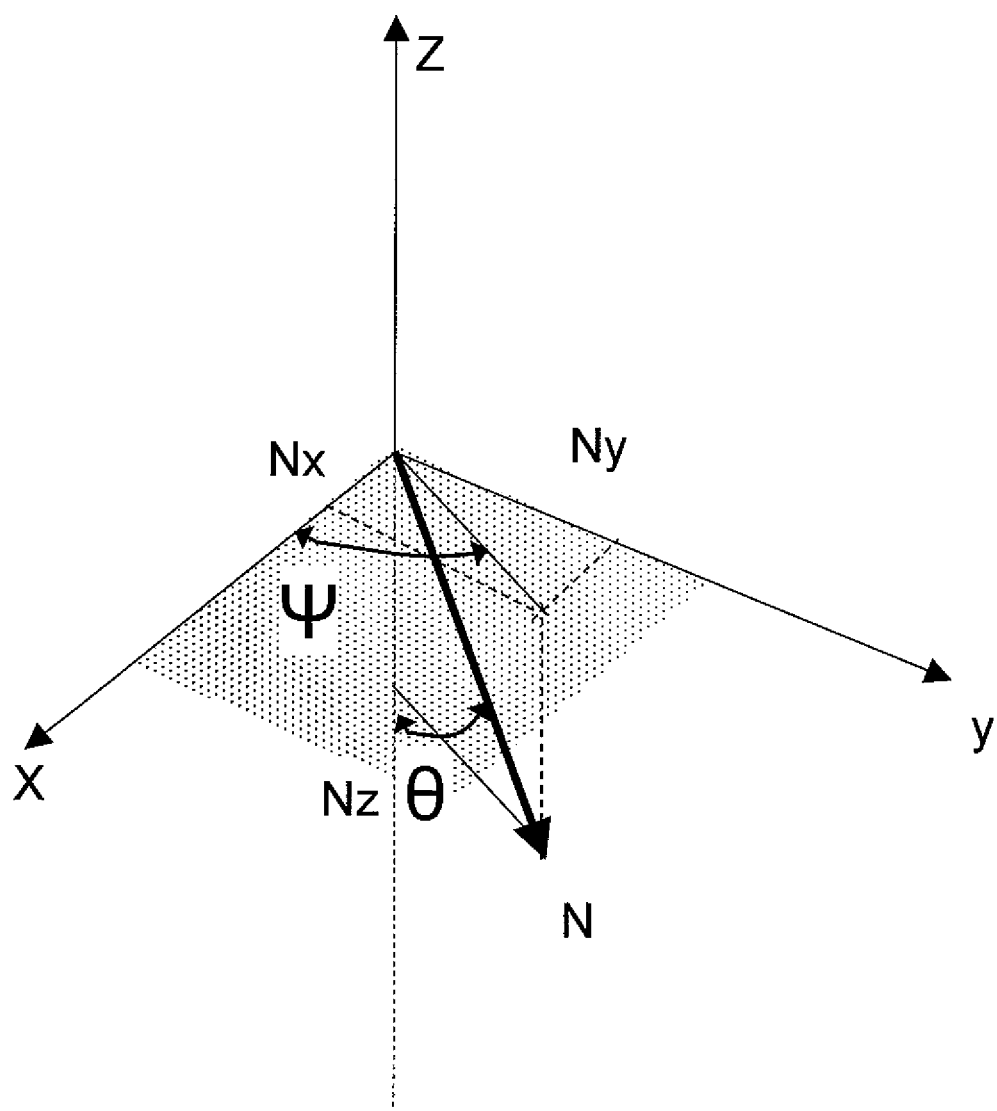
FIG. 25 shows the azimuth angle and zenith angle defined by a normal vector in a camera coordinate system.

FIG. 25 shows the azimuth angle and the zenith angle. The normal vector is a three-dimensional vector but its length has been normalized to one. Thus, the normal vector has a degree of freedom of two. And when represented as an angle, the normal vector can be represented by the azimuth angle $\psi$ within the screen and the zenith angle $\theta$ with respect to the line of sight. In a normal right-handed system, X and Y axes are defined within the image and the direction indicated by the Z-axis becomes the line of sight (i.e., optical axis) direction.

The relation between the normal and three components (Nx, Ny, Nz) is as shown in FIG. 25. Once the azimuth angle ψ and the zenith angle θ have been obtained based on the polarization information, the surface normal at that point is represented by the following Equations (21):

$$N_X = \cos\psi \sin\theta$$

$$N_Y = \sin\psi \sin\theta$$

$$N_Z = \cos\theta \quad (21)$$

Figure 26:
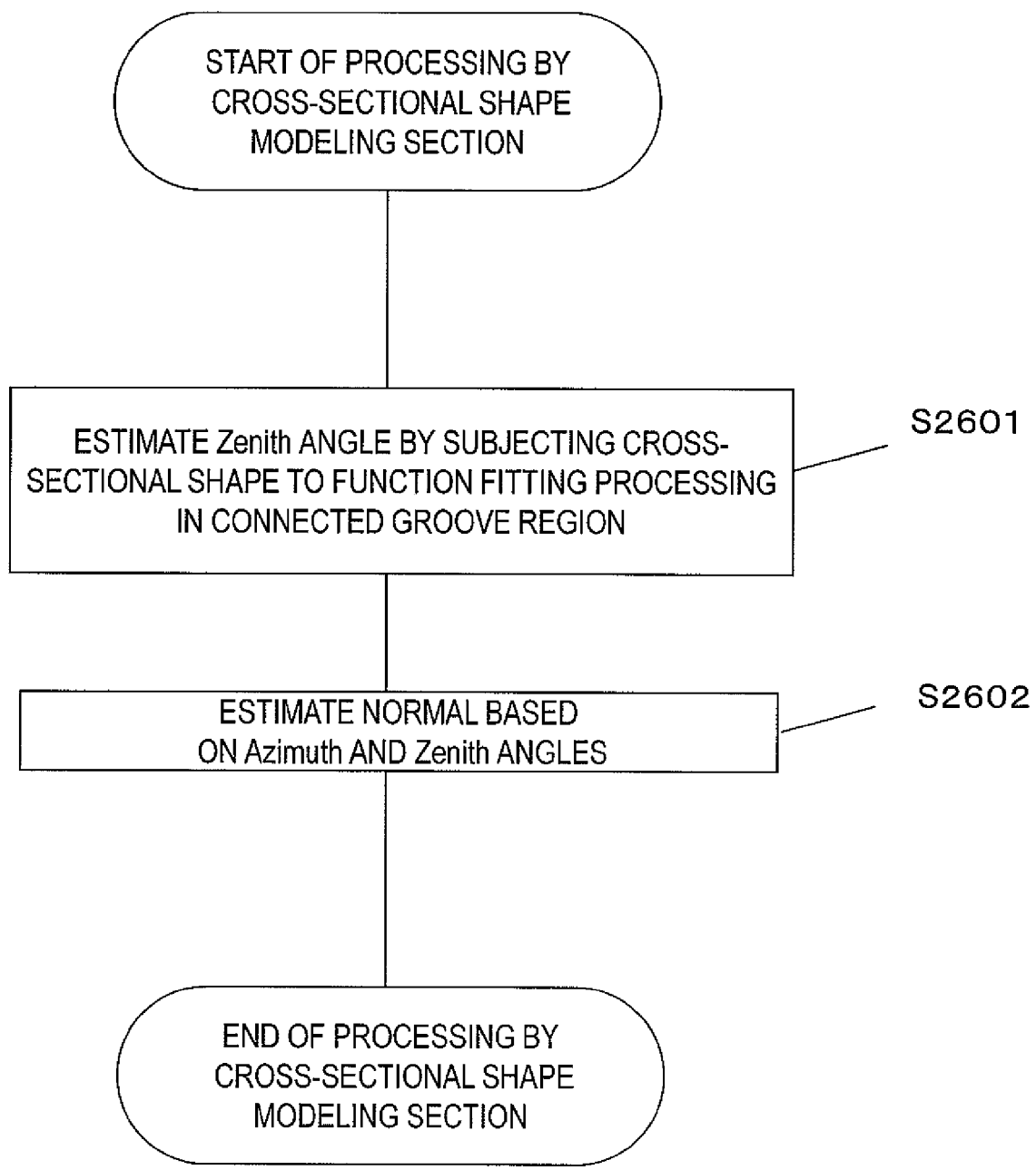
FIG. 26 is a flowchart showing the procedure of processing performed by a normal estimating section.

FIG. 26 shows the procedure of the processing to get done by the cross-sectional shape modeling section 1308. Specifically, in Step S2601, after the azimuth angle has already been estimated, the zenith angle is estimated.

The cross section of the groove may be fitted to a particular function form. In this case, a normal distribution function is used.

Figure 27:
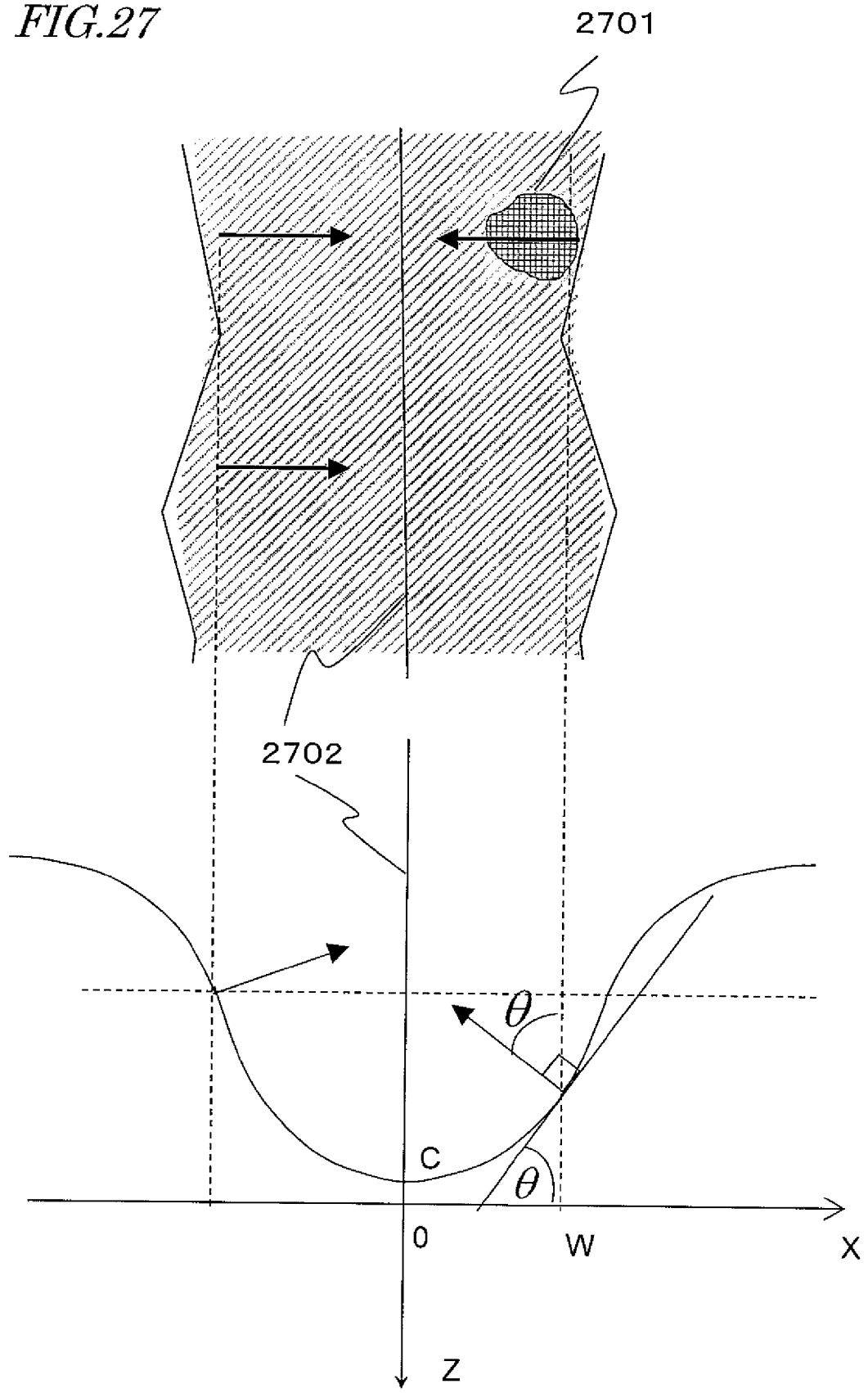
FIG. 27 is a plan view and a cross-sectional view that illustrate a groove that has been estimated.

FIG. 27 illustrates a plan view of the estimated groove as viewed from right over the object and also illustrates a cross-sectional view thereof. In this example, the groove is supposed to run in the Y axis direction with X=0 for the sake of simplicity. Also, in this example, the cross-sectional shape is supposed to be represented as a normal distribution function that uses σ as a parameter. A normal distribution function uses σ as the only parameter and therefore is a simple function. In addition, as a normal distribution function is similar to the shapes of various general grooves to be seen in an organism, the normal distribution function is chosen as the one representing the various cross-sectional shapes shown in FIGS. 10 to 12.

$$Z = -\frac{1}{\sqrt{2\pi\sigma^2}} e^{-\frac{x^2}{2\sigma^2}} \quad (22)$$

In this case, the gradient of the cross-sectional shape can be calculated by the following Equation (23) that uses the zenith angle θ of the normal:

$$\tan\theta = \frac{dZ}{dx} = \frac{x}{\sqrt{2\pi\sigma^3}} e^{-\frac{x^2}{2\sigma^2}} \quad (23)$$

Thus, supposing the position on the x-axis of the micro-reflection region 2701 to be subjected to the optimum fitting is W and θ at that position is 45 degrees at which the reflected light intensity becomes the highest, $$e^{-\frac{W^2}{2\sigma^2}} = \frac{\sqrt{\pi}\,\sigma^3}{W} \quad (24)$$

is obtained, and the parameter σ can be calculated by this equation. In this manner, the cross-sectional shape of the groove is represented as a normal distribution function and the zenith angle is determined by the magnitude of shift W from the centerline 2702 at the bottom of the groove. It should be noted that the more distant from the centerline of the groove, the flatter the value of the normal distribution function gets asymptotically. That is why this model can be used suitably as a model of a recessed portion on the surface of a mucosa such as the stomach.

Once the form of this function is determined, the zenith angle θ at a distance x from the groove's centerline is obtained by:

$$\theta = \tan^{-1}\left(\frac{x}{\sqrt{2\pi}\,\sigma^3} e^{-\frac{x^2}{2\sigma^2}}\right) \quad (25)$$

Naturally, a cross-sectional shape model other than the normal distribution function may also be used.

In Step S2602, a normal vector (Nx, Ny, Nz) to the object's surface in a camera coordinate system is calculated by Equation (21) using the azimuth angle ψ and zenith angle θ thus obtained, and is used as a two-dimensional normal image.

As can be seen from the foregoing description, although polarization information is used according to the present disclosure, no ambiguity is produced with respect to the azimuth angle or the zenith angle, which is a significant advantage over the ordinary polarization image processing. And such an advantage can be obtained because the normal is supposed to be estimated by using only the recessed portion as a model from the beginning.

The exemplary processing just described is the processing of estimating a normal to a recessed region on the object's surface, from which the incoming light is reflected twice. Next, it will be described how to process a region from which incoming light is reflected once.

A high intensity region processing section 1312 defines a normal to a portion of the object' surface that has been extracted as a region REF1 with very high intensity in FIG. 16.

Figure 28:
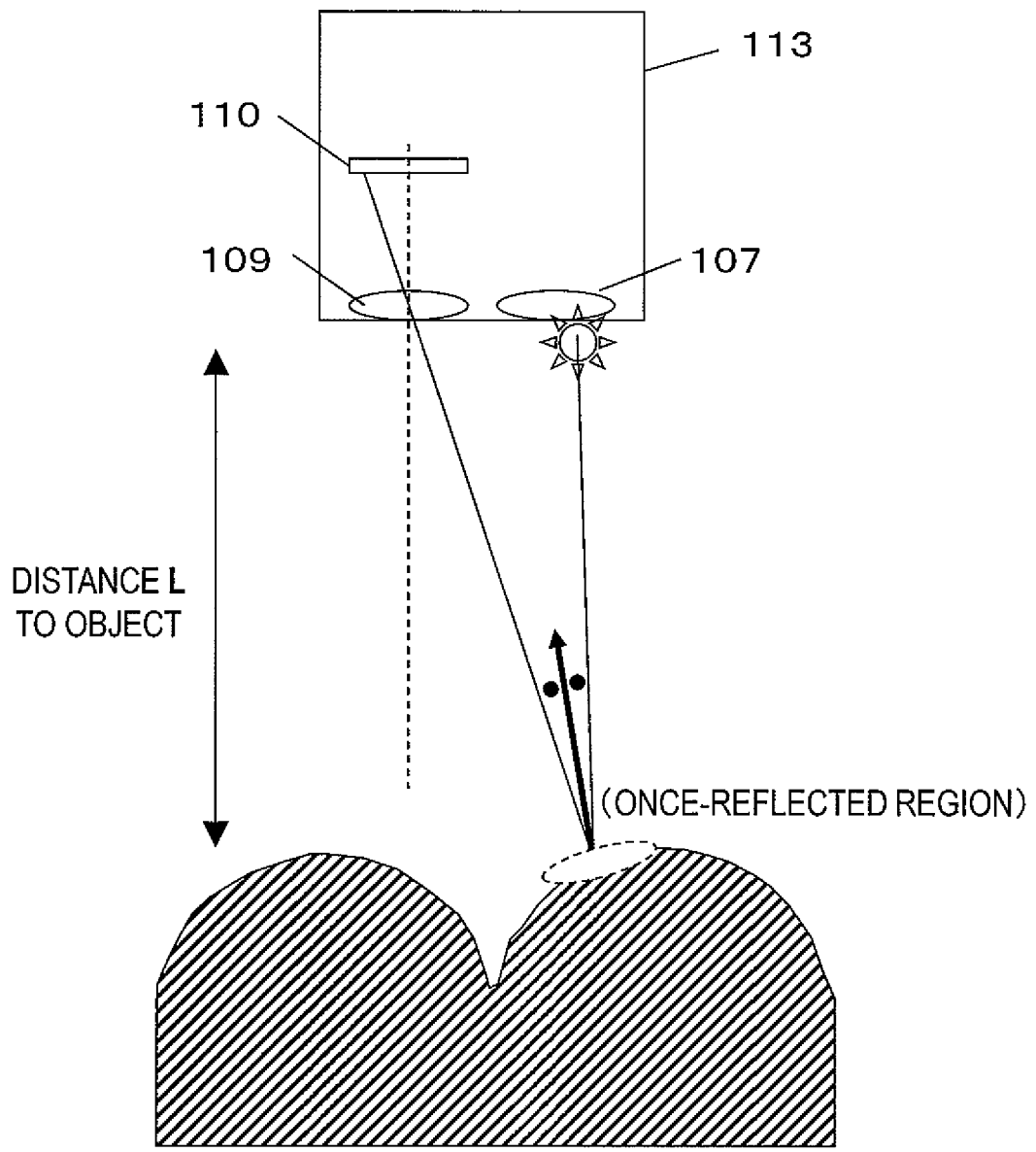
FIG. 28 illustrates how to estimate a normal to a once-reflected region in principle.

FIG. 28 illustrates the principle of defining a normal. Considering a property of a specular reflected light ray, of which the angle of incidence and angle of reflection are equal to each other when reflected once, a surface normal N1 to the region REF1 can be calculated as a bisector vector between a viewpoint vector V and a light source vector L.

By performing these processing steps, surface normals to the REF2 (twice reflected) and REF1 (once reflected) regions can defined. However, these normals are obtained just locally. Thus, a global normal is determined with respect to the entire surface of the object.

A normal reproducing section 1313 obtains a normal with respect to a normal undetermined region by applying a normal continuity assumption based on the relation between the theoretical surface reflection model and the single image's intensity observed, thereby determining a global normal. Since the incoming light is hardly reflected twice from that region, the intensity of the light may be regarded as being determined by the only one reflection based on the directions of the light source and the line of sight. That is why a technique for restoring the original shape based on a shadow, which is a so-called "shape from shading (SFS)" method that has been used frequently in the related art (see Katsushi Ikeuchi: "Determining 3D Shape from 2D Shading Information Based on the Reflectance Map Technique", Institute of Electronics and Communication Engineers of Japan, Trans. D, July 1982, Vol. J65-D, No. 7, pp. 842-849), may be adopted.

According to this technique, first of all, a surface normal (Nx, Ny, Nz), which is a vector in a three-dimensional space, is represented in the (f, g) space, which can be used conveniently to express the object's fringe linear constraint by way of a (p, q) gradient space. This conversion can be made by either the following Equations (26) or Equation (27):

$$p = \frac{\partial z}{\partial x} = -\frac{N_x}{N_z}, \quad q = \frac{\partial z}{\partial y} = -\frac{N_y}{N_z} \quad (26)$$

$$f = \frac{2p}{1 + \sqrt{1 + p^2 + q^2}}, \quad g = \frac{2q}{1 + \sqrt{1 + p^2 + q^2}} \quad (27)$$

Next, to estimate a normal (f, g) based on the intensity E (x, y) that has been actually measured at a pixel location (x, y), the relation represented by the following Equation (28) is supposed to be satisfied. For that purpose, the theoretical relation R (f, g) between the normal and the intensity measured needs to be defined. Such a relation can be obtained not only empirically but also by any of various physical reflection model formulas that approximate the object's reflection property with the position of the light source supposed to be known. As the specular reflection model, the Cook-Torrance model to be described later may be used, for example.

$$E(x,y) = R(f,g) \quad (28)$$

Next, assuming that the object's surface is smooth, the following normal continuity formula is supposed:

$$f_x^2 + f_y^2 + g_x^2 + g_y^2 \to \min \quad (29)$$

Thus, to satisfy Equation (28) and Formula (29), the following integral is minimized:

$$\iint [\lambda(E(x,y) - R(f,g))^2 + (f_x^2 + f_y^2 + g_x^2 + g_y^2)] dx dy \to \min \quad (30)$$

This minimization problem is reduced to solving the following Eulerian equations (31) and can be solved by adopting an iterative method discretely.

$$\begin{cases} \nabla^2 f = \lambda(E - R)R_f \\ \nabla^2 g = \lambda(E - R)R_g \end{cases} \quad (31)$$

The normal vector is obtained by inverting the eventually obtained (f, g) space by way of the (p, q) space.

Figure 29A:
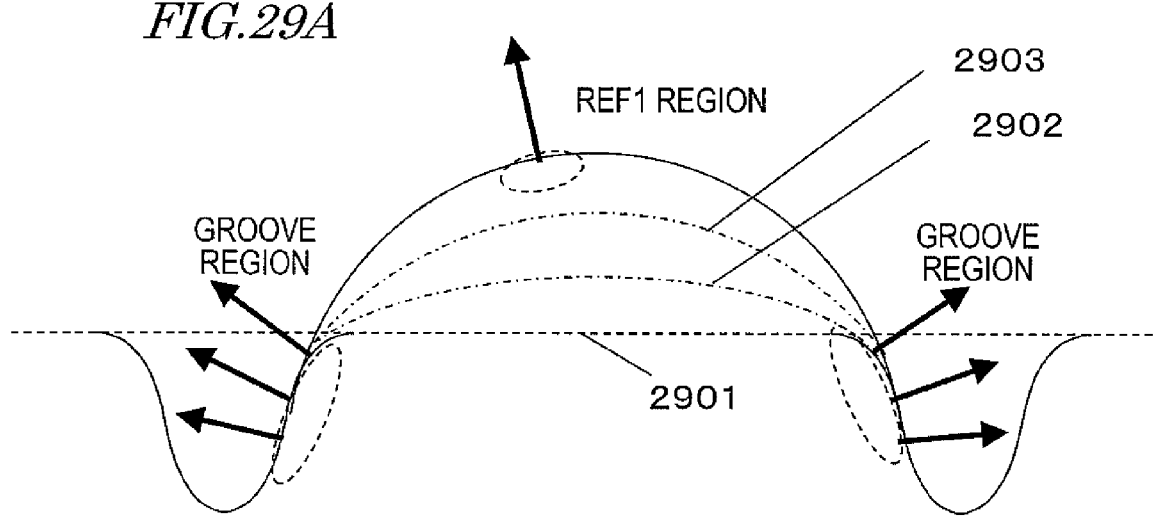
FIG. 29A illustrates surface normals that have been estimated by an iterative method and a cross section of an object.

FIG. 29A schematically illustrates how normals are gradually formed by this iterative method with respect to a surface raised portion. The initial surface is flat as indicated by the reference numeral 2901. However, if the iterative method is applied, a raised region is gradually formed as indicated by the reference numerals 2902 and 2903. It should be noted that a group of normals defined with respect to a groove region and a normal defined with respect to the REF1 region can be used as constraints. By performing these processing steps, a normal image N can be generated.

Figure 29B:
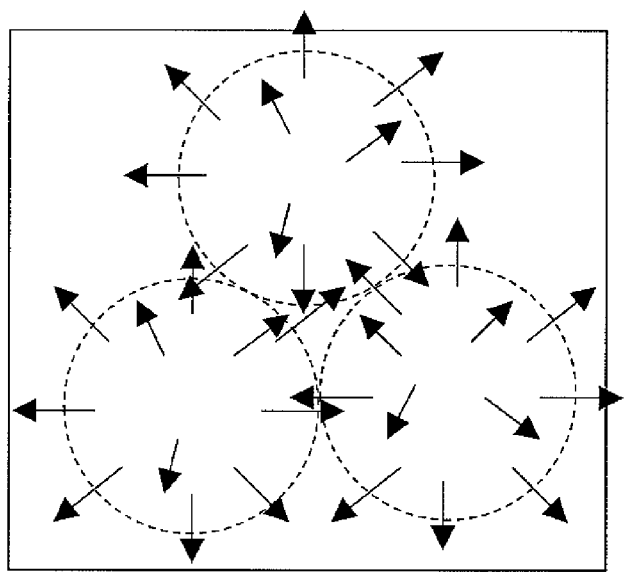
FIG. 29B schematically illustrates normal images that have been estimated.

FIG. 29B schematically represents a normal image. To each pixel of a light intensity image, attached is data of surface normal vector defined with respect to that pixel's location. The following description relates to a section in which an image that has been generated in this manner is displayed as a part of a synthetic image.

First of all, as shown in FIG. 1C, the normal image N is sent to a shifted light source image generating section 117. The shifted light intensity image generating section 117 generates a light intensity image based on a physical reflection modeling formula by giving the camera viewpoint direction and the illuminating light source direction to the normal image thus obtained. In this example, the Cook-Torrance model is used as a modeling formula that represents the object's specular reflection well. According to the Cook-Torrance model, the intensity Is can be represented by the following Equation (32):

$$I_S = K \frac{FG \frac{1}{4m^2 \cos^4 \alpha} \exp\left(-\frac{\tan^2 \alpha}{m^2}\right)}{\cos \theta_r} \quad (32)$$

Figure 30:
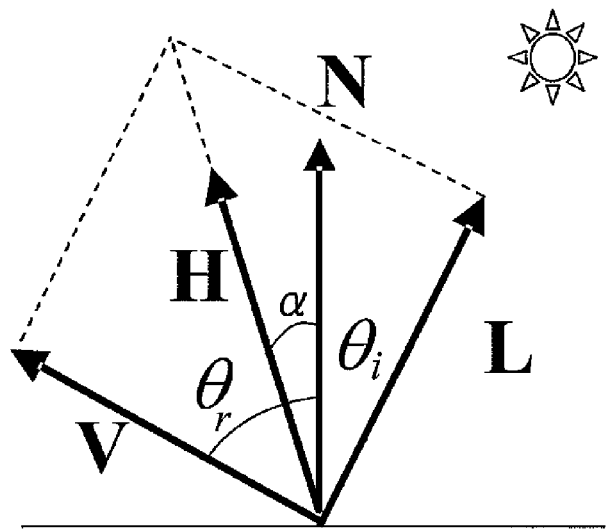
FIG. 30 illustrates a geometric relation between a surface normal, a light source and a viewpoint.

FIG. 30 shows a relation between the vector and the angle in a situation where the Cook-Torrance model is used and illustrates a surface normal N, a light source vector L and a viewpoint vector V. If a bisector vector H of the light source vector L and the viewpoint vector V is used, α in the Equation (32) is the angle defined by the bisector vector H with respect to the normal N and θ r is the angle formed between the viewpoint vector and the normal N. The Fresnel coefficient F and the geometric attenuation factor G are represented by the following Equations (33) and (34), respectively:

$$F = \frac{1}{2} \frac{(g-c)^2}{(g+c)^2} \left(1 + \frac{[c(g+c) - 1]^2}{[c(g-c) + 1]^2}\right) \quad (33)$$

$$G = \min\left(1, \frac{2(N \cdot H)(N \cdot V)}{(V \cdot H)}, \frac{2(N \cdot H)(N \cdot L)}{(V \cdot H)}\right) \quad (34)$$

Also, the coefficient K is a coefficient concerning the illuminance of the incoming light. If this Cook-Torrance model is used, the light intensity image can be generated based on the surface normal image. For that purpose, however, not only the refractive index n but also the viewpoint vector V, the light source vector L and other geometric settings need to be determined as well.

The light source direction setting section 114 is a man-machine interface for defining this light source vector and is set freely by a physician that is a user who is observing and inspecting the object with an endoscope. Specifically, the illuminating light source may be set anywhere but at a position where a light source for an endoscope is actually located. For example, the illuminating light source may be virtually set so as to illuminate the object from the left, from the right, from over, or from under the object. As a result, the object's surface unevenness can be represented as an image with plenty of reality.

Figure 31:
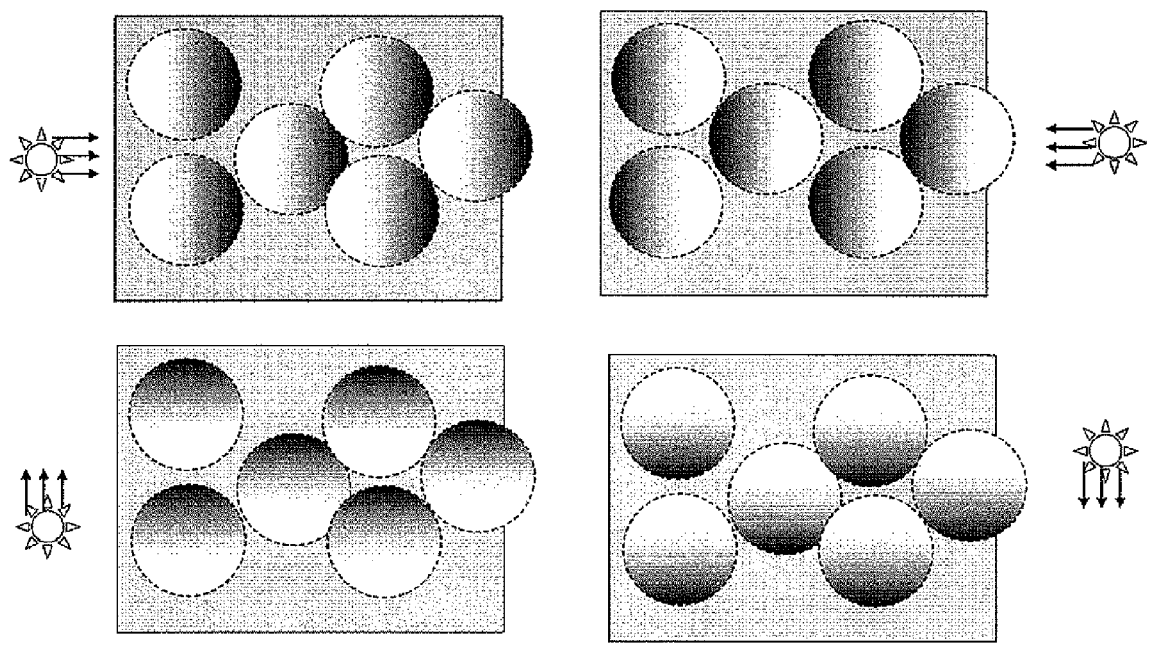
FIG. 31 illustrates examples of shifted light source images.

FIG. 31 schematically illustrates such images that have been shot with the light source shifted in this manner. Since these images are based on an estimated normal image, the position of the light source can be changed freely on a computer, thus overcoming one of the problems with an endoscope that inability to change the position of the light source makes it difficult to observe the surface unevenness.

The only image that can be actually represented by the Cook-Torrance model is a specular reflected image consisting of only glossy portions. For example, in the case of a color image, the specular reflected image is produced by only a white light source and therefore becomes a monochrome image, which lacks in reality by itself. For that reason, the specular reflected image and the light intensity image Y are synthesized together by the image synthesizing section 115.

Figure 32A:
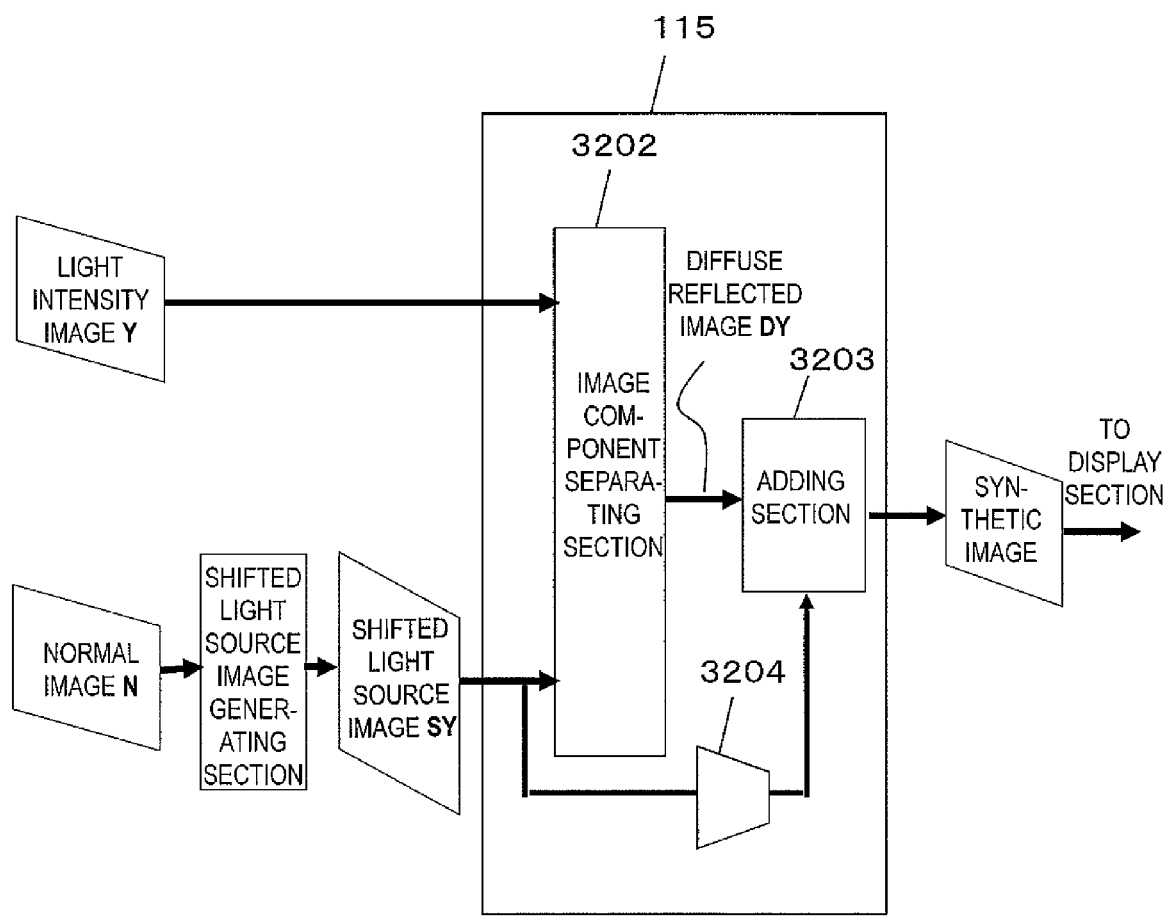
FIG. 32A is a diagram illustrating an exemplary configuration for a synthesizing section that synthesizes together a light intensity image and a shifted light source image.

FIG. 32A shows how to carry out that synthesis processing.

The light intensity image Y and the shifted light source image SY are sent to the image synthesizing section 115, in which first all, an image component separating section 3202 separates a diffuse reflected image DY. This separation gets done by subtracting the shifted light source image SY, which is a specular reflected image that has been obtained with the light source set in the same state as in shooting, from the light intensity image Y. The color components described above remain in this diffuse reflected image DY. Next, a shifted light source image SY is generated with the light source shifted to an arbitrary position, a weight is added thereto by a weight coefficient setting section 3204, and then those images are added together by an adding section 3203. The resultant synthetic image is then sent to a display section.

Figure 32B:
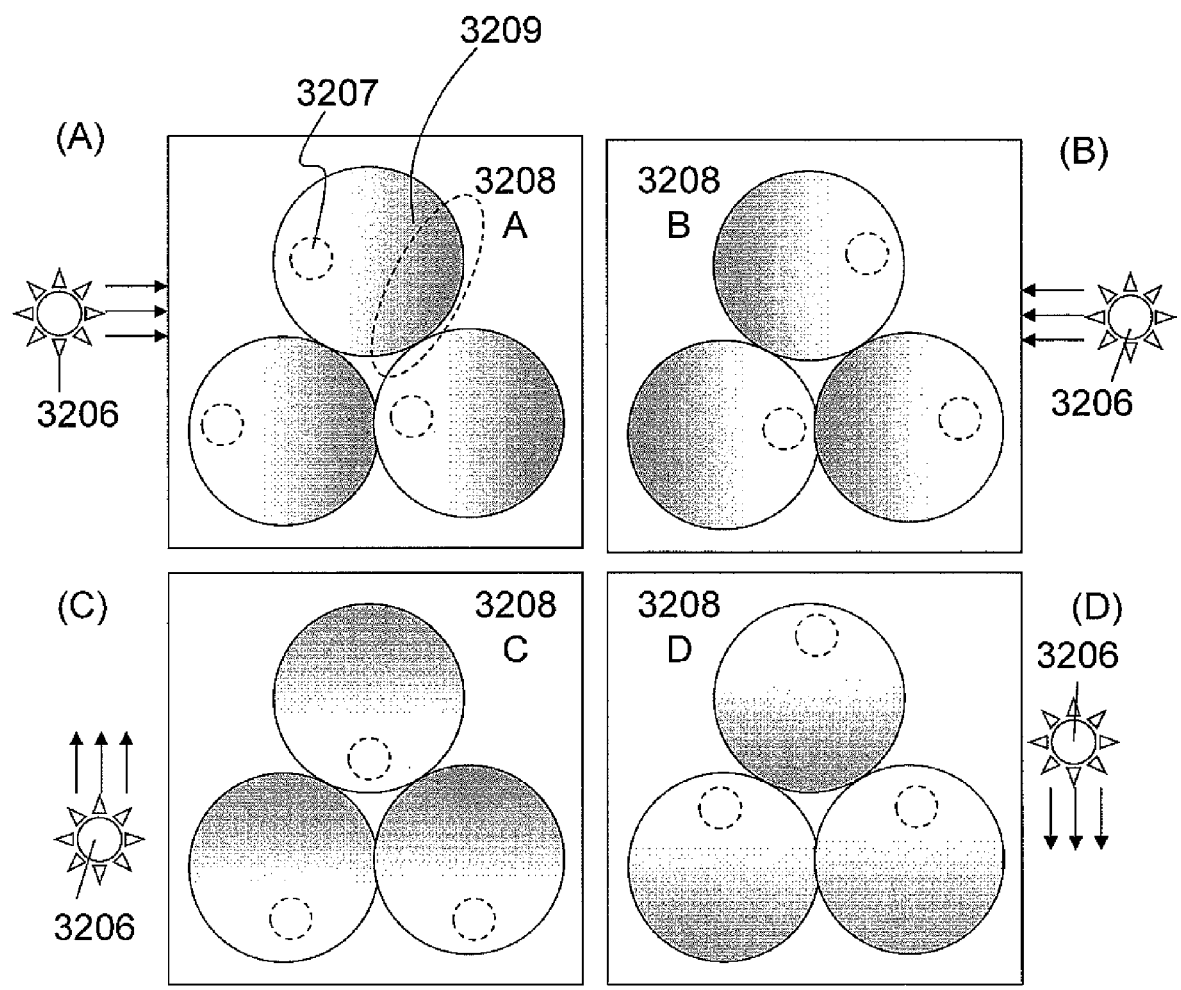
FIG. 32B is a diagram illustrating how to synthesize a light intensity image and a shifted light source image together.

FIG. 32B illustrates examples of displayed images that are obtained as a result of such a synthesis process. In this case, the light source 3206 is an arbitrary parallel light source that has been set virtually. If the direction of the light source 3206 is set freely as shown in portions (A) through (D) of FIG. 32B, then the object image will change as indicated by the reference numerals 3208A through 3208D. In particular, as the specular reflected portion 3207, from which the light is reflected only once, and a shadow portion 3209 move as the position of the light source is changed, the viewer can sense the unevenness visually. As a result, the physician can view not only a normal light intensity image but also such an image that represents the unevenness with plenty of reality as well, and therefore, can get useful information to make a diagnosis.

Figure 33A:
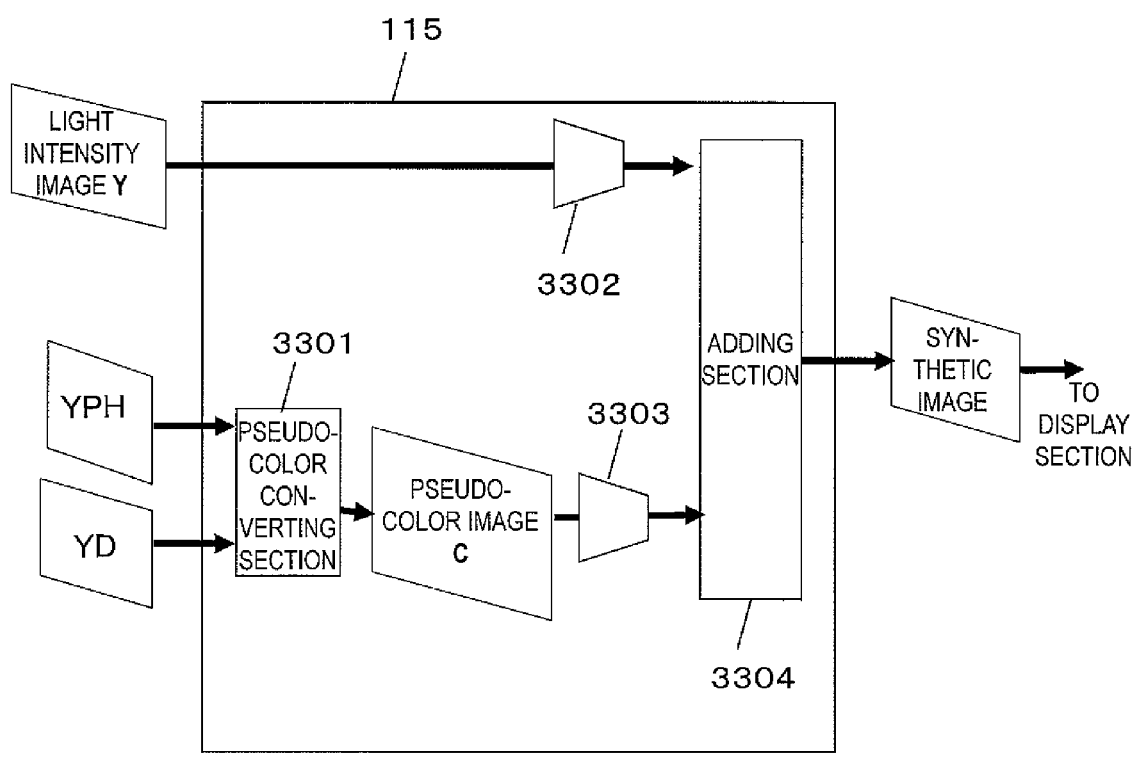
FIG. 33A is a diagram illustrating an exemplary configuration for a synthesizing section that synthesizes together a light intensity image and a pseudo-color image.

FIG. 33A illustrates another embodiment of the synthesis process. In this example, not the light intensity image to be generated based on the normal image N but pseudo-color images to be generated based on the intensity maximizing angle image YPH and the degree of intensity modulation image YD, which are pieces of information that have not been turned into the light intensity image yet, are synthesized together. When input to the image synthesizing section 115, the intensity maximizing angle image YPH and the degree of intensity modulation image YD are converted by a pseudo-color converting section 3301 into a pseudo-color image C. This conversion may be a well-known HSV-RGB conversion, for example.

Next, a weight is added to the image by a weighting section 3303, and then sent, along with the light intensity image to which a weight has also been added by a weighting section 3302, to an adding section 3304, where those two weighted images are added together. In the pseudo-color image obtained in that case, its hue represents the azimuth angle of its surface groove.

Figure 33B:
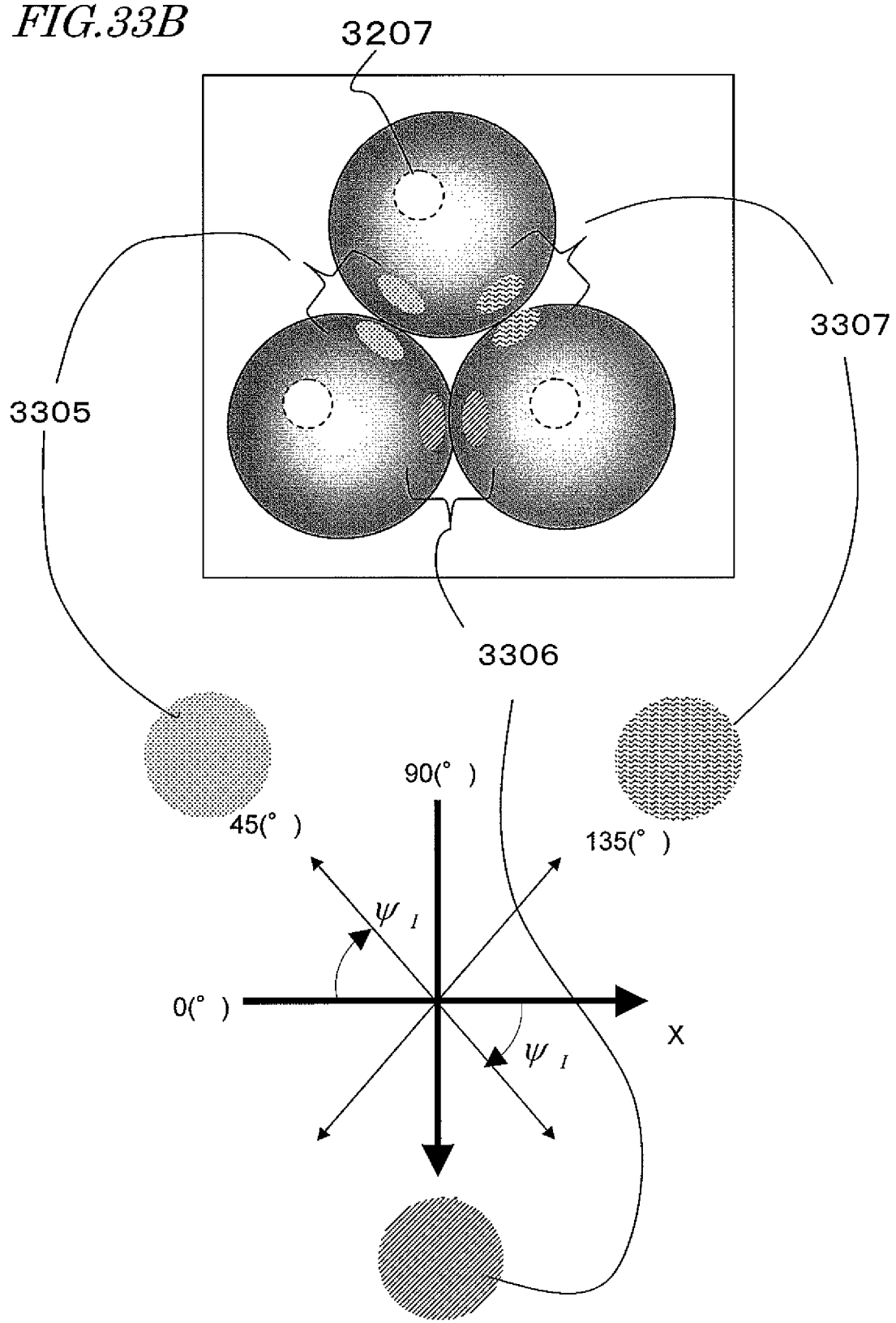
FIG. 33B is a diagram illustrating how to synthesize a light intensity image and a pseudo-color image together.

FIG. 33B illustrates examples of displayed images that have been obtained through the synthesis processing described above. For example, respective pseudo-color displayed images 3305, 3306 and 3307 indicate that there are grooves in the directions that are defined by azimuth angles of 45, 90 and 135 degrees, respectively. As a result, the physician can know in what state the surface grooves are and where holes are. In this manner, information collected before the image processing is carried out can be used intuitively enough, even though such information can be used less intuitively than in the situation shown in FIG. 31. Although pseudo-color images are supposed to be obtained through synthesis in this example, the intensity maximizing angle image YPH and the degree of intensity modulation image YD can also be synthesized together into a monochrome image as well.

As can be seen from the configuration of the image processing apparatus shown in FIG. 1C, this apparatus is not configured to obtain a different piece of information by changing the illuminating light sources to observe the object with, and therefore, the processing can be entirely carried out in parallel. That is to say, while the light intensity image Y, which is a color image indispensable for an ordinary endoscope inspection, is observed, either a synthetic image of the light intensity image and the shifted light source image SY or a synthetic image of the light intensity image and the pseudo-color image C may also be displayed on the display section 116 in parallel. Naturally, the physician who is scanning the object with the endoscope can display those two kinds of images selectively by appropriately changing them.

(Modified Example of Embodiment 1)

Hereinafter, a modified example of the first embodiment will be described with reference to FIGS. 34, 35A and 35B.

In the first embodiment described above, the normal is estimated with the REF1 region (i.e., the once-reflected region) with a very high intensity on the object's surface shown in FIG. 16 supposed to be a raised region (see FIG. 28). However, as already described with reference to FIGS. 11A to 12B, the REF1 (once-reflected) region could also be a recessed region.

Thus, the apparatus of this modified example includes an unevenness decision section that decides whether the REF1 (once-reflected) region is a recessed region or a raised region. In the example to be described below, the object's surface is supposed to be a set of spherical regions.

Figure 34:
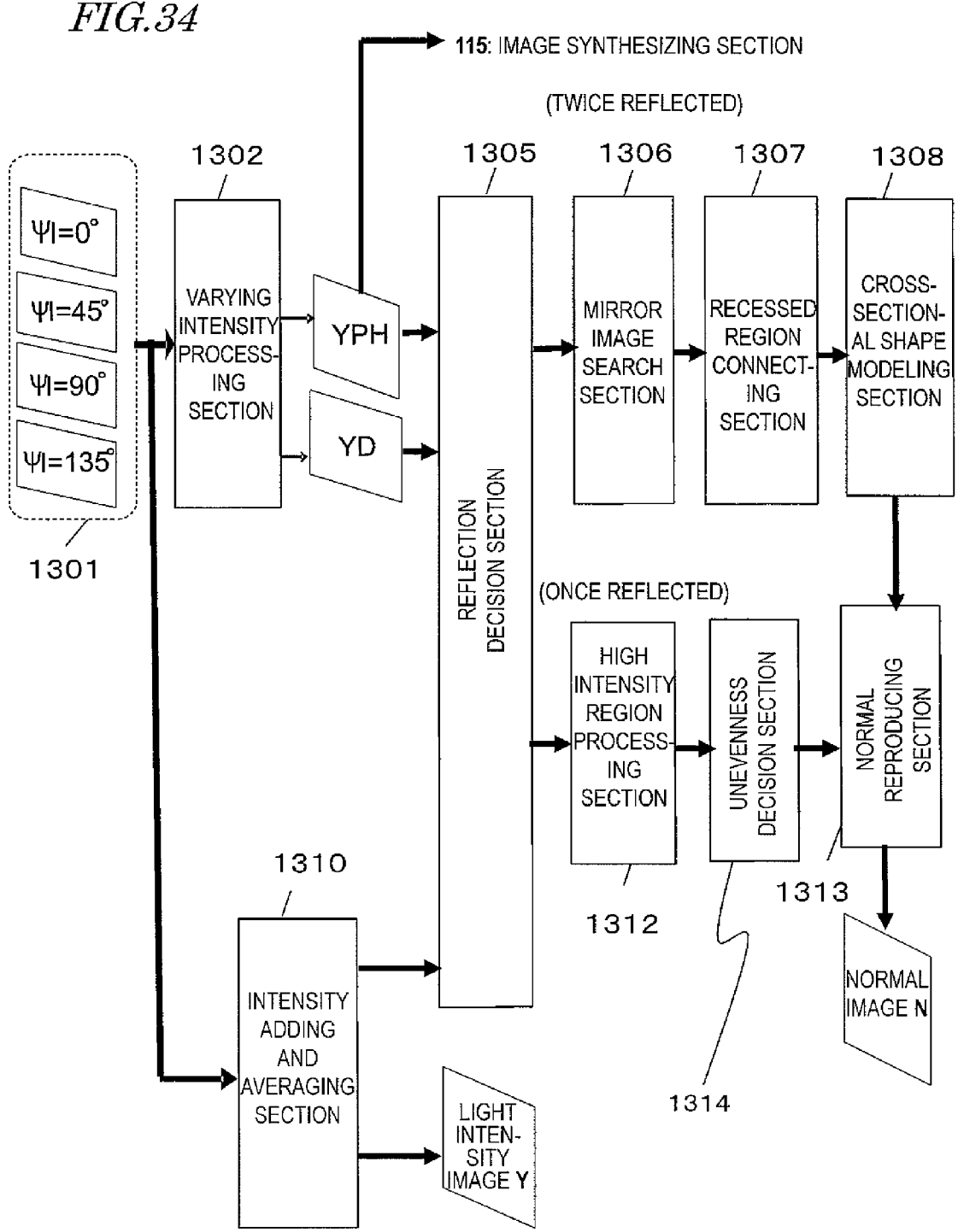
FIG. 34 is a block diagram illustrating a configuration for an image processing processor as a modified example of the first embodiment of the present disclosure.

Now take a look at FIG. 34, which illustrates a configuration for this modified example. A major difference between the configuration of this modified example and the configuration shown in FIG. 13 is that the apparatus of this modified example includes an unevenness decision section 1314. In this modified example, if the REF1 region that has been detected by the high intensity region processing section 1312 has turned out to be a raised region, processing by the normal reproducing section 1313 is carried out. That is to say, if the REF1 region has been determined to be a recessed region, the rest of the processing is carried on with that region excluded from the REF1 region.

Figure 35A:
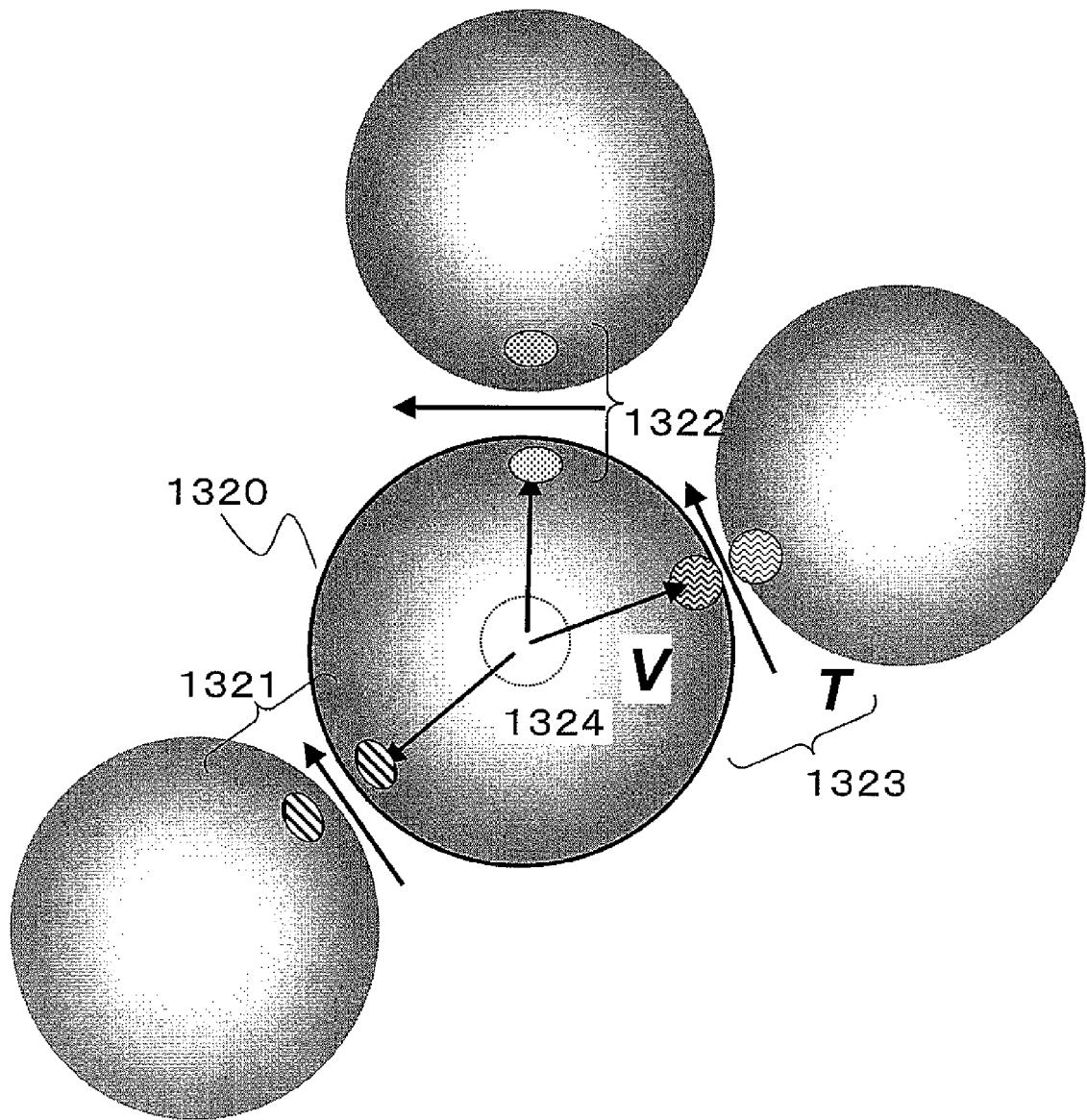
FIG. 35A illustrates a situation where REF1 regions are raised regions.

FIG. 35A illustrates a situation where the REF1 region is a raised region. In the example illustrated in FIG. 35A, a REF1 region 1324 is present in a spherical region 1320 and is surrounded with three REF2 regions 1321, 1322 and 1323. Suppose two-dimensional location vectors that start from the REF1 region 1324 and end in the REF2 regions 1321, 1322 and 1323, respectively, are identified by V, and the vectors representing the respective groove axes of the REF2 regions 1321, 1322 and 1323 are identified by T. Those vectors T may be groove segments that have been found as a result of a mirror image search or may be obtained simply as groove principal axes without any mirror image search. In the latter case, the vectors T have fixed directions but indefinite orientations.

As shown in FIG. 35A, the vectors T surround the REF1 region 1324 so as to rotate around the region 1324, and therefore, cross the vector V substantially at right angles. Generally speaking, the closer to 90 degrees the angle formed between two vectors is, the more distant from zero the outer product gets. Therefore, in the example illustrated in FIG. 35A, the vectors T and V satisfy the following Inequality (35):

$$E(|V \times T|) > \text{Tresh} \tag{35}$$

In this case, the absolute value of the outer product of these vectors V and T is used because the orientations of the vectors T are not taken into consideration. "E" denotes the average between multiple twice-reflected regions and "Thresh" denotes a predetermined threshold value. The magnitude of "Thresh" may be set to vary according to the type of the object but may also be determined either empirically or by calculations.

In this modified example, if Inequality (35) is satisfied, the unevenness decision section 1314 determines that the REF1 region 1324 be a raised region.

Figure 35B:
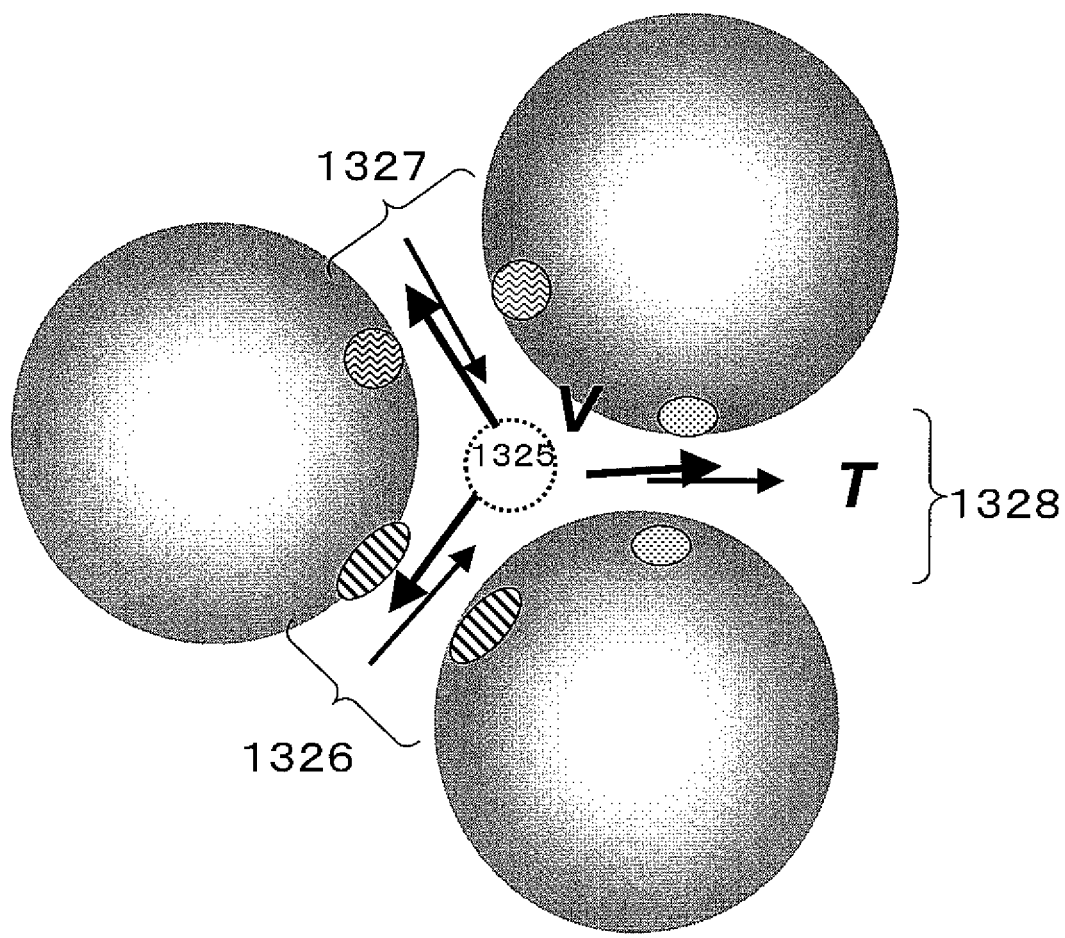
FIG. 35B illustrates a situation where REF1 regions are recessed regions.

FIG. 35B illustrates a situation where the REF1 region is a recessed region. Even in that case, the REF1 region 1325 is also located at the center of an area that is surrounded with multiple REF2 regions 1326, 1327 and 1328. However, if position vectors T that start from the REF1 region 1325 and ends at the REF2 regions and respective groove principal axis vectors V with respect to the REF2 regions 1326, 1327 and 1328 are defined, these vectors T and V become substantially parallel to each other. That is why if the REF1 region 1324 is a recessed region, then the following Inequality (36) is satisfied:

$$E(|V \times T|) \leq \text{Tresh} \qquad (36)$$

In this manner, the unevenness decision section 1314 can decide, based on the magnitude of the outer product of the vectors T and V, whether the once-reflected region is a recessed region or a raised region.

(Embodiment 2)

The image processing apparatus of the first embodiment described above is a so-called "flexible endoscope" type of which the image sensor is located at the tip portion. However, an endoscope according to the present disclosure does not have to be such a flexible endoscope type but may also be a rigid endoscope type as well.

Figure 36:
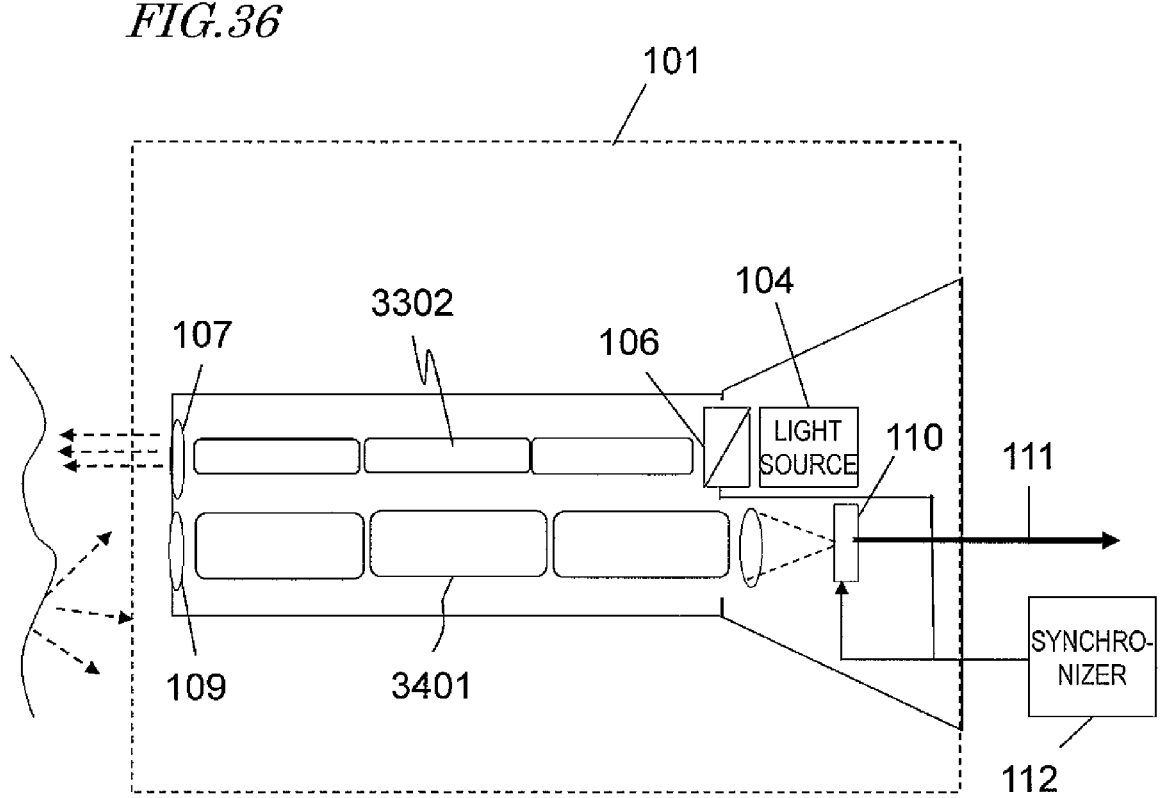
FIG. 36 is a diagram illustrating a second embodiment of the present disclosure.

Hereinafter, a second embodiment of an image processing apparatus according to the present disclosure (which is implemented as a rigid endoscope type) will be described with reference to FIG. 36, which is a block diagram illustrating an exemplary configuration for an endoscope 101 as this second embodiment of the present disclosure. The image processing apparatus of this embodiment has the same configuration as its counterpart shown in FIG. 1C except the endoscope 101, and the description thereof will be omitted herein.

The endoscope 101 included in the image processing apparatus of this embodiment includes an image capturing relay lens optical system 3401 and an illuminating relay lens optical system 3302. The image capturing relay lens optical system 3401 is designed to guide an object image that has been produced by the shooting lens 109 to the image sensor 110 that is located at the root of the endoscope, and has a general configuration for a rigid endoscope. According to this embodiment, the plane of polarization control element 106 is arranged right before the light source 104. Non-polarized light that has been emitted from the light source 104 is transformed into rotating plane polarized light. The plane polarized light is radiated through the illuminating lens 107 with its polarization state maintained while passing through the illuminating relay lens optical system 3302. According to this embodiment, there is no need to arrange the plane of polarization control element 106 shown in FIG. 1C at the tip end portion of the endoscope. As a result, the diameter of the tip end portion can be reduced. Optionally, a member that is bigger than the plane of polarization control element 106 may be adopted as a means for rotating the plane of polarization. For example, the plane of polarization control element 106 may be replaced with a mechanism that turns a polarizer with multiple different transmission polarization planes.

In the illuminating relay lens optical system 3302, the polarization state needs to be maintained through the process. In the image capturing relay lens optical system 3401, on the other hand, just the light intensity needs to be maintained. For that reason, the image capturing relay lens optical system 3401 can be adjusted more easily. The illuminating relay lens optical system 3302 may be replaced with a light guide that uses a plane of polarization saving fiber that maintains the same polarization state.

As in the first embodiment, the image processing processor also performs the same processing on a light intensity image that has been captured with a rotating polarized light source.

(Modified Examples of Embodiments 1 and 2)

For both of the first and second embodiments, the configuration of the rotating polarized light source section at the tip portion may be modified in various manners. To produce a lot of specular reflection from the object's surface unevenness, it is recommended that the illuminating light source is as uniform as possible and has as wide an area as possible. Nevertheless, since this is an endoscope, the tip portion suitably has as small a diameter as possible and as simple a structure as possible.

Various exemplary configurations for the tip portion of the polarized light source section 120 will be described with reference to FIGS. 37 through 41. In each of these drawings, a front view of the tip portion 113 is illustrated on the left-hand side and a cross-sectional view thereof is illustrated on the right hand side.

Figure 37:
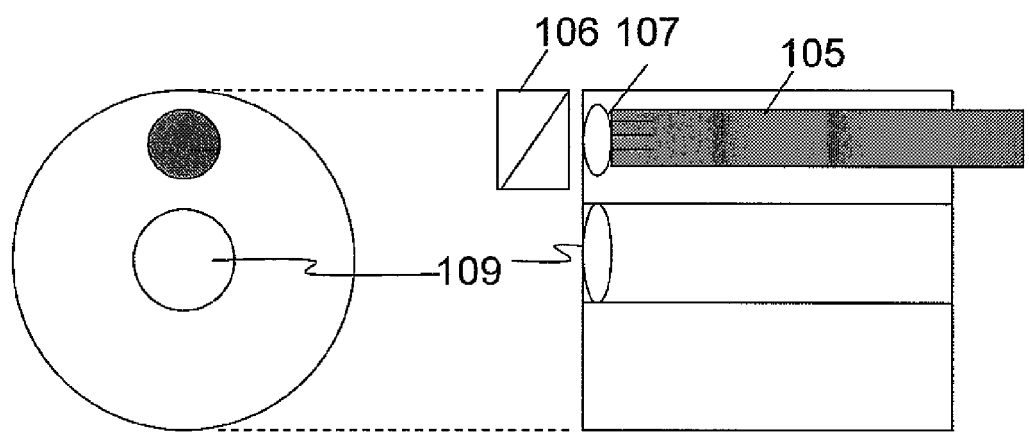
FIG. 37 illustrates a modified example of the first and second embodiments of the present disclosure.

FIG. 37 illustrates a tip portion of which the configuration is similar to that of its counterpart of the first embodiment. In this example, the plane of polarization control element 106 is attached outside of the illuminating lens 107.

Figure 38:
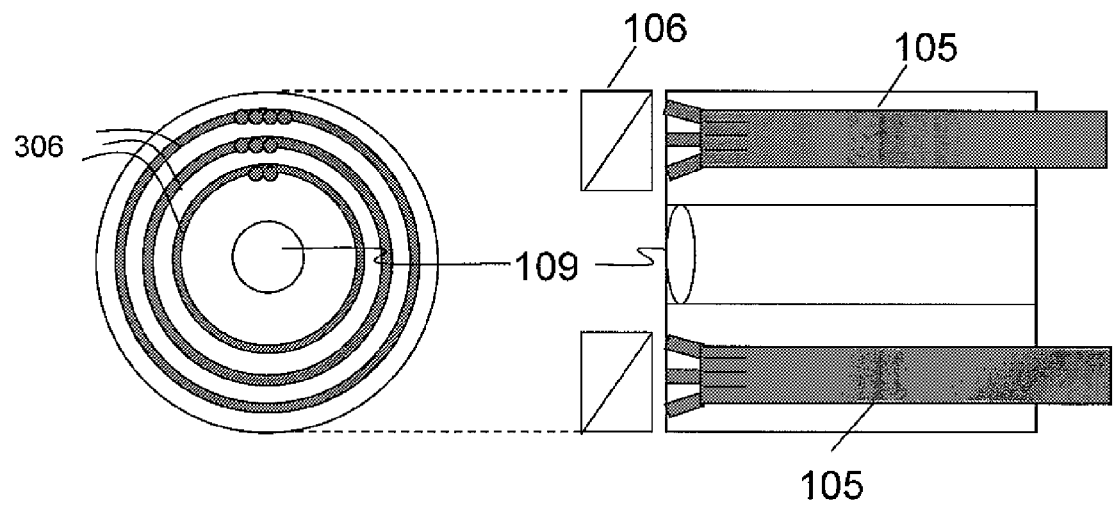
FIG. 38 illustrates another modified example of the first and second embodiments of the present disclosure.

FIG. 38 illustrates a configuration for a tip portion with a ring light source section 306. The light that has been emitted from the ring light source section 306 is passed through, and transformed by, a doughnut-shaped plane of polarization control element 106 with a center hole. This ring light source section 306 is formed by arranging in a circle the respective end faces of multiple optical fibers that branch from the light guide 105.

Figure 39:
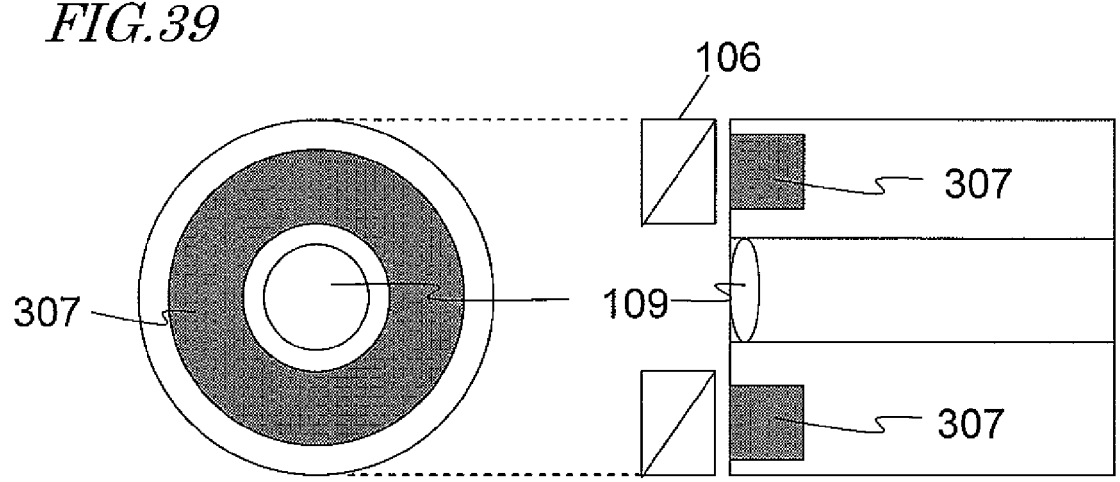
FIG. 39 illustrates still another modified example of the first and second embodiments of the present disclosure.

FIG. 39 illustrates a configuration for a tip portion having a ring light source section 307 with a broadened width. This ring light source section 307 has a plurality of LED chips that are arranged in the ringlike band region with the broadened width. As a result, a ring-like surface emission is obtained as a whole. The light emitted from the ring light source section 307 has its plane of polarization controlled when passing through the doughnut-shaped plane of polarization control element 106 with a center hole.

Figure 40:
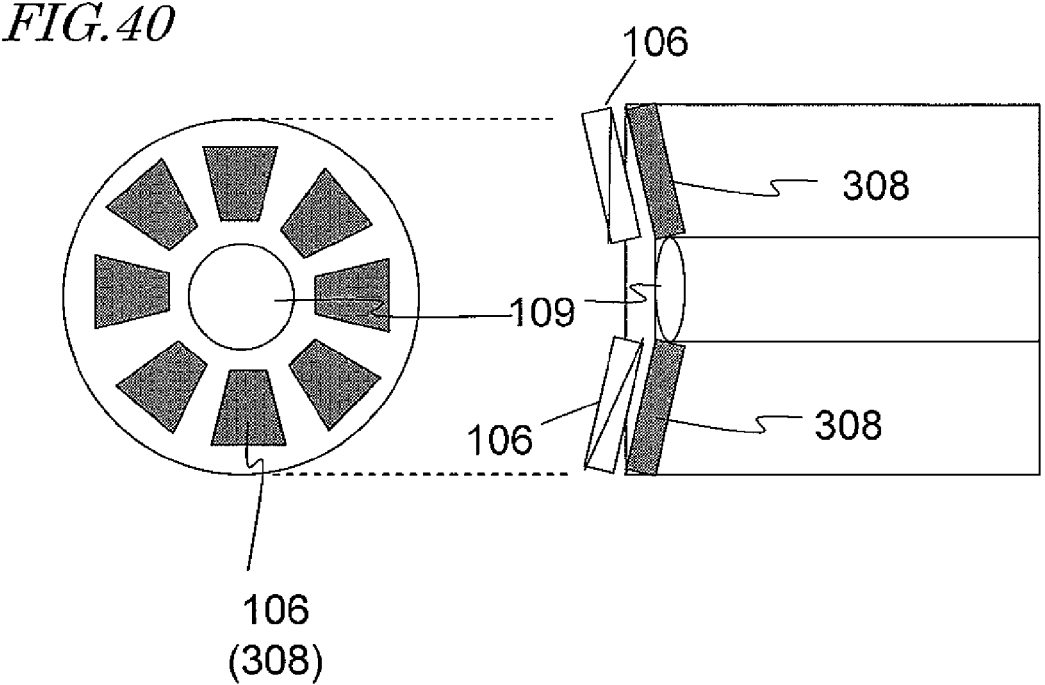
FIG. 40 illustrates yet another modified example of the first and second embodiments of the present disclosure.

FIG. 40 illustrates a configuration for a tip portion, of which the center portion is recessed so that the optical axis of the illuminating light is tilted with respect to that of the image capturing light. The shooting lens 109 is arranged in the recessed center portion and is surrounded with a plurality of LED light sources 308. As a result, the effect of surrounding the object's target region with a large light source can be achieved, and therefore, a lot of specular reflection is produced.

Figure 41:
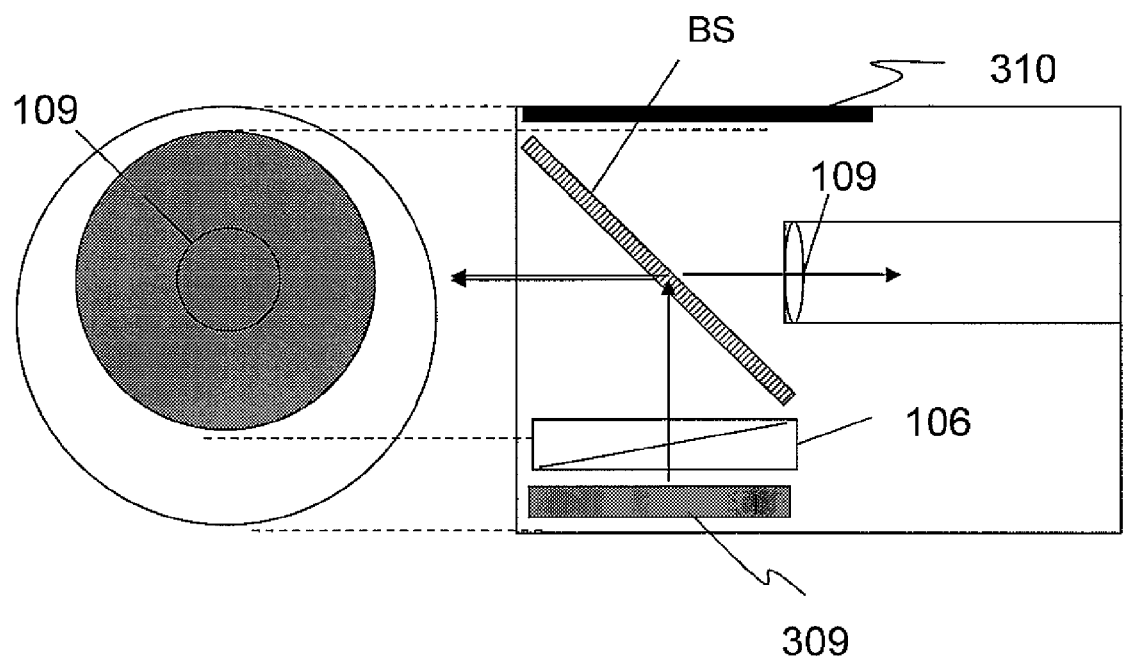
FIG. 41 illustrates yet another modified example of the first and second embodiments of the present disclosure.

FIG. 41 illustrates a configuration that uses a coaxial episcopic illumination in which the optical axis of the illuminating light can be the same as that of the image capturing light. Non-polarized light that has been emitted from a circular surface-emitting LED light source 309 is transmitted through a circular plane of polarization control element 106 and then incident on a broad band non-polarizing beams splitter (BS) at an angle of incidence of 45 degrees. The broad band non-polarizing BS transmits a half of the incident light falling within the visible radiation range and reflects the other half, and has the property of maintaining its polarization in the meantime. That is why plane polarized light is radiated toward the object as it is. Likewise, a half of the returning light is also transmitted and enters the shooting lens 109. According to this configuration, to substantially prevent a part of the light that has been emitted from the light source and transmitted through the broad band non-polarizing BS from being reflected inside of the apparatus, a light absorbing plate 310 is suitably arranged. Although the broad band non-polarizing BS has a plate shape in this example, the BS may also have a cube shape. In that case, however, the light source will be reflected so intensely that an appropriate countermeasure needs to be taken.

Optionally, an LED light source that emits plane polarized light may be used and its plane of polarization may be rotated by the plane of polarization control element.

Each and every one of the embodiments described above includes a rotating polarized light source and a light intensity image sensor in combination. However, if the object is a specular reflector, that combination may be replaced with a combination of a non-polarized light source and a polarization image sensor. In that case, the plane of polarization control element 106 shown in FIG. 1C is no longer necessary but the image sensor 110 is replaced with a polarization image sensor. As the polarization image sensor, an element that can capture a polarization image in a certain wavelength range as well as a visible color light intensity may be used. In that embodiment, the processing section receives and processes a single polarization image captured instead of the group of light intensity images 1301 shown in FIG. 13. Then, the intensity maximizing angle image YPH and degree of intensity modulation image YD shown in FIG. 13 may be replaced with a polarization principal axis angle (phase) image and a degree of polarization image, respectively.

The present disclosure is broadly applicable to the field of image processing that needs observing, checking, or recognizing the object's surface unevenness using a medical endoscope, a medical camera for dermatologists, dentists, ophthalmologists or surgeons, an industrial endoscope, a fingerprint scanner, or an optical surface analyzer.

While the present invention has been described with respect to preferred embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. An image processing apparatus comprising:
a polarized light source section which sequentially illuminates an object with three or more kinds of plane polarized light rays, of which the planes of polarization define mutually different angles;
an image capturing section which sequentially captures an image of the object that is being illuminated with each of the three or more kinds of plane polarized light rays; and
an image processing section,
wherein the image processing section includes:
a varying intensity processing section which calculates a state of polarized light being reflected from the object's surface by processing the intensity of the image that has been shot by the image capturing section;
a reflection decision section which distinguishes, based on the output of the varying intensity processing section, a multi-reflection region in which incoming light is reflected twice from a recessed region before returning from a once-reflected region in which the incoming light is reflected only once from the object's surface before returning; and
a mirror image search section which locates a pair of such multi-reflection regions in which the incoming light is reflected twice from the recessed region on the object's surface before returning, and wherein based on the pair of multi-reflection regions, the image processing section generates an image representing the recessed region on the object's surface.

2. The image processing apparatus of claim 1, wherein the image processing section includes:
a recessed region connecting section which generates group segments based on multiple pairs of the multi-reflection regions and which connects those segments together, thereby estimating the position of the recessed region; and
a cross-sectional shape modeling section which determines a cross-sectional shape of the recessed region.

3. The image processing apparatus of claim 2, wherein the image processing section includes a normal reproducing section which generates a normal image by combining together surface normals with respect to the multi-reflection region and a surface normal to the once-reflected region.

4. The image processing apparatus of claim 3, comprising:
a light source direction setting section which sets a direction in which the position of a light source is virtually shifted;
a shifted light source image generating section which generates a shifted light source image representing how the light source looks if its position is virtually shifted and which also generates the object's light intensity image using the normal image and a physical reflection model; and
an image display section which superposes the shifted light source image and the light intensity image one upon the other and displays their synthetic image.

5. The image processing apparatus of claim 1, wherein the polarized light source section and the image capturing section are attached to an endoscope.

6. The image processing apparatus of claim 1, wherein the polarized light source section gets non-polarized light transmitted through a plane of polarization changer, thereby radiating plane polarized light rays, of which the plane of polarization sequentially changes into one of three or more different types after another.

7. The image processing apparatus of claim 1, wherein the polarized light source section includes a light guide that guides non-polarized light to the plane of polarization changer.

8. The image processing apparatus of claim 1, wherein the image capturing section includes either a monochrome image sensor or a color image sensor.

9. The image processing apparatus of claim 1, comprising an intensity adding and averaging section which adds together a plurality of light intensity images obtained by the image capturing section and calculates their average with the object sequentially irradiated with three or more plane polarized light rays, of which the planes of polarization define mutually different angles, thereby generating an average light intensity image corresponding to an image under non-polarized light source.

10. The image processing apparatus of claim 1, wherein the varying intensity processing section obtains a relation between the angle of the plane of polarization and the intensity value of each pixel based on a pixel signal supplied from the image capturing section, thereby generating not only an intensity maximizing angle image that is defined by the angle of the plane of polarization that maximizes the intensity value with respect to each said pixel but also a degree of intensity modulation image that is defined by the ratio of the amplitude of variation in the intensity value caused by the change of the plane of polarization to an average intensity value with respect to each said pixel.

11. The image processing apparatus of claim 10, comprising an image display section which superposes either the intensity maximizing angle image or the degree of intensity modulation image on the light intensity image, thereby generating and displaying their synthetic image.

12. The image processing apparatus of claim 10, wherein based on the intensity maximizing angle image and the degree of intensity modulation image, the reflection decision section extracts, as pixels that form the multi-reflection regions, pixels, of which the degrees of intensity modulation are equal to or greater than a preset value, from a pseudo-color image that uses the intensity maximizing angle and the degree of intensity modulation as a hue angle and as a saturation, respectively.

13. The image processing apparatus of claim 2, wherein the recessed region connecting section estimates the azimuth angle of a surface normal to the recessed region.

14. The image processing apparatus of claim 2, wherein the cross-sectional shape modeling section makes a model of the cross-sectional shape of the recessed region with a particular function, and
wherein by taking advantage of a property of the multi-reflection region, to which a surface normal defines an azimuth angle of approximately 45 degrees, the cross-sectional shape modeling section estimates the zenith angle of a surface normal with respect to an arbitrary position in the recessed region.

15. The image processing apparatus of claim 1, wherein the polarized light source section irradiates the object with light, which has been transmitted through a plane of polarization changer and of which the plane of polarization sequentially changes into one of three or more kinds after another, via a relay lens optical system.

16. The image processing apparatus of claim 1, wherein the polarized light source section includes an optical system in which either a plurality of concentric ring light sources or a surface-emitting light source is combined with a plane of polarization changer.

17. The image processing apparatus of claim 1, wherein the polarized light source section includes an optical system in which a surface-emitting light source, having an illumination system optical axis that faces inward with respect to the optical axis of the image capturing system, is combined with the plane of polarization changer.

18. The image processing apparatus of claim 1, wherein the polarized light source section includes an optical system in which a non-polarizing broadband beam splitter, a surface-emitting light source, and a plane of polarization changer are combined with each other.

19. A method for operating an image processing apparatus comprising:
a polarized light illuminating step in which a polarized light source section sequentially illuminates an object with three or more kinds of plane polarized light rays, of which the planes of polarization define mutually different angles;
an image capturing step in which an image capturing section sequentially captures an image of the object that is being illuminated with each of the three or more kinds of plane polarized light rays; and
an image processing step,
wherein the image processing step includes:
a varying intensity processing step in which a varying intensity processing section calculates a state of polarized light being reflected from the object's surface by processing the intensity of the image that has been shot in the image capturing step;
a reflection decision step in which a reflection decision section distinguishes, based on a result of the varying intensity processing step, a multi-reflection region in which incoming light is reflected twice from a recessed region before returning from a once-reflected region in which the incoming light is reflected only once from the object's surface before returning;
a mirror image searching step in which a mirror image search section locates a pair of such multi-reflection regions in which the incoming light is reflected twice from the recessed region on the object's surface before returning; and
a step in which an image processing section generates an image representing the recessed region on the object's surface based on the pair of multi-reflection regions.

20. An endoscope device comprising:
a polarized light source section which sequentially illuminates an object with three or more kinds of plane polarized light rays, of which the planes of polarization define mutually different angles;
an image capturing section which sequentially captures an image of the object that is being illuminated with each of the three or more kinds of plane polarized light rays;
an image processing section; and
a display section which displays an image based on the output of the image processing section,
wherein the image processing section includes:
a varying intensity processing section which calculates a state of polarized light being reflected from the object's surface by processing the intensity of the image that has been shot by the image capturing section; and
a pseudo-color image transforming section which generates a pseudo-color image based on the output of the varying intensity processing section,
wherein the varying intensity processing section obtains a relation between the angle of the plane of polarization and the intensity value of each pixel based on a pixel signal supplied from the image capturing section, thereby generating not only an intensity maximizing angle image that is defined by the angle of the plane of polarization that maximizes the intensity value with respect to each said pixel but also a degree of intensity modulation image that is defined by the ratio of the amplitude of variation in the intensity value caused by the change of the plane of polarization to an average intensity value with respect to each said pixel, and wherein based on the intensity maximizing angle image and the degree of intensity modulation image, the pseudo-color image transforming section generates a pseudo-color image that uses the intensity maximizing angle and the degree of intensity modulation as a hue angle and as a saturation, respectively, synthesizes the pseudo-color image and the light intensity image together, and gets their synthetic image displayed on the display section.

21. A method for operating an image processing apparatus comprising:
a polarized light illuminating step in which a polarized light source section activates means for sequentially illuminating an object with three or more kinds of plane polarized light rays, of which the planes of polarization define mutually different angles;
an image capturing step in which an image capturing section sequentially captures an image of the object that is being illuminated with each of the three or more kinds of plane polarized light rays; and
an image processing step,
wherein the image processing step includes:
a varying intensity processing step in which a varying intensity processing section calculates a state of polarized light being reflected from the object's surface by processing the intensity of the image that has been shot in the image capturing step;
a reflection decision step in which a reflection decision section distinguishes, based on a result of the varying intensity processing step, a multi-reflection region in which incoming light is reflected twice from a recessed region before returning from a once-reflected region in which the incoming light is reflected only once from the object's surface before returning;
a mirror image searching step in which a mirror image search section locates a pair of such multi-reflection regions in which the incoming light is reflected twice from the recessed region on the object's surface before returning; and
a step in which an image processing section generates an image representing the recessed region on the object's surface based on the pair of multi-reflection regions.

22. A method for operating an image processing apparatus comprising:
an image capturing step in which an image capturing section sequentially captures an image of an object that is being illuminated with each of three or more kinds of plane polarized light rays, of which the planes of polarization define mutually different angles; and
an image processing step,
wherein the image processing step includes:
a varying intensity processing step in which a varying intensity processing section calculates a state of polarized light being reflected from the object's surface by processing the intensity of the image that has been shot in the image capturing step;
a reflection decision step in which a reflection decision section distinguishes, based on a result of the varying intensity processing step, a multi-reflection region in which incoming light is reflected twice from a recessed region before returning from a once-reflected region in which the incoming light is reflected only once from the object's surface before returning;
a mirror image searching step in which a mirror image search section locates a pair of such multi-reflection regions in which the incoming light is reflected twice from the recessed region on the object's surface before returning; and
a step in which an image processing section generates an image representing the recessed region on the object's surface based on the pair of multi-reflection regions.

23. A method for operating an image processing apparatus comprising an image processing step for processing an image of an object that has been captured while the object is being illuminated with each of three or more kinds of plane polarized light rays, of which the planes of polarization define mutually different angles,
wherein the image processing step includes:
a varying intensity processing step in which a varying intensity processing section calculates a state of polarized light being reflected from the object's surface by processing the intensity of the image that has been shot;
a reflection decision step in which a reflection decision section distinguishes, based on a result of the varying intensity processing step, a multi-reflection region in which incoming light is reflected twice from a recessed region before returning from a once-reflected region in which the incoming light is reflected only once from the object's surface before returning;
a mirror image searching step in which a mirror image search section locates a pair of such multi-reflection regions in which the incoming light is reflected twice from the recessed region on the object's surface before returning; and
a step in which an image processing section generates an image representing the recessed region on the object's surface based on the pair of multi-reflection regions.

24. An image processing apparatus comprising an image processing section for processing an image of an object that has been captured while the object is being illuminated with each of three or more kinds of plane polarized light rays, of which the planes of polarization define mutually different angles,
wherein the image processing section includes:
a varying intensity processing section which calculates a state of polarized light being reflected from the object's surface by processing the intensity of the image that has been shot;
a reflection decision section which distinguishes, based on a result obtained by the varying intensity processing section, a multi-reflection region in which incoming light is reflected twice from a recessed region before returning from a once-reflected region in which the incoming light is reflected only once from the object's surface before returning;
a mirror image search section which locates a pair of such multi-reflection regions in which the incoming light is reflected twice from the recessed region on the object's surface before returning; and
an image forming section which generates an image representing the recessed region on the object's surface based on the pair of multi-reflection regions.

* * * * *